United States Patent
Schelwies et al.

(10) Patent No.: US 11,192,873 B2
(45) Date of Patent: *Dec. 7, 2021

(54) PROCESS FOR THE PREPARATION OF UNSATURATED CARBOXYLIC ACIDS BY CARBONYLATION OF ALLYL ALCOHOLS AND THEIR ACYLATION PRODUCTS

(71) Applicant: BASF SE, Ludwigshafen am Rhein (DE)

(72) Inventors: Mathias Schelwies, Ludwigshafen am Rhein (DE); Rocco Paciello, Ludwigshafen am Rhein (DE); Ralf Pelzer, Lampertheim (DE); Wolfgang Siegel, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/487,161

(22) PCT Filed: Feb. 13, 2018

(86) PCT No.: PCT/EP2018/053535
§ 371 (c)(1),
(2) Date: Aug. 20, 2019

(87) PCT Pub. No.: WO2018/153727
PCT Pub. Date: Aug. 30, 2018

(65) Prior Publication Data
US 2020/0055834 A1 Feb. 20, 2020

(30) Foreign Application Priority Data

Feb. 24, 2017 (EP) .................... 17157950

(51) Int. Cl.
*C07C 51/12* (2006.01)
*C07C 57/02* (2006.01)
*C07D 307/92* (2006.01)

(52) U.S. Cl.
CPC ................. *C07D 307/92* (2013.01)

(58) Field of Classification Search
CPC ................. C07C 51/12; C07C 57/02
See application file for complete search history.

(56) References Cited

U.S. PATENT DOCUMENTS

| 4,801,743 | A | 1/1989 | Baugh et al. | |
| 6,015,923 | A * | 1/2000 | Burke | C07C 51/12 562/519 |
| 8,932,839 | B2 | 1/2015 | Breuer et al. | |
| 9,447,404 | B2 | 9/2016 | Breuer et al. | |
| 10,190,112 | B2 | 1/2019 | Breuer et al. | |
| 2018/0134680 | A1 | 5/2018 | Siegel et al. | |
| 2019/0119665 | A1 | 4/2019 | Breuer et al. | |
| 2019/0144899 | A1 | 5/2019 | Breuer et al. | |
| 2020/0123586 | A1 * | 4/2020 | Siegel | C12P 17/04 |

FOREIGN PATENT DOCUMENTS

| CA | 1242741 A | 10/1988 | |
| DE | 2217534 A1 | 10/1973 | |
| DE | 4301555 C1 | 7/1994 | |
| EP | 0146859 A2 | 7/1985 | |
| EP | 0428979 A2 | 5/1991 | |
| WO | WO-9206063 A2 * | 4/1992 | ........... C07C 69/587 |
| WO | WO-2010139719 A2 * | 12/2010 | ............... C12N 9/90 |
| WO | WO-2015061764 A1 | 4/2015 | |
| WO | WO-2018154048 A1 * | 8/2018 | ................ C12P 7/62 |

OTHER PUBLICATIONS

Upar, K.B., et al. "Efficient enantioselective synthesis of (+)-sclareolide and (+)-tetrahydroactinidiolide: chiral LBA-induced biomimetic cyclization." Tetrahedron: Asymmetry. (2009), vol. 20, pp. 1637-1640. (Year: 2009).*

Gabriele, B., et al., "A simple catalytic system for the substitutive carbonylation of allyl alcohols to β,γ-unsaturated acids or esters", Journal of Molecular Cataylsis A: Chemical, vol. 111, Nos. 1-2, (1996), pp. 43-48.

International Search Report for PCT/EP2018/053535 dated Aug. 21, 2018.

Mandai, T., "Migratory Insertion Reactions of Allyl, Propargyl, and Allenylpalladium Derivatives Involving Carbon Monoxide and Related Derivatives", in *Handbook of Organopalladium Chemistry for Organic Syntesis*, Negishi, E., Ed. Wiley-VCH: New York 2002, vol. 2, pp. 2505-2517.

Matsuzaka, H., et al., "A Novel Palladium- or Platinum-Catalyzed Cyclocarbonylation Reaction of Cinnamyl Compounds for Synthesis of 1-Naphthol Derivatives", Journal of Organic Chemistry, vol. 53, No. 16, (1988), pp. 3832-3838.

Murahashi, S.-I., et al., "Palladium (0)-Catalyzed Alkoxycarbonylation of Allyl Phosphates and Acetates", Journal of Organic Chemistry, vol. 58, No. 6, (1993), pp. 1538-1545.

Murahashi, S.-I., et al., "Palladium(0)-Catalyzed Carbonylation of Allyl Phosphates and Allyl Acetates. Selective Synthesis of β,γ-Unsaturated Esters", Tetrahedron Letters, vol. 29, No. 39, (1988), pp. 4945-4948.

Tsuji, J., et al., "Organic Syntheses by Means of Noble Metal Compounds. VIII. Catalytic Carbonylation of Allylic Compounds with Palladium Chloride", Journal of the American Chemical Soceity, vol. 86, (1964), pp. 4350-4353.

(Continued)

*Primary Examiner* — John S Kenyon

(74) *Attorney, Agent, or Firm* — Faegre Drinker Biddle & Reath LLP

(57) ABSTRACT

The present invention relates to a process for carbonylating allyl alcohols at low temperature, low pressure and/or low catalyst loading. In an alternative embodiment, an acylation product of the allyl alcohol is used for the carbonylation. The present invention likewise relates to the preparation of conversion products of these carbonylation products and specifically of (−)-ambrox.

40 Claims, No Drawings

Specification includes a Sequence Listing.

(56) References Cited

OTHER PUBLICATIONS

Upar, K., et al., "Efficient enantioselective synthesis of (+)-sclareolide and (+)-tetrahydroactinidiolide: chiral LBA-induced biomimetic cyclization", Tetrahedron: Asymmetry, vol. 20, No. 14, (2009), pp. 1637-1640.
Written Opinion of the International Searching Authority for PCT/EP2018/053535 dated Aug. 21, 2018.
Wu, L., et al., "Palladium-Catalyzed Carbonylative Transformation of $C(sp^3)$-X Bonds", ACS Catalysis, vol. 4, No. 9, (2014), pp. 2977-2989.

\* cited by examiner

```
                       SEQUENCE LISTING

<160> NUMBER OF SEQ ID NOS: 11

<210> SEQ ID NO 1
<211> LENGTH: 6525
<212> TYPE: DNA
<213> ORGANISM: Zymomonas mobilis
<220> FEATURE:
<221> NAME/KEY: CDS
<222> LOCATION: (154)..(2328)

<400> SEQUENCE: 1
cgatcaccac aattcagcaa attgtgaaca tcatcacgtt catctttccc tggttgccaa       60
tggcccattt tcctgtcagt aacgagaagg tcgcgaattc aggcgctttt tagactggtc     120
gtaatgaaca attcttaaga aggagatata cat atg ggt att gac aga atg aat     174
                                    Met Gly Ile Asp Arg Met Asn
                                      1               5 agc tta agt cgc ttg tta atg aag aag att ttc ggg gct gaa aaa acc     222
```

```
                Ser Leu Ser Arg Leu Leu Met Lys Lys Ile Phe Gly Ala Glu Lys Thr
                         10                  15                  20 tcg tat aaa ccg gct tcc gat acc ata atc gga acg gat acc ctg aaa             270
Ser Tyr Lys Pro Ala Ser Asp Thr Ile Ile Gly Thr Asp Thr Leu Lys
         25                  30                  35 aga ccg aac cgg cgg cct gaa ccg acg gca aaa gtc gac aaa acg ata             318
Arg Pro Asn Arg Arg Pro Glu Pro Thr Ala Lys Val Asp Lys Thr Ile
 40                  45                  50                  55 ttc aag act atg ggg aat agt ctg aat aat acc ctt gtt tca gcc tgt             366
Phe Lys Thr Met Gly Asn Ser Leu Asn Asn Thr Leu Val Ser Ala Cys
                     60                  65                  70 gac tgg ttg atc gga caa caa aag ccc gat ggt cat tgg gtc ggt gcc             414
Asp Trp Leu Ile Gly Gln Gln Lys Pro Asp Gly His Trp Val Gly Ala
             75                  80                  85 gtg gaa tcc aat gct tcg atg gaa gca gaa tgg tgt ctg gcc ttg tgg             462
Val Glu Ser Asn Ala Ser Met Glu Ala Glu Trp Cys Leu Ala Leu Trp
         90                  95                 100 ttt ttg ggt ctg gaa gat cat ccg ctt cgt cca aga ttg ggc aat gct             510
Phe Leu Gly Leu Glu Asp His Pro Leu Arg Pro Arg Leu Gly Asn Ala
105                 110                 115 ctt ttg gaa atg cag cgg gaa gat ggc tct tgg gga gtc tat ttc ggc             558
Leu Leu Glu Met Gln Arg Glu Asp Gly Ser Trp Gly Val Tyr Phe Gly
120                 125                 130                 135 gct gga aat ggc gat atc aat gcc acg gtt gaa gcc tat gcg gcc ttg             606
Ala Gly Asn Gly Asp Ile Asn Ala Thr Val Glu Ala Tyr Ala Ala Leu
                140                 145                 150 cgg tct ttg ggg tat tct gcc gat aat cct gtt ttg aaa aaa gcg gca             654
Arg Ser Leu Gly Tyr Ser Ala Asp Asn Pro Val Leu Lys Lys Ala Ala
            155                 160                 165 gca tgg att gct gaa aaa ggc gga tta aaa aat atc cgt gtc ttt acc             702
Ala Trp Ile Ala Glu Lys Gly Gly Leu Lys Asn Ile Arg Val Phe Thr
        170                 175                 180 cgt tat tgg ctg gcg ttg atc ggg gaa tgg cct tgg gaa aag acc cct             750
Arg Tyr Trp Leu Ala Leu Ile Gly Glu Trp Pro Trp Glu Lys Thr Pro
185                 190                 195 aac ctt ccc cct gaa att atc tgg ttc cct gat aat ttt gtc ttt tcg             798
Asn Leu Pro Pro Glu Ile Ile Trp Phe Pro Asp Asn Phe Val Phe Ser
200                 205                 210                 215 att tat aat ttt gcc caa tgg gcg cgg gca acc atg gtg ccg att gct             846
Ile Tyr Asn Phe Ala Gln Trp Ala Arg Ala Thr Met Val Pro Ile Ala
                220                 225                 230 att ctg tcc gcg aga cga cca agc cgc ccg ctg cgc cct caa gac cga             894
Ile Leu Ser Ala Arg Arg Pro Ser Arg Pro Leu Arg Pro Gln Asp Arg
            235                 240                 245 ttg gat gaa ctg ttt cca gaa ggc cgc gct cgc ttt gat tat gaa ttg             942
Leu Asp Glu Leu Phe Pro Glu Gly Arg Ala Arg Phe Asp Tyr Glu Leu
        250                 255                 260 ccg aaa aaa gaa ggc atc gat ctt tgg tcg caa ttt ttc cga acc act             990
Pro Lys Lys Glu Gly Ile Asp Leu Trp Ser Gln Phe Phe Arg Thr Thr
265                 270                 275 gac cgt gga tta cat tgg gtt cag tcc aat ctg tta aag cgc aat agc            1038
Asp Arg Gly Leu His Trp Val Gln Ser Asn Leu Leu Lys Arg Asn Ser
280                 285                 290                 295 ttg cgt gaa gcc gct atc cgt cat gtt ttg gaa tgg att atc cgg cat            1086
Leu Arg Glu Ala Ala Ile Arg His Val Leu Glu Trp Ile Ile Arg His
                300                 305                 310 cag gat gcc gat ggc ggt tgg ggt gga att cag cca cct tgg gtc tat            1134
Gln Asp Ala Asp Gly Gly Trp Gly Gly Ile Gln Pro Pro Trp Val Tyr
            315                 320                 325
```

```
ggt ttg atg gcg tta cat ggt gaa ggc tat cag ctt tat cat ccg gtg         1182
Gly Leu Met Ala Leu His Gly Glu Gly Tyr Gln Leu Tyr His Pro Val
            330                 335                 340 atg gcc aag gct ttg tcg gct ttg gat gat ccc ggt tgg cga cat gac         1230
Met Ala Lys Ala Leu Ser Ala Leu Asp Asp Pro Gly Trp Arg His Asp
345                 350                 355 aga ggc gag tct tct tgg ata cag gcc acc aat agt ccg gta tgg gat         1278
Arg Gly Glu Ser Ser Trp Ile Gln Ala Thr Asn Ser Pro Val Trp Asp
360                 365                 370                 375 aca atg ttg gcc ttg atg gcg tta aaa gac gcc aag gcc gag gat cgt         1326
Thr Met Leu Ala Leu Met Ala Leu Lys Asp Ala Lys Ala Glu Asp Arg
            380                 385                 390 ttt acg ccg gaa atg gat aag gcc gcc gat tgg ctt ttg gct cga cag         1374
Phe Thr Pro Glu Met Asp Lys Ala Ala Asp Trp Leu Leu Ala Arg Gln
                395                 400                 405 gtc aaa gtc aaa ggc gat tgg tca atc aaa ctg ccc gat gtt gaa ccc         1422
Val Lys Val Lys Gly Asp Trp Ser Ile Lys Leu Pro Asp Val Glu Pro
410                 415                 420 ggt gga tgg gca ttt gaa tat gcc aat gat cgc tat ccc gat acc gat         1470
Gly Gly Trp Ala Phe Glu Tyr Ala Asn Asp Arg Tyr Pro Asp Thr Asp
            425                 430                 435 gat acc gcc gtc gct ttg atc gcc ctt tcc tct tat cgt gat aag gag         1518
Asp Thr Ala Val Ala Leu Ile Ala Leu Ser Ser Tyr Arg Asp Lys Glu
440                 445                 450                 455 gag tgg caa aag aaa ggc gtt gag gac gcc att acc cgt ggg gtt aat         1566
Glu Trp Gln Lys Lys Gly Val Glu Asp Ala Ile Thr Arg Gly Val Asn
                460                 465                 470 tgg ttg atc gcc atg caa agc gaa tgt ggc ggt tgg gga gcc ttt gat         1614
Trp Leu Ile Ala Met Gln Ser Glu Cys Gly Gly Trp Gly Ala Phe Asp
            475                 480                 485 aag gat aat aac aga agt atc ctt tcc aaa att cct ttt tgt gat ttc         1662
Lys Asp Asn Asn Arg Ser Ile Leu Ser Lys Ile Pro Phe Cys Asp Phe
                490                 495                 500 gga gaa tct att gat ccg cct tca gtc gat gta acg gcg cat gtt tta         1710
Gly Glu Ser Ile Asp Pro Pro Ser Val Asp Val Thr Ala His Val Leu
505                 510                 515 gag gcc ttt ggc acc ttg gga ctg tcc cgc gat atg ccg gtc atc caa         1758
Glu Ala Phe Gly Thr Leu Gly Leu Ser Arg Asp Met Pro Val Ile Gln
520                 525                 530                 535 aaa gcg atc gac tat gtc cgt tcc gaa cag gaa gcc gaa ggc gcg tgg         1806
Lys Ala Ile Asp Tyr Val Arg Ser Glu Gln Glu Ala Glu Gly Ala Trp
            540                 545                 550 ttt ggt cgt tgg ggc gtt aat tat atc tat ggc acc ggt gcg gtt ctg         1854
Phe Gly Arg Trp Gly Val Asn Tyr Ile Tyr Gly Thr Gly Ala Val Leu
                555                 560                 565 cct gct ttg gcg gcg atc ggt gaa gat atg acc cag cct tac atc acc         1902
Pro Ala Leu Ala Ala Ile Gly Glu Asp Met Thr Gln Pro Tyr Ile Thr
            570                 575                 580 aag gct tgc gat tgg ctg gtc gca cat cag cag gaa gac ggc ggt tgg         1950
Lys Ala Cys Asp Trp Leu Val Ala His Gln Gln Glu Asp Gly Gly Trp
585                 590                 595 ggc gaa agc tgc tct tcc tat atg gag att gat tcc att ggg aag ggc         1998
Gly Glu Ser Cys Ser Ser Tyr Met Glu Ile Asp Ser Ile Gly Lys Gly
600                 605                 610                 615 cca acc acg ccg tcc cag act gct tgg gct ttg atg ggg ttg atc gcg         2046
Pro Thr Thr Pro Ser Gln Thr Ala Trp Ala Leu Met Gly Leu Ile Ala
            620                 625                 630 gcc aat cgt ccc gaa gat tat gaa gcc att gcc aag gga tgc cat tat         2094
Ala Asn Arg Pro Glu Asp Tyr Glu Ala Ile Ala Lys Gly Cys His Tyr
                635                 640                 645
```

-continued

```
ctg att gat cgc caa gag cag gat ggt agc tgg aaa gaa gaa gaa ttc      2142
Leu Ile Asp Arg Gln Glu Gln Asp Gly Ser Trp Lys Glu Glu Glu Phe
        650                 655                 660 acc ggc acc gga ttc ccc ggt tat ggc gtg ggt cag acg atc aag ttg      2190
Thr Gly Thr Gly Phe Pro Gly Tyr Gly Val Gly Gln Thr Ile Lys Leu
665                 670                 675 gat gat ccg gct tta tcg aaa cga ttg ctt caa ggc gct gaa ctg tca      2238
Asp Asp Pro Ala Leu Ser Lys Arg Leu Leu Gln Gly Ala Glu Leu Ser
680                 685                 690                 695 cgg gcg ttt atg ctg cgt tat gat ttt tat cgg caa ttc ttc ccg att      2286
Arg Ala Phe Met Leu Arg Tyr Asp Phe Tyr Arg Gln Phe Phe Pro Ile
                700                 705                 710 atg gcg tta agt cgg gca gag aga ctg att gat ttg aat aat              2328
Met Ala Leu Ser Arg Ala Glu Arg Leu Ile Asp Leu Asn Asn
                715                 720                 725 tgatagtatt ggggcggagg agtcttttta aaagagacta ctccgtccta ttttcgagga    2388
tccgtcgacc tgcagccaag cttggctgtt ttggcggatg agagaagatt ttcagcctga    2448
tacagattaa atcagaacgc agaagcggtc tgataaaaca gaatttgcct ggcggcagta    2508
gcgcggtggt cccacctgac cccatgccga actcagaagt gaaacgccgt agcgccgatg    2568
gtagtgtggg gtctccccat gcgagagtag ggaactgcca ggcatcaaat aaaacgaaag    2628
gctcagtcga aagactgggc ctttcgtttt atctgttgtt tgtcggtgaa cgctctcctg    2688
agtaggacaa atccgccggg agcggatttg aacgttgcga agcaacggcc cggagggtgg    2748
cgggcaggac gcccgccata aactgccagg catcaaatta agcagaaggc catcctgacg    2808
gatggccttt ttgcgtttct acaaactctt tgtttatttt tctaaatac attcaaatat     2868 gtatccgctc atgagacaat aaccctgata aatgcttcaa taatattgaa aaggaagag     2928 tatgagtatt caacatttcc gtgtcgccct tattcccttt tttgcggcat tttgccttcc    2988 tgttttgct cacccagaaa cgctggtgaa agtaaaagat gctgaagatc agttgggtgc     3048
acgagtgggt tacatcgaac tggatctcaa cagcggtaag atccttgaga gttttcgccc    3108
cgaagaacgt tttccaatga tgagcacttt taaagttctg ctatgtggcg cggtattatc    3168
ccgtgttgac gccgggcaag agcaactcgg tcgccgcata cactattctc agaatgactt    3228
ggttgagtac tcaccagtca cagaaaagca tcttacggat ggcatgacag taagagaatt    3288
atgcagtgct gccataacca tgagtgataa cactgcggcc aacttacttc tgacaacgat    3348
cggaggaccg aaggagctaa ccgcttttt gcacaacatg ggggatcatg taactcgcct     3408
tgatcgttgg gaaccggagc tgaatgaagc cataccaaac gacgagcgtg acaccacgat    3468
gcctgtagca atggcaacaa cgttgcgcaa actattaact ggcgaactac ttactctagc    3528
ttcccggcaa caattaatag actggatgga ggcggataaa gttgcaggac cacttctgcg    3588
ctcggccctt ccggctggct ggtttattgc tgataaatct ggagccggtg agcgtgggtc    3648
tcgcggtatc attgcagcac tggggccaga tggtaagccc tcccgtatcg tagttatcta    3708
cacgacgggg agtcaggcaa ctatggatga acgaaataga cagatcgctg agataggtgc    3768
ctcactgatt aagcattggt aactgtcaga ccaagtttac tcatatatac tttagattga    3828 tttaaaacttt cattttttaat ttaaaaggat ctaggtgaag atcctttttg ataatctcat   3888
gaccaaaatc ccttaacgtg agttttcgtt ccactgagcg tcagaccccg tagaaaagat    3948
caaaggatct tcttgagatc cttttttttct gcgcgtaatc tgctgcttgc aaacaaaaaa   4008
accaccgcta ccagcggtgg tttgtttgcc ggatcaagag ctaccaactc tttttccgaa    4068
```

```
ggtaactggc ttcagcagag cgcagatacc aaatactgtc cttctagtgt agccgtagtt    4128
aggccaccac ttcaagaact ctgtagcacc gcctacatac ctcgctctgc taatcctgtt    4188
accagtggct gctgccagtg gcgataagtc gtgtcttacc gggttggact caagacgata    4248
gttaccggat aaggcgcagc ggtcgggctg aacgggggt tcgtgcacac agcccagctt    4308
ggagcgaacg acctacaccg aactgagata cctacagcgt gagctatgag aaagcgccac    4368
gcttcccgaa gggagaaagg cggacaggta tccggtaagc ggcagggtcg aacaggaga    4428 gcgcacgagg gagcttccag ggggaaacgc ctggtatctt tatagtcctg tcgggtttcg    4488
ccacctctga cttgagcgtc gattttgtg atgctcgtca gggggcgga gcctatggaa    4548 aaacgccagc aacgcggcct ttttacggtt cctggccttt tgctggcctt ttgctcacat    4608
gttctttcct gcgttatccc ctgattctgt ggataaccgt attaccgcct ttgagtgagc    4668
tgataccgct cgccgcagcc gaacgaccga gcgcagcgag tcagtgagcg aggaagcgga    4728
agagcgcctg atgcggtatt ttctccttac gcatctgtgc ggtatttcac accgcatata    4788
tggtgcactc tcagtacaat ctgctctgat gccgcatagt taagccagta tacactccgc    4848
tatcgctacg tgactgggtc atggctgcgc cccgacaccc gccaacaccc gctgacgcgc    4908
cctgacgggc ttgtctgctc ccggcatccg cttacagaca agctgtgacc gtctccggga    4968
gctgcatgtg tcagaggttt tcaccgtcat caccgaaacg cgcgaggcag ctgcggtaaa    5028
gctcatcagc gtggtcgtga agcgattcac agatgtctgc ctgttcatcc gcgtccagct    5088
cgttgagttt ctccagaagc gttaatgtct ggcttctgat aaagcgggcc atgttaaggg    5148
cggttttttc ctgtttggtc actgatgcct ccgtgtaagg gggatttctg ttcatgggg    5208 taatgatacc gatgaaacga gagaggatgc tcacgatacg ggttactgat gatgaacatg    5268
cccggttact ggaacgttgt gagggtaaac aactggcggt atggatgcgg cgggaccaga    5328
gaaaaatcac tcagggtcaa tgccagcgct tcgttaatac agatgtaggt gttccacagg    5388
gtagccagca gcatcctgcg atgcagatcc ggaacataat ggtgcagggc gctgacttcc    5448
gcgtttccag actttacgaa acacggaaac cgaagaccat tcatgttgtt gctcaggtcg    5508
cagacgtttt gcagcagcag tcgcttcacg ttcgctcgcg tatcggtgat tcattctgct    5568
aaccagtaag gcaaccccgc cagcctagcc gggtcctcaa cgacaggagc acgatcatgc    5628
gcacccgtgg ccaggaccca acgctgcccg agatgcgccg cgtgcggctg ctggagatgg    5688
cggacgcgat ggatatgttc tgccaagggt tggtttgcgc attcacagtt ctccgcaaga    5748
attgattggc tccaattctt ggagtggtga atccgttagc gaggtgccgc cggcttccat    5808
tcaggtcgag gtggcccggc tccatgcacc gcgacgcaac gcggggaggc agacaaggta    5868
tagggcggcg cctacaatcc atgccaaccc gttccatgtg ctcgccgagg cggcataaat    5928
cgccgtgacg atcagcggtc caatgatcga agttaggctg gtaagagccg cgagcgatcc    5988
ttgaagctgt ccctgatggt cgtcatctac ctgcctggac agcatggcct gcaacgcggg    6048
catcccgatg ccgccggaag cgagaagaat cataatgggg aaggccatcc agcctcgcgt    6108
cgcgaacgcc agcaagacgt agcccagcgc gtcggccgcc atgccggcga taatggcctg    6168
cttctcgccg aaacgtttgg tggcgggacc agtgacgaag gcttgagcga gggcgtgcaa    6228
gattccgaat accgcaagcg acaggccgat catcgtcgcg ctccagcgaa agcggtcctc    6288
gccgaaaatg acccagagcg ctgccggcac ctgtcctacg agttgcatga taaagaagac    6348
agtcataagt gcggcgacga tagtcatgcc ccgcgcccac cggaaggagc tgactgggtt    6408
gaaggctctc aagggcatcg gtcgacgctc tcccttatgc gactcctgca ttaggaagca    6468
```

-continued

```
gcccagtagt aggttgaggc cgttgagcac cgccgccgca aggaatggtg catgcat        6525
```

<210> SEQ ID NO 2
<211> LENGTH: 725
<212> TYPE: PRT
<213> ORGANISM: Zymomonas mobilis

<400> SEQUENCE: 2

```
Met Gly Ile Asp Arg Met Asn Ser Leu Ser Arg Leu Leu Met Lys Lys
1               5                   10                  15

Ile Phe Gly Ala Glu Lys Thr Ser Tyr Lys Pro Ala Ser Asp Thr Ile
            20                  25                  30

Ile Gly Thr Asp Thr Leu Lys Arg Pro Asn Arg Arg Pro Glu Pro Thr
        35                  40                  45

Ala Lys Val Asp Lys Thr Ile Phe Lys Thr Met Gly Asn Ser Leu Asn
    50                  55                  60

Asn Thr Leu Val Ser Ala Cys Asp Trp Leu Ile Gly Gln Gln Lys Pro
65                  70                  75                  80

Asp Gly His Trp Val Gly Ala Val Glu Ser Asn Ala Ser Met Glu Ala
                85                  90                  95

Glu Trp Cys Leu Ala Leu Trp Phe Leu Gly Leu Glu Asp His Pro Leu
            100                 105                 110

Arg Pro Arg Leu Gly Asn Ala Leu Leu Glu Met Gln Arg Glu Asp Gly
        115                 120                 125

Ser Trp Gly Val Tyr Phe Gly Ala Gly Asn Gly Asp Ile Asn Ala Thr
    130                 135                 140

Val Glu Ala Tyr Ala Ala Leu Arg Ser Leu Gly Tyr Ser Ala Asp Asn
145                 150                 155                 160

Pro Val Leu Lys Lys Ala Ala Ala Trp Ile Ala Glu Lys Gly Gly Leu
                165                 170                 175

Lys Asn Ile Arg Val Phe Thr Arg Tyr Trp Leu Ala Leu Ile Gly Glu
            180                 185                 190

Trp Pro Trp Glu Lys Thr Pro Asn Leu Pro Pro Glu Ile Ile Trp Phe
        195                 200                 205

Pro Asp Asn Phe Val Phe Ser Ile Tyr Asn Phe Ala Gln Trp Ala Arg
    210                 215                 220

Ala Thr Met Val Pro Ile Ala Ile Leu Ser Ala Arg Arg Pro Ser Arg
225                 230                 235                 240

Pro Leu Arg Pro Gln Asp Arg Leu Asp Glu Leu Phe Pro Glu Gly Arg
                245                 250                 255

Ala Arg Phe Asp Tyr Glu Leu Pro Lys Lys Glu Gly Ile Asp Leu Trp
            260                 265                 270

Ser Gln Phe Phe Arg Thr Thr Asp Arg Gly Leu His Trp Val Gln Ser
        275                 280                 285

Asn Leu Leu Lys Arg Asn Ser Leu Arg Glu Ala Ala Ile Arg His Val
    290                 295                 300

Leu Glu Trp Ile Ile Arg His Gln Asp Ala Asp Gly Gly Trp Gly Gly
305                 310                 315                 320

Ile Gln Pro Pro Trp Val Tyr Gly Leu Met Ala Leu His Gly Glu Gly
                325                 330                 335

Tyr Gln Leu Tyr His Pro Val Met Ala Lys Ala Leu Ser Ala Leu Asp
            340                 345                 350

Asp Pro Gly Trp Arg His Asp Arg Gly Glu Ser Ser Trp Ile Gln Ala
        355                 360                 365
```

```
Thr Asn Ser Pro Val Trp Asp Thr Met Leu Ala Leu Met Ala Leu Lys
    370                 375                 380

Asp Ala Lys Ala Glu Asp Arg Phe Thr Pro Glu Met Asp Lys Ala Ala
385                 390                 395                 400

Asp Trp Leu Leu Ala Arg Gln Val Lys Val Lys Gly Asp Trp Ser Ile
                405                 410                 415

Lys Leu Pro Asp Val Glu Pro Gly Gly Trp Ala Phe Glu Tyr Ala Asn
                420                 425                 430

Asp Arg Tyr Pro Asp Thr Asp Thr Ala Val Ala Leu Ile Ala Leu
                435                 440                 445

Ser Ser Tyr Arg Asp Lys Glu Trp Gln Lys Lys Gly Val Glu Asp
    450                 455                 460

Ala Ile Thr Arg Gly Val Asn Trp Leu Ile Ala Met Gln Ser Glu Cys
465                 470                 475                 480

Gly Gly Trp Gly Ala Phe Asp Lys Asp Asn Asn Arg Ser Ile Leu Ser
                485                 490                 495

Lys Ile Pro Phe Cys Asp Phe Gly Glu Ser Ile Asp Pro Pro Ser Val
                500                 505                 510

Asp Val Thr Ala His Val Leu Glu Ala Phe Gly Thr Leu Gly Leu Ser
                515                 520                 525

Arg Asp Met Pro Val Ile Gln Lys Ala Ile Asp Tyr Val Arg Ser Glu
530                 535                 540

Gln Glu Ala Glu Gly Ala Trp Phe Gly Arg Trp Gly Val Asn Tyr Ile
545                 550                 555                 560

Tyr Gly Thr Gly Ala Val Leu Pro Ala Leu Ala Ala Ile Gly Glu Asp
                565                 570                 575

Met Thr Gln Pro Tyr Ile Thr Lys Ala Cys Asp Trp Leu Val Ala His
                580                 585                 590

Gln Gln Glu Asp Gly Gly Trp Gly Glu Ser Cys Ser Ser Tyr Met Glu
                595                 600                 605

Ile Asp Ser Ile Gly Lys Gly Pro Thr Thr Pro Ser Gln Thr Ala Trp
610                 615                 620

Ala Leu Met Gly Leu Ile Ala Ala Asn Arg Pro Glu Asp Tyr Glu Ala
625                 630                 635                 640

Ile Ala Lys Gly Cys His Tyr Leu Ile Asp Arg Gln Glu Gln Asp Gly
                645                 650                 655

Ser Trp Lys Glu Glu Glu Phe Thr Gly Thr Gly Phe Pro Gly Tyr Gly
                660                 665                 670

Val Gly Gln Thr Ile Lys Leu Asp Asp Pro Ala Leu Ser Lys Arg Leu
                675                 680                 685

Leu Gln Gly Ala Glu Leu Ser Arg Ala Phe Met Leu Arg Tyr Asp Phe
    690                 695                 700

Tyr Arg Gln Phe Phe Pro Ile Met Ala Leu Ser Arg Ala Glu Arg Leu
705                 710                 715                 720

Ile Asp Leu Asn Asn
                725

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
```
gcgctgtttc atatgggtat tgaca                                      25

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
gcgcttaccc tggatcctcg aaaat                                      25

<210> SEQ ID NO 5
<211> LENGTH: 684
<212> TYPE: PRT
<213> ORGANISM: Bradyrhizobium japonicum

<400> SEQUENCE: 5

```
Met Thr Val Thr Ser Ala Ser Ala Arg Ala Thr Arg Asp Pro Gly
1               5                   10                  15

Asn Tyr Gln Thr Ala Leu Gln Ser Thr Val Arg Ala Ala Asp Trp
                20                  25                  30

Leu Ile Ala Asn Gln Lys Pro Asp Gly His Trp Val Gly Arg Ala Glu
            35                  40                  45

Ser Asn Ala Cys Met Glu Ala Gln Trp Cys Leu Ala Leu Trp Phe Met
50                  55                  60

Gly Leu Glu Asp His Pro Leu Arg Lys Arg Leu Gly Gln Ser Leu Leu
65                  70                  75                  80

Asp Ser Gln Arg Pro Asp Gly Ala Trp Gln Val Tyr Phe Gly Ala Pro
                85                  90                  95

Asn Gly Asp Ile Asn Ala Thr Val Glu Ala Tyr Ala Ala Leu Arg Ser
            100                 105                 110

Leu Gly Phe Arg Asp Asp Glu Pro Ala Val Arg Arg Ala Arg Glu Trp
        115                 120                 125

Ile Glu Ala Lys Gly Gly Leu Arg Asn Ile Arg Val Phe Thr Arg Tyr
130                 135                 140

Trp Leu Ala Leu Ile Gly Glu Trp Pro Trp Glu Lys Thr Pro Asn Ile
145                 150                 155                 160

Pro Pro Glu Val Ile Trp Phe Pro Leu Trp Phe Pro Phe Ser Ile Tyr
                165                 170                 175

Asn Phe Ala Gln Trp Ala Arg Ala Thr Leu Met Pro Ile Ala Val Leu
            180                 185                 190

Ser Ala Arg Arg Pro Ser Arg Pro Leu Pro Glu Asn Arg Leu Asp
        195                 200                 205

Ala Leu Phe Pro His Gly Arg Lys Ala Phe Asp Tyr Glu Leu Pro Val
210                 215                 220

Lys Ala Gly Ala Gly Trp Asp Arg Phe Phe Arg Gly Ala Asp Lys
225                 230                 235                 240

Val Leu His Lys Leu Gln Asn Leu Gly Asn Arg Leu Asn Leu Gly Leu
                245                 250                 255

Phe Arg Pro Ala Ala Thr Ser Arg Val Leu Glu Trp Met Ile Arg His
            260                 265                 270

Gln Asp Phe Asp Gly Ala Trp Gly Gly Ile Gln Pro Pro Trp Ile Tyr
        275                 280                 285

Gly Leu Met Ala Leu Tyr Ala Glu Gly Tyr Pro Leu Asn His Pro Val
290                 295                 300
```

Leu Ala Lys Gly Leu Asp Ala Leu Asn Asp Pro Gly Trp Arg Val Asp
305                 310                 315                 320

Val Gly Asp Ala Thr Tyr Ile Gln Ala Thr Asn Ser Pro Val Trp Asp
            325                 330                 335

Thr Ile Leu Thr Leu Leu Ala Phe Asp Asp Ala Gly Val Leu Gly Asp
        340                 345                 350

Tyr Pro Glu Ala Val Asp Lys Ala Val Asp Trp Val Leu Gln Arg Gln
    355                 360                 365

Val Arg Val Pro Gly Asp Trp Ser Met Lys Leu Pro His Val Lys Pro
370                 375                 380

Gly Gly Trp Ala Phe Glu Tyr Ala Asn Asn Tyr Tyr Pro Asp Thr Asp
385                 390                 395                 400

Asp Thr Ala Val Ala Leu Ile Ala Leu Ala Pro Leu Arg His Asp Pro
                405                 410                 415

Lys Trp Lys Ala Lys Gly Ile Asp Glu Ala Ile Gln Leu Gly Val Asp
            420                 425                 430

Trp Leu Ile Gly Met Gln Ser Gln Gly Gly Trp Gly Ala Phe Asp
        435                 440                 445

Lys Asp Asn Asn Gln Lys Ile Leu Thr Lys Ile Pro Phe Cys Asp Tyr
450                 455                 460

Gly Glu Ala Leu Asp Pro Pro Ser Val Asp Val Thr Ala His Ile Ile
465                 470                 475                 480

Glu Ala Phe Gly Lys Leu Gly Ile Ser Arg Asn His Pro Ser Met Val
            485                 490                 495

Gln Ala Leu Asp Tyr Ile Arg Arg Glu Gln Pro Ser Gly Pro Trp
    500                 505                 510

Phe Gly Arg Trp Gly Val Asn Tyr Val Tyr Gly Thr Gly Ala Val Leu
            515                 520                 525

Pro Ala Leu Ala Ala Ile Gly Glu Asp Met Thr Gln Pro Tyr Ile Gly
530                 535                 540

Arg Ala Cys Asp Trp Leu Val Ala His Gln Gln Ala Asp Gly Gly Trp
545                 550                 555                 560

Gly Glu Ser Cys Ala Ser Tyr Met Asp Val Ser Ala Val Gly Arg Gly
                565                 570                 575

Thr Thr Thr Ala Ser Gln Thr Ala Trp Ala Leu Met Ala Leu Leu Ala
            580                 585                 590

Ala Asn Arg Pro Gln Asp Lys Asp Ala Ile Glu Arg Gly Cys Met Trp
        595                 600                 605

Leu Val Glu Arg Gln Ser Ala Gly Thr Trp Asp Glu Pro Glu Phe Thr
    610                 615                 620

Gly Thr Gly Phe Pro Gly Tyr Gly Val Gly Gln Thr Ile Lys Leu Asn
625                 630                 635                 640

Asp Pro Ala Leu Ser Gln Arg Leu Met Gln Gly Pro Glu Leu Ser Arg
                645                 650                 655

Ala Phe Met Leu Arg Tyr Gly Met Tyr Arg His Tyr Phe Pro Leu Met
            660                 665                 670

Ala Leu Gly Arg Ala Leu Arg Pro Gln Ser His Ser
        675                 680

<210> SEQ ID NO 6
<211> LENGTH: 657
<212> TYPE: PRT
<213> ORGANISM: Burkholderia ambifaria

<400> SEQUENCE: 6

```
Met Asn Asp Leu Thr Glu Met Ala Thr Leu Ser Ala Gly Thr Val Pro
1               5                   10                  15

Ala Gly Leu Asp Ala Ala Val Ala Ser Ala Thr Asp Ala Leu Leu Ala
            20                  25                  30

Ala Gln Asn Ala Asp Gly His Trp Val Tyr Glu Leu Glu Ala Asp Ser
        35                  40                  45

Thr Ile Pro Ala Glu Tyr Val Leu Leu Val His Tyr Leu Gly Glu Thr
    50                  55                  60

Pro Asn Leu Glu Leu Glu Gln Lys Ile Gly Arg Tyr Leu Arg Arg Val
65                  70                  75                  80

Gln Gln Ala Asp Gly Gly Trp Pro Leu Phe Thr Asp Gly Ala Pro Asn
                85                  90                  95

Ile Ser Ala Ser Val Lys Ala Tyr Phe Ala Leu Lys Val Ile Gly Asp
            100                 105                 110

Asp Glu Asn Ala Glu His Met Gln Arg Ala Arg Arg Ala Ile Gln Ala
        115                 120                 125

Met Gly Gly Ala Glu Met Ser Asn Val Phe Thr Arg Ile Gln Leu Ala
130                 135                 140

Leu Tyr Gly Ala Ile Pro Trp Arg Ala Val Pro Met Met Pro Val Glu
145                 150                 155                 160

Ile Met Leu Leu Pro Gln Trp Phe Pro Phe His Leu Ser Lys Val Ser
                165                 170                 175

Tyr Trp Ala Arg Thr Val Ile Val Pro Leu Leu Val Leu Asn Ala Lys
            180                 185                 190

Arg Pro Ile Ala Lys Asn Pro Arg Gly Val Arg Ile Asp Glu Leu Phe
        195                 200                 205

Val Asp Pro Pro Val Asn Ala Gly Leu Leu Pro Arg Gln Gly His Gln
    210                 215                 220

Ser Pro Gly Trp Phe Ala Phe Phe Arg Val Val Asp His Ala Leu Arg
225                 230                 235                 240

Ala Ala Asp Gly Leu Phe Pro Asn Tyr Thr Arg Glu Arg Ala Ile Arg
                245                 250                 255

Gln Ala Val Ser Phe Val Asp Glu Arg Leu Asn Gly Glu Asp Gly Leu
            260                 265                 270

Gly Ala Ile Tyr Pro Ala Met Ala Asn Ala Val Met Met Tyr Asp Val
        275                 280                 285

Leu Gly Tyr Ala Glu Asp His Pro Asn Arg Ala Ile Ala Arg Lys Ser
    290                 295                 300

Ile Glu Lys Leu Leu Val Val Gln Glu Asp Glu Ala Tyr Cys Gln Pro
305                 310                 315                 320

Cys Leu Ser Pro Val Trp Asp Thr Ser Leu Ala His Ala Leu Leu
                325                 330                 335

Glu Thr Gly Asp Ala Arg Ala Glu Glu Ala Val Ile Arg Gly Leu Glu
            340                 345                 350

Trp Leu Arg Pro Leu Gln Ile Leu Asp Val Arg Gly Asp Trp Ile Ser
        355                 360                 365

Arg Arg Pro His Val Arg Pro Gly Gly Trp Ala Phe Gln Tyr Ala Asn
    370                 375                 380

Pro His Tyr Pro Asp Val Asp Thr Ala Val Val Ala Val Ala Met
385                 390                 395                 400

Asp Arg Val Gln Lys Leu Lys His Asn Asp Ala Phe Arg Asp Ser Ile
                405                 410                 415
```

Ala Arg Ala Arg Glu Trp Val Val Gly Met Gln Ser Ser Asp Gly Gly
            420                 425                 430

Trp Gly Ala Phe Glu Pro Glu Asn Thr Gln Tyr Tyr Leu Asn Asn Ile
            435                 440                 445

Pro Phe Ser Asp His Gly Ala Leu Leu Asp Pro Thr Ala Asp Val
450                 455                 460

Ser Gly Arg Cys Leu Ser Met Leu Ala Gln Leu Gly Glu Thr Pro Leu
465                 470                 475                 480

Asn Ser Glu Pro Ala Arg Arg Ala Leu Asp Tyr Met Leu Lys Glu Gln
            485                 490                 495

Glu Pro Asp Gly Ser Trp Tyr Gly Arg Trp Gly Met Asn Tyr Val Tyr
            500                 505                 510

Gly Thr Trp Thr Ala Leu Cys Ala Leu Asn Ala Ala Gly Leu Thr Pro
            515                 520                 525

Asp Asp Pro Arg Val Lys Arg Gly Ala Gln Trp Leu Leu Ser Ile Gln
530                 535                 540

Asn Lys Asp Gly Gly Trp Gly Glu Asp Gly Asp Ser Tyr Lys Leu Asn
545                 550                 555                 560

Tyr Arg Gly Phe Glu Gln Ala Pro Ser Thr Ala Ser Gln Thr Ala Trp
            565                 570                 575

Ala Leu Leu Gly Leu Met Ala Ala Gly Glu Val Asn Asn Pro Ala Val
            580                 585                 590

Ala Arg Gly Val Glu Tyr Leu Ile Ala Glu Gln Lys Glu His Gly Leu
            595                 600                 605

Trp Asp Glu Thr Arg Phe Thr Ala Thr Gly Phe Pro Arg Val Phe Tyr
610                 615                 620

Leu Arg Tyr His Gly Tyr Arg Lys Phe Phe Pro Leu Trp Ala Leu Ala
625                 630                 635                 640

Arg Tyr Arg Asn Leu Lys Arg Asn Asn Ala Thr Arg Val Thr Phe Gly
            645                 650                 655

Leu

<210> SEQ ID NO 7
<211> LENGTH: 682
<212> TYPE: PRT
<213> ORGANISM: Burkholderia ambifaria

<400> SEQUENCE: 7

Met Ile Arg Arg Met Asn Lys Ser Gly Pro Ser Pro Trp Ser Ala Leu
1               5                   10                  15

Asp Ala Ala Ile Ala Arg Gly Arg Asp Ala Leu Met Arg Leu Gln Gln
            20                  25                  30

Pro Asp Gly Ser Trp Cys Phe Glu Leu Glu Ser Asp Ala Thr Ile Thr
            35                  40                  45

Ala Glu Tyr Ile Leu Met Met His Phe Met Asp Lys Ile Asp Asp Ala
            50                  55                  60

Arg Gln Glu Lys Met Ala Arg Tyr Leu Arg Ala Ile Gln Arg Leu Asp
65                  70                  75                  80

Thr His Gly Gly Trp Asp Leu Tyr Val Asp Gly Pro Asp Val Ser
            85                  90                  95

Cys Ser Val Lys Ala Tyr Phe Ala Leu Lys Ala Ala Gly Asp Ser Glu
            100                 105                 110

His Ala Pro His Met Val Arg Ala Arg Asp Ala Ile Leu Glu Leu Gly
            115                 120                 125

```
Gly Ala Ala Arg Ser Asn Val Phe Thr Arg Ile Leu Leu Ala Thr Phe
    130                 135                 140

Gly Gln Val Pro Trp Arg Ala Thr Pro Phe Met Pro Ile Glu Phe Val
145                 150                 155                 160

Leu Phe Pro Lys Trp Val Pro Ile Ser Met Tyr Lys Val Ala Tyr Trp
                165                 170                 175

Ala Arg Thr Thr Met Val Pro Leu Leu Val Leu Cys Ser Leu Lys Ala
            180                 185                 190

Arg Ala Arg Asn Pro Arg Asn Ile Ala Ile Pro Glu Leu Phe Val Thr
        195                 200                 205

Pro Pro Asp Gln Glu Arg Gln Tyr Phe Pro Ala Arg Gly Met Arg
210                 215                 220

Arg Ala Phe Leu Ala Leu Asp Arg Val Arg His Val Glu Pro Leu
225                 230                 235                 240

Leu Pro Lys Arg Leu Arg Gln Arg Ala Ile Arg His Ala Gln Ala Trp
                245                 250                 255

Cys Ala Glu Arg Met Asn Gly Glu Asp Gly Leu Gly Gly Ile Phe Pro
            260                 265                 270

Pro Ile Val Tyr Ser Tyr Gln Met Met Asp Val Leu Gly Tyr Pro Asp
        275                 280                 285

Asp His Pro Leu Arg Arg Asp Cys Glu Asn Ala Leu Glu Lys Leu Leu
290                 295                 300

Val Thr Arg Pro Asp Gly Ser Met Tyr Cys Gln Pro Cys Leu Ser Pro
305                 310                 315                 320

Val Trp Asp Thr Ala Trp Ser Thr Met Ala Leu Glu Gln Ala Arg Gly
                325                 330                 335

Val Ala Val Pro Glu Ala Gly Ala Pro Ala Ser Ala Leu Asp Glu Leu
            340                 345                 350

Asp Ala Arg Ile Ala Arg Ala Tyr Asp Trp Leu Ala Glu Arg Gln Val
        355                 360                 365

Asn Asp Leu Arg Gly Asp Trp Ile Glu Asn Ala Pro Ala Asp Thr Gln
370                 375                 380

Pro Gly Gly Trp Ala Phe Gln Tyr Ala Asn Pro Tyr Tyr Pro Asp Ile
385                 390                 395                 400

Asp Asp Ser Ala Val Val Thr Ala Met Leu Asp Arg Arg Gly Arg Thr
                405                 410                 415

His Arg Asn Ala Asp Gly Ser His Pro Tyr Ala Ala Arg Val Ala Arg
            420                 425                 430

Ala Leu Asp Trp Met Arg Gly Leu Gln Ser Arg Asn Gly Gly Phe Ala
        435                 440                 445

Ala Phe Asp Ala Asp Cys Asp Arg Leu Tyr Leu Asn Ala Ile Pro Phe
450                 455                 460

Ala Asp His Gly Ala Leu Leu Asp Pro Pro Thr Glu Asp Val Ser Gly
465                 470                 475                 480

Arg Val Leu Leu Cys Phe Gly Val Thr Lys Arg Ala Asp Asp Arg Ala
                485                 490                 495

Ser Leu Ala Arg Ala Ile Asp Tyr Val Lys Arg Thr Gln Pro Asp
            500                 505                 510

Gly Ser Trp Trp Gly Arg Trp Gly Thr Asn Tyr Leu Tyr Gly Thr Trp
        515                 520                 525

Ser Val Leu Ala Gly Leu Ala Leu Ala Gly Glu Asp Pro Ser Gln Pro
530                 535                 540
```

Tyr Ile Ala Arg Ala Leu Ala Trp Leu Arg Ala Arg Gln His Ala Asp
545                 550                 555                 560

Gly Gly Trp Gly Glu Thr Asn Asp Ser Tyr Ile Asp Pro Ala Leu Ala
                565                 570                 575

Gly Thr Asn Ala Gly Glu Ser Thr Ser Asn Cys Thr Ala Trp Ala Leu
            580                 585                 590

Leu Ala Gln Met Ala Phe Gly Asp Gly Glu Ser Glu Ser Val Arg Arg
        595                 600                 605

Gly Ile Ala Tyr Leu Gln Ser Val Gln Gln Asp Asp Gly Phe Trp Trp
    610                 615                 620

His Arg Ser His Asn Ala Pro Gly Phe Pro Arg Ile Phe Tyr Leu Lys
625                 630                 635                 640

Tyr His Gly Tyr Thr Ala Tyr Phe Pro Leu Trp Ala Leu Ala Arg Tyr
                645                 650                 655

Arg Arg Leu Ala Gly Gly Val Ser Ala Ala Gly Ala His Ala Val Pro
            660                 665                 670

Ala Ser Thr Gly Ala Asp Ala Ala Leu Ala
            675                 680

<210> SEQ ID NO 8
<211> LENGTH: 617
<212> TYPE: PRT
<213> ORGANISM: Bacillus anthracis

<400> SEQUENCE: 8

Met Leu Leu Tyr Glu Lys Ala His Glu Glu Ile Val Arg Arg Ala Thr
1               5                   10                  15

Ala Leu Gln Thr Met Gln Trp Gln Asp Gly Thr Trp Arg Phe Cys Phe
            20                  25                  30

Glu Gly Ala Pro Leu Thr Asp Cys His Met Ile Phe Leu Leu Lys Leu
        35                  40                  45

Leu Gly Arg Asp Lys Glu Ile Glu Pro Phe Val Glu Arg Val Ala Ser
    50                  55                  60

Leu Gln Thr Asn Glu Gly Thr Trp Lys Leu His Glu Asp Glu Val Gly
65                  70                  75                  80

Gly Asn Leu Ser Ala Thr Ile Gln Ser Tyr Ala Ala Leu Leu Ala Ser
                85                  90                  95

Lys Lys Tyr Thr Lys Glu Asp Ala Asn Met Lys Arg Ala Glu Asn Phe
            100                 105                 110

Ile Gln Glu Arg Gly Gly Val Ala Arg Ala His Phe Met Thr Lys Phe
        115                 120                 125

Leu Leu Ala Ile His Gly Glu Tyr Glu Tyr Pro Ser Leu Phe His Leu
    130                 135                 140

Pro Thr Pro Ile Met Phe Leu Gln Asn Asp Ser Pro Phe Ser Ile Phe
145                 150                 155                 160

Glu Leu Ser Ser Ser Ala Arg Ile His Leu Ile Pro Met Met Leu Cys
                165                 170                 175

Leu Asn Lys Arg Phe Arg Val Gly Lys Lys Leu Leu Pro Asn Leu Asn
            180                 185                 190

His Ile Ala Gly Gly Gly Glu Trp Phe Arg Glu Asp Arg Ser Pro
        195                 200                 205

Val Phe Gln Thr Leu Leu Ser Asp Val Lys Gln Ile Ile Ser Tyr Pro
    210                 215                 220

Leu Ser Leu His His Lys Gly Tyr Glu Glu Ile Glu Arg Phe Met Lys
225                 230                 235                 240

Glu Arg Ile Asp Glu Asn Gly Thr Leu Tyr Ser Tyr Ala Thr Ala Ser
              245                 250                 255

Phe Tyr Met Ile Tyr Ala Leu Leu Ala Leu Gly His Ser Leu Gln Ser
        260                 265                 270

Ser Met Ile Gln Lys Ala Ile Ala Gly Ile Thr Ser Tyr Ile Trp Lys
    275                 280                 285

Met Glu Arg Gly Asn His Leu Gln Asn Ser Pro Ser Thr Val Trp Asp
290                 295                 300

Thr Ala Leu Leu Ser Tyr Ala Leu Gln Glu Ala Gln Val Ser Lys Asp
305                 310                 315                 320

Asn Lys Met Ile Gln Asn Ala Thr Ala Tyr Leu Leu Lys Lys Gln His
                325                 330                 335

Thr Lys Lys Ala Asp Trp Ser Val His Ala Pro Ala Leu Thr Pro Gly
            340                 345                 350

Gly Trp Gly Phe Ser Asp Val Asn Thr Thr Ile Pro Asp Ile Asp Asp
        355                 360                 365

Thr Thr Ala Val Leu Arg Ala Leu Ala Arg Ser Arg Gly Asn Lys Asn
370                 375                 380

Ile Asp Asn Ala Trp Lys Lys Gly Gly Asn Trp Ile Lys Gly Leu Gln
385                 390                 395                 400

Asn Asn Asp Gly Gly Trp Gly Ala Phe Glu Lys Gly Val Thr Ser Lys
                405                 410                 415

Leu Leu Ala Lys Leu Pro Ile Glu Asn Ala Ser Asp Met Ile Thr Asp
            420                 425                 430

Pro Ser Thr Pro Asp Ile Thr Gly Arg Val Leu Glu Phe Phe Gly Thr
        435                 440                 445

Tyr Ala Gln Asn Glu Leu Pro Glu Lys Gln Ile Gln Arg Ala Ile Asn
450                 455                 460

Trp Leu Met Asn Val Gln Glu Glu Asn Gly Ser Trp Tyr Gly Lys Trp
465                 470                 475                 480

Gly Ile Cys Tyr Leu Tyr Gly Thr Trp Ala Val Met Thr Gly Leu Arg
                485                 490                 495

Ser Leu Gly Ile Pro Ser Ser Asn Pro Ser Leu Thr Arg Ala Ala Ser
            500                 505                 510

Trp Leu Glu His Ile Gln His Glu Asp Gly Gly Trp Gly Glu Ser Cys
        515                 520                 525

His Ser Ser Val Glu Lys Arg Phe Val Thr Leu Pro Phe Ser Thr Pro
530                 535                 540

Ser Gln Thr Ala Trp Ala Leu Asp Ala Leu Ile Ser Tyr Tyr Asp Thr
545                 550                 555                 560

Glu Thr Pro Ala Ile Arg Lys Gly Val Ser Tyr Leu Leu Ser Asn Pro
                565                 570                 575

Tyr Val Asn Glu Arg Tyr Pro Thr Gly Thr Gly Leu Pro Gly Ala Phe
            580                 585                 590

Tyr Ile Arg Tyr His Ser Tyr Ala His Ile Tyr Pro Leu Leu Thr Leu
        595                 600                 605

Ala His Tyr Ile Lys Lys Tyr Arg Lys
610                 615

<210> SEQ ID NO 9
<211> LENGTH: 720
<212> TYPE: PRT
<213> ORGANISM: Frankia alni

<400> SEQUENCE: 9

```
Met Pro Ala Gly Val Gly Val Leu Val Trp Leu Asp Gln Arg Leu Arg
1               5                   10                  15
Ala Met Gly Arg Pro Asp Leu Val Thr Thr Thr Gly Gly Ala Glu Ile
            20                  25                  30
Pro Phe Val Leu Val Ala Ala Thr Ala Ser Thr Val Gly Val Ala Leu
        35                  40                  45
Ala Leu Arg Arg Pro Arg His Pro Val Gly Trp Leu Phe Leu Ala Leu
    50                  55                  60
Gly Gly Val Leu Leu Ser Gly Gly Thr Gln Gly Tyr Ala Ala Tyr
65                  70                  75                  80
Gly Ala Val Ala Arg Pro Gly Arg Leu Pro Ala Ala Asp Leu Val Ala
                85                  90                  95
Ile Tyr Ala Asp Ala Gly Phe Ile Pro Trp Leu Val Leu Val Ala Leu
            100                 105                 110
Ile Leu His Leu Thr Pro Thr Gly Arg Pro Leu Ser Ala Arg Trp Gly
        115                 120                 125
Arg Ile Ala Leu Ala Thr Ala Val Ala Gly Gly Leu Trp Leu Leu Val
    130                 135                 140
Gly Leu Val Thr Thr Glu Thr Met Gln Pro Pro Phe Gln Ser Val Thr
145                 150                 155                 160
Asn Pro Leu Leu Ile Gly Gly Pro Leu Gly Pro Leu Val Ala Arg
                165                 170                 175
Arg Val Leu Gly Leu Ala Thr Gly Ala Gly Val Val Leu Ala Ala Val
            180                 185                 190
Ser Leu Ile Val Arg Phe Arg Arg Ser Val Asp Val Glu Arg Arg Gln
        195                 200                 205
Leu Leu Trp Val Ala Val Ala Val Pro Leu Pro Val Leu Met Ala
    210                 215                 220
Ala Ser Phe Ala Ala Ser Tyr Ala Gly Asn Asn Thr Ala Ala Gly Leu
225                 230                 235                 240
Ala Ala Ala Thr Leu Ile Gly Leu Leu Ala Ile Gly Ala Gly Leu Ala
                245                 250                 255
Ile Gly Gln Tyr His Leu Tyr Asp Val Glu Glu Ile Leu Ser Arg Ala
            260                 265                 270
Val Thr Tyr Leu Leu Val Ser Gly Leu Leu Ala Ala Ser Tyr Ala Thr
        275                 280                 285
Val Val Ile Val Val Gly Gln Ser Leu Ala Gly Arg Thr Gly Arg Ser
    290                 295                 300
Gln Ile Ser Ala Val Leu Ala Thr Leu Ala Ala Val Ala Val Thr Ala
305                 310                 315                 320
Pro Ala Tyr Arg Lys Ile Gln Glu Gly Val Asp Arg Arg Phe Ser Arg
                325                 330                 335
Arg Arg Phe Glu Thr Leu Gln Val Ile Arg Arg Tyr Leu Arg Asp Pro
            340                 345                 350
Asp Pro Asp Val Ala Val Glu Glu Val Leu Arg Arg Ala Leu Gly Asp
        355                 360                 365
Pro Thr Leu Ala Val Ala Tyr Leu Val Asp Asp Arg Arg Gln Trp Val
    370                 375                 380
Ser Ala Asp Gly Gln Pro Ala Asn Pro Gly Asn Ser Phe Met Ala Ala
385                 390                 395                 400
Val Glu Val Tyr Arg Arg Gly Arg Pro Ile Ala Arg Val Thr Phe Asp
                405                 410                 415
```

Arg Gly Arg Ala Gln Pro Gly Leu Val Arg Ala Ala Thr Ala Ala
            420                 425                 430

Thr Ala Glu Leu Asp Asn Ala Gly Leu Arg Ala Val Ala Leu Gln
        435                 440                 445

Leu Val Glu Val Arg Gln Ser Arg Thr Arg Ile Ala Ala Gln Phe
450                 455                 460

Ala Glu Arg Arg Thr Ile Glu Arg Asn Leu His Asp Gly Ala Gln Gln
465                 470                 475                 480

Arg Leu Leu Ala Leu Ala Leu Gln Leu Arg Ala Val Gln Leu Gly Gly
                485                 490                 495

Asp Glu Ala Ser Leu Arg Gln Ala Ile Ser Thr Gly Ile Asp Gln Leu
            500                 505                 510

Gln Ala Ala Val Val Glu Leu Arg Glu Leu Ala Asn Gly Leu His Pro
        515                 520                 525

Ala Val Leu Ala Asp Gly Gly Leu Ala Ala Leu Asp Asp Val Ala
530                 535                 540

Ala Arg Thr Pro Val Pro Ile Lys Ile Ser Ala Pro Asp Arg Arg Tyr
545                 550                 555                 560

Pro Pro Asp Leu Glu Ala Ala Trp Phe Ile Ala Cys Glu Ala Met
                565                 570                 575

Ala Asn Ala Val Lys His Ala His Pro Thr Thr Ile Ala Val Asp Val
            580                 585                 590

Ser Ala Pro Asp Gly Gln Leu Ile Val Glu Val Arg Asp Asp Gly Ile
        595                 600                 605

Gly Gly Ala Gln Pro Ser Gly Pro Gly Leu Arg Gly Ile Ala Asp Arg
    610                 615                 620

Ala Glu Ala Phe Gly Gly Ser Leu Thr Val His Thr Asp Pro Gly Thr
625                 630                 635                 640

Gly Thr Thr Ile Arg Ala Leu Leu His Arg Arg Ser Pro Leu Ser Ser
                645                 650                 655

Gly Arg Arg Ser Val Met Ile Glu Gly Cys Val Asp Val Val Ala Val
            660                 665                 670

Arg Arg Phe Arg Cys Arg Ser Ser Arg Gly Ser Gly Ser Arg Arg Arg
        675                 680                 685

Arg Ser Ser Trp Arg Cys Gly Gly Ile Cys Gly Ser Arg Cys Arg Thr
690                 695                 700

Gly Met Ser Arg Ser Cys Ser Arg Asn Ala Ala Ser Lys Leu Ile Thr
705                 710                 715                 720

<210> SEQ ID NO 10
<211> LENGTH: 685
<212> TYPE: PRT
<213> ORGANISM: Rhodopseudomonas palent

<400> SEQUENCE: 10

Met Asp Ser Ile Leu Ala Pro Arg Ala Asp Ala Pro Arg Asn Ile Asp
1               5                   10                  15

Gly Ala Leu Arg Glu Ser Val Gln Gln Ala Ala Asp Trp Leu Val Ala
                20                  25                  30

Asn Gln Lys Pro Asp Gly His Trp Val Gly Arg Ala Glu Thr Asn Ala
            35                  40                  45

Thr Met Glu Ala Gln Trp Cys Leu Ala Leu Trp Phe Leu Gly Leu Glu
        50                  55                  60

Asp His Pro Leu Arg Val Arg Leu Gly Arg Ala Leu Leu Asp Thr Gln

```
            65                  70                  75                  80
        Arg Pro Asp Gly Ala Trp His Val Phe Tyr Gly Ala Pro Asn Gly Asp
                        85                  90                  95
        Ile Asn Ala Thr Val Glu Ala Tyr Ala Leu Arg Ser Leu Gly His
                       100                 105                 110
        Arg Asp Glu Glu Pro Leu Arg Lys Ala Arg Asp Trp Ile Leu Ser
                       115                 120                 125
        Lys Gly Gly Leu Ala Asn Ile Arg Val Phe Thr Arg Tyr Trp Leu Ala
                       130                 135                 140
        Leu Ile Gly Glu Trp Pro Trp Glu Lys Thr Pro Asn Ile Leu Pro Glu
        145                 150                 155                 160
        Val Ile Trp Leu Pro Thr Trp Phe Pro Phe Ser Ile Tyr Asn Phe Ala
                           165                 170                 175
        Gln Trp Ala Arg Ala Thr Leu Met Pro Ile Ala Val Leu Ser Ala His
                       180                 185                 190
        Arg Pro Ser Arg Pro Leu Ala Pro Gln Asp Arg Leu Asp Ala Leu Phe
                       195                 200                 205
        Pro Gln Gly Arg Asp Ser Phe Asn Tyr Asp Leu Pro Ala Arg Leu Gly
                       210                 215                 220
        Ala Gly Val Trp Asp Val Ile Phe Arg Lys Ile Asp Thr Ile Leu His
        225                 230                 235                 240
        Arg Leu Gln Asp Trp Gly Ala Arg Arg Gly Pro His Gly Ile Met Arg
                       245                 250                 255
        Arg Gly Ala Ile Asp His Val Leu Gln Trp Ile Ile Arg His Gln Asp
                       260                 265                 270
        Tyr Asp Gly Ser Trp Gly Gly Ile Gln Pro Pro Trp Ile Tyr Gly Leu
                       275                 280                 285
        Met Ala Leu His Thr Glu Gly Tyr Ala Met Thr His Pro Val Met Ala
                       290                 295                 300
        Lys Ala Leu Asp Ala Leu Asn Glu Pro Gly Trp Arg Ile Asp Ile Gly
        305                 310                 315                 320
        Asp Ala Thr Phe Ile Gln Ala Thr Asn Ser Pro Val Trp Asp Thr Met
                       325                 330                 335
        Leu Ser Leu Leu Ala Phe Asp Asp Ala Gly Leu Gly Glu Arg Tyr Pro
                       340                 345                 350
        Glu Gln Val Glu Arg Ala Val Arg Trp Val Leu Lys Arg Gln Val Leu
                       355                 360                 365
        Val Pro Gly Asp Trp Ser Val Lys Leu Pro Asp Val Lys Pro Gly Gly
                       370                 375                 380
        Trp Ala Phe Glu Tyr Ala Asn Asn Phe Tyr Pro Asp Thr Asp Thr
        385                 390                 395                 400
        Ser Val Ala Leu Met Ala Leu Ala Pro Phe Arg His Asp Pro Lys Trp
                       405                 410                 415
        Gln Ala Glu Gly Ile Glu Asp Ala Ile Gln Arg Gly Ile Asp Trp Leu
                       420                 425                 430
        Val Ala Met Gln Cys Lys Glu Gly Gly Trp Gly Ala Phe Asp Lys Asp
                       435                 440                 445
        Asn Asp Lys Lys Ile Leu Ala Lys Ile Pro Phe Cys Asp Phe Gly Glu
                       450                 455                 460
        Ala Leu Asp Pro Pro Ser Ala Asp Val Thr Ala His Ile Ile Glu Ala
        465                 470                 475                 480
        Phe Ala Lys Val Gly Leu Asp Arg Asn His Pro Ser Ile Val Arg Ala
                       485                 490                 495
```

Leu Asp Tyr Leu Lys Arg Glu Gln Glu Pro Glu Gly Pro Trp Phe Gly
                500                 505                 510

Arg Trp Gly Val Asn Tyr Val Tyr Gly Thr Gly Ala Val Leu Pro Ala
            515                 520                 525

Leu Ala Ala Ile Gly Glu Asp Met Arg Gln Pro Tyr Ile Ala Arg Ala
        530                 535                 540

Cys Asp Trp Leu Ile Ala Arg Gln Gln Ala Asn Gly Gly Trp Gly Glu
545                 550                 555                 560

Ser Cys Val Ser Tyr Met Asp Ala Lys Gln Ala Gly Glu Gly Thr Ala
                565                 570                 575

Thr Ala Ser Gln Thr Ala Trp Ala Leu Met Ala Leu Ile Ala Ala Asp
            580                 585                 590

Arg Pro Gln Asp Arg Asp Ala Ile Glu Arg Gly Cys Leu Tyr Leu Thr
        595                 600                 605

Glu Thr Gln Arg Asp Gly Thr Trp Gln Glu Val His Tyr Thr Gly Thr
    610                 615                 620

Gly Phe Pro Gly Tyr Gly Val Gly Gln Thr Ile Lys Leu Asn Asp Pro
625                 630                 635                 640

Leu Leu Ser Lys Arg Leu Met Gln Gly Pro Glu Leu Ser Arg Ser Phe
                645                 650                 655

Met Leu Arg Tyr Asp Leu Tyr Arg His Tyr Phe Pro Met Met Ala Ile
            660                 665                 670

Gly Arg Val Leu Arg Gln Arg Gly Asp Arg Ser Gly His
        675                 680                 685

<210> SEQ ID NO 11
<211> LENGTH: 680
<212> TYPE: PRT
<213> ORGANISM: Streptomyces coelicolor

<400> SEQUENCE: 11

Met Thr Ala Thr Thr Asp Gly Ser Thr Gly Ala Ser Leu Arg Pro Leu
1               5                   10                  15

Ala Ala Ser Ala Ser Asp Thr Asp Ile Thr Ile Pro Ala Ala Ala Ala
            20                  25                  30

Gly Val Pro Glu Ala Ala Ala Arg Ala Thr Arg Arg Ala Thr Asp Phe
        35                  40                  45

Leu Leu Ala Lys Gln Asp Ala Glu Gly Trp Trp Lys Gly Asp Leu Glu
    50                  55                  60

Thr Asn Val Thr Met Asp Ala Glu Asp Leu Leu Leu Arg Gln Phe Leu
65                  70                  75                  80

Gly Ile Gln Asp Glu Glu Thr Thr Arg Ala Ala Ala Leu Phe Ile Arg
                85                  90                  95

Gly Glu Gln Arg Glu Asp Gly Thr Trp Ala Thr Phe Tyr Gly Gly Pro
            100                 105                 110

Gly Glu Leu Ser Thr Thr Ile Glu Ala Tyr Val Ala Leu Arg Leu Ala
        115                 120                 125

Gly Asp Ser Pro Glu Ala Pro His Met Ala Arg Ala Ala Glu Trp Ile
    130                 135                 140

Arg Ser Arg Gly Gly Ile Ala Ser Ala Arg Val Phe Thr Arg Ile Trp
145                 150                 155                 160

Leu Ala Leu Phe Gly Trp Trp Lys Trp Asp Asp Leu Pro Glu Leu Pro
                165                 170                 175

Pro Glu Leu Ile Tyr Phe Pro Thr Trp Val Pro Leu Asn Ile Tyr Asp

-continued

```
                180                 185                 190
Phe Gly Cys Trp Ala Arg Gln Thr Ile Val Pro Leu Thr Ile Val Ser
            195                 200                 205
Ala Lys Arg Pro Val Arg Pro Ala Pro Phe Pro Leu Asp Glu Leu His
            210                 215                 220
Thr Asp Pro Ala Arg Pro Asn Pro Pro Arg Pro Leu Ala Pro Val Ala
225                 230                 235                 240
Ser Trp Asp Gly Ala Phe Gln Arg Ile Asp Lys Ala Leu His Ala Tyr
                245                 250                 255
Arg Lys Val Ala Pro Arg Arg Leu Arg Arg Ala Ala Met Asn Ser Ala
            260                 265                 270
Ala Arg Trp Ile Ile Glu Arg Gln Glu Asn Asp Gly Cys Trp Gly Gly
            275                 280                 285
Ile Gln Pro Pro Ala Val Tyr Ser Val Ile Ala Leu Tyr Leu Leu Gly
            290                 295                 300
Tyr Asp Leu Glu His Pro Val Met Arg Ala Gly Leu Glu Ser Leu Asp
305                 310                 315                 320
Arg Phe Ala Val Trp Arg Glu Asp Gly Ala Arg Met Ile Glu Ala Cys
                325                 330                 335
Gln Ser Pro Val Trp Asp Thr Cys Leu Ala Thr Ile Ala Leu Ala Asp
            340                 345                 350
Ala Gly Val Pro Glu Asp His Pro Gln Leu Val Lys Ala Ser Asp Trp
            355                 360                 365
Met Leu Gly Glu Gln Ile Val Arg Pro Gly Asp Trp Ser Val Lys Arg
    370                 375                 380
Pro Gly Leu Pro Pro Gly Gly Trp Ala Phe Glu Phe His Asn Asp Asn
385                 390                 395                 400
Tyr Pro Asp Ile Asp Asp Thr Ala Glu Val Val Leu Ala Leu Arg Arg
                405                 410                 415
Val Arg His His Asp Pro Glu Arg Val Glu Lys Ala Ile Gly Arg Gly
            420                 425                 430
Val Arg Trp Asn Leu Gly Met Gln Ser Lys Asn Gly Ala Trp Gly Ala
            435                 440                 445
Phe Asp Val Asp Asn Thr Ser Ala Phe Pro Asn Arg Leu Pro Phe Cys
            450                 455                 460
Asp Phe Gly Glu Val Ile Asp Pro Pro Ser Ala Asp Val Thr Ala His
465                 470                 475                 480
Val Val Glu Met Leu Ala Val Glu Gly Leu Ala His Asp Pro Arg Thr
                485                 490                 495
Arg Arg Gly Ile Gln Trp Leu Leu Asp Ala Gln Glu Thr Asp Gly Ser
            500                 505                 510
Trp Phe Gly Arg Trp Gly Val Asn Tyr Val Tyr Gly Thr Gly Ser Val
            515                 520                 525
Ile Pro Ala Leu Thr Ala Ala Gly Leu Pro Thr Ser His Pro Ala Ile
            530                 535                 540
Arg Arg Ala Val Arg Trp Leu Glu Ser Val Gln Asn Glu Asp Gly Gly
545                 550                 555                 560
Trp Gly Glu Asp Leu Arg Ser Tyr Arg Tyr Val Arg Gly Trp Ser Gly
                565                 570                 575
Arg Gly Ala Ser Thr Ala Ser Gln Thr Gly Trp Ala Leu Met Ala Leu
            580                 585                 590
Leu Ala Ala Gly Glu Arg Asp Ser Lys Ala Val Glu Arg Gly Val Ala
            595                 600                 605
```

-continued

```
Trp Leu Ala Ala Thr Gln Arg Glu Asp Gly Ser Trp Asp Glu Pro Tyr
        610             615             620

Phe Thr Gly Thr Gly Phe Pro Trp Asp Phe Ser Ile Asn Tyr Asn Leu
625             630             635             640

Tyr Arg Gln Val Phe Pro Leu Thr Ala Leu Gly Arg Tyr Val His Gly
                645             650             655

Glu Pro Phe Ala Lys Lys Pro Arg Ala Ala Asp Ala Pro Ala Glu Ala
        660             665             670

Ala Pro Ala Glu Val Lys Gly Ser
        675             680
```

PROCESS FOR THE PREPARATION OF UNSATURATED CARBOXYLIC ACIDS BY CARBONYLATION OF ALLYL ALCOHOLS AND THEIR ACYLATION PRODUCTS

CROSS-REFERENCE TO RELATED APPLICATIONS

This application is a national stage application (under 35 U.S.C. § 371) of PCT/EP2018/053535, filed Feb. 13, 2018, which claims benefit of European Application No. 17157950.1, filed Feb. 24, 2017, both of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jan. 28, 2021, 2021, is named 074012-0409-US-592346-SL.txt and is 64,063 bytes in size.

BACKGROUND OF THE INVENTION

The present invention relates to a process for carbonylating allyl alcohols at low temperature, low pressure and/or low catalyst loading. In an alternative embodiment, an acylation product of the allyl alcohol is used for the carbonylation. The present invention also relates to the preparation of conversion products of these carbonylation products and specifically of (−)-ambrox.

STATE OF THE ART

The carbonylation products of allyl alcohols are valuable intermediates for preparation of a multitude of commercial products. By carbonylation of the allyl alcohols nerolidol and farnesol, it is possible, for example, to obtain carboxylic acids which, after reduction to the corresponding alcohols, can be cyclized to give valuable aroma chemicals. For example, (3E,7E)-homofarnesylic acid from the carbonylation of E-nerolidol can be subjected to a reduction to obtain (3E,7E)-homofarnesol

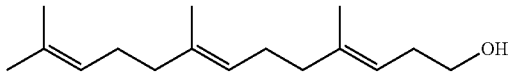 [SMILES: CC(C)=CCC/C(C)=C/CC/C(C)=C/CCO]

and the latter can be further subjected to a cyclization to obtain (−)-ambrox

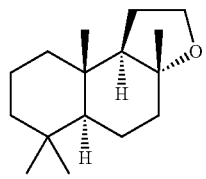

Processes for carbonylation of allyl alcohols to give their C1-extended linear carboxylic acids or carboxylic esters in the presence of homogeneous and also heterogeneous catalysts are known from the literature. However, these processes are economically disadvantageous for various reasons. For example, it is known that the direct carbonylation of allyl alcohols requires harsh conditions with regard to temperature and pressure and high catalyst loadings; in most cases, moreover, high conversions are achievable at all only with addition of halide-containing additives even when high pressures or temperatures or catalyst loadings are used. There is therefore a need for a process which enables the economically advantageous preparation of the carbonylation products of allyl alcohols.

Bertleff, W., Roeper, M. and Sava X. 2007 in Ullmann's Encyclopedia of Industrial Chemistry, Vol. 7, pages 74-98, 2012, Wiley-VCH describe carbonylation methods of industrial relevance.

Tsuji et al. in J. Am. Chem. Soc. 86, 1964, 4350-4353 describe the catalytic carbonylation of allyl compounds using palladium(II)chloride. Specifically, allyl chloride, allyl alcohol and analogous compounds are reacted with CO in organic solvents, giving the corresponding carboxylic esters with ethanol. The 3-butenoic anhydride is obtained from allyl alcohol in benzene as the solvent. The amount of palladium chloride used, based on allyl compound, is more than 5 mol % at pressures of 100 to 150 bar and temperatures of greater than 80° C.

B. Gabriele et al. in the Journal of Molecular Catalysis A, 111, 1996, 43-48 describe the carbonylation of allyl alcohols to give unsaturated acids or esters. The conversion is effected in dimethylacetamide or methanol/dimethylacetamide mixtures at pressures of 50-100 bar and temperatures of greater than 80° C. using a Pd catalyst at loadings of 2 mol % to 4 mol %.

T. Mandai in a review article in the Handbook of Organopalladium Chemistry for Organic Synthesis, editor: E. Negishi, Wiley-VCH, New York, Vol. 2, 2002, 2505-2517, describes, inter alfa, the carbonylation of allyl compounds with homogeneous palladium catalysts. It is pointed out that the carbonylation of allylic alcohols requires severe reaction conditions. It is likewise stated that the carbonylation of acetylated allyl alcohols, such as the structurally isomeric compounds (A) and (B), is generally difficult. According to the teaching of this document, however, the conversion succeeds in the presence of catalytic amounts of NaBr.

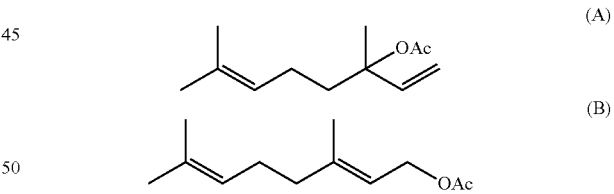

ACS Catal., 4, 2014, 2977-2989, in a review article, likewise describes the carbonylation of allyl compounds with homogeneous palladium catalysts.

By the process as described in the literature, the direct carbonylation of allyl alcohols requires high pressures or temperatures or catalyst loadings or the addition of halides as additive, and usually even a combination of at least two of these conversion-enhancing measures, in order to achieve sufficiently high reaction rates.

For instance, U.S. Pat. No. 4,801,743 describes the carbonylation of allyl alcohol (2-propen-1-ol) using a heterogeneous Pd catalyst in the absence of water and in the presence of a catalytically active amount of a hydrogen halide selected from HF, HCl, HBr and HI at pressures of greater than 150 bar and temperatures of greater than 80° C.

EP 0428979 A2 describes the carbonylation of allylic butenols and butenol esters using a homogeneous Rh catalyst in the presence of HBr or HI at CO pressures of 1 to 200 bar and temperatures of 10 to 250° C.

The aforementioned documents do describe processes for a carbonylation of allyl alcohols to give their C1-extended linear carboxylic acids or carboxylic esters. What is not described, however, is the carbonylation of allyl alcohols having terpene-like hydrocarbyl radicals and specifically the carbonylation of linalool to give E/Z-4,8-dimethyl-3,7-nonadienoic acid and of E-nerolidol or farnesol to give E/Z-homofarnesylic acid. All the processes described in the aforementioned documents also have one or more disadvantages that make them seem unsuitable for use for said conversions. For instance, the catalysts described in the aforementioned documents have too low an activity or the processes entail excessively harsh reaction conditions (with regard to acid, CO pressure, temperature) in order to enable effective economic carbonylation of allyl alcohols overall, and specifically the allyl alcohols having terpene-like hydrocarbyl radicals mentioned.

For instance, processes that necessitate high-pressure operation are industrially very costly. In many of the processes mentioned, the amount of catalyst used based on the substrate to be carbonylated is also very high. In the case of use of homogeneous catalyst systems that are generally discharged together with the product, high costs thus arise as a result of the catalyst recycling and unavoidable catalyst losses. Also problematic is the use of added hydrohalic acids and salts thereof. Because of the high corrosivity of these compounds, the use of reactors made from particularly high-quality steels is required. Moreover, process conditions of this kind are unsuitable for the conversion of E-nerolidol to homofarnesylic acid, since E-nerolidol does not have adequate stability toward strong acids such as HI.

Processes for carbonylation of E-nerolidol in the presence of homogeneous catalysts to give homofarnesylic acid or homofarnesylic acid alkyl esters are known in principle.

WO 92/06063 describes a process for preparing unsaturated carboxylic acids by carbonylating the corresponding allylic alcohols, for example the carbonylation of (E)-nerolidol with addition of catalytic amounts of palladium(II) chloride.

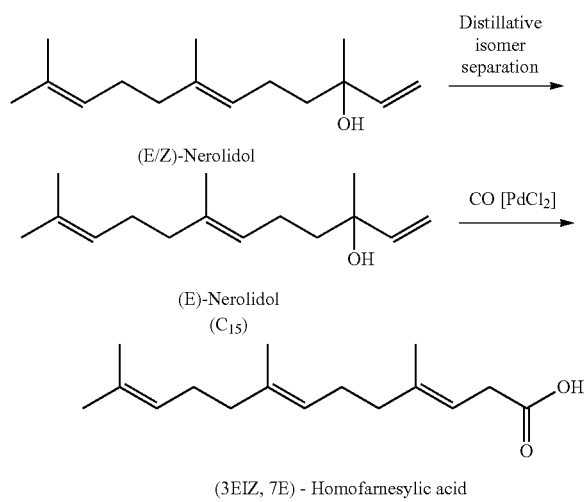

What is also described is the reduction of the carbonylation product thus obtained to give homofarnesol or monocyclohomofarnesol and the acid-catalyzed cyclization of homofarnesol to obtain 3a,6,6,9a-tetramethyldodecahydronaphtho-[2,1-b]-furan, an ambergris-like fragrance. A disadvantage of this process is that the carbonylation reaction takes place at high CO pressures of about 70 bar. In addition, a high catalyst loading of 0.6 mol % is used.

EP 0146859 A2 describes a process for preparing 4-substituted but-3-ene-1-carboxylic acids and esters thereof by carbonylation in the presence or absence of a lower alkanol (specifically methanol) with complexes of a palladium halide and a tertiary organic phosphine. The conversion is effected at pressures of 200 to 700 bar and temperatures of 50 to 150° C.

It is also known that substitutes for CO that enable ambient pressure conversion can be used for carbonylation. WO 2015/061764 and Tetrahedron: Asymmetry, 20, 2009, 1637-1640 describe the Pd-catalyzed use of N,N-dimethylformamide dimethyl acetal (DMFDMA) as CO substitute in the conversion of E-nerolidol and subsequent hydrolysis in methanol to give homofarnesylic acid methyl ester. However, such a two-stage process is synthetically complex and is also costly owing to the CO substitutes used, and so it is uneconomic on an industrial scale for carbonylation of allyl alcohols.

It is also known that allyl alcohols can be converted to the corresponding acetates and these acetates can be used as substrates in carbonylation reactions under comparatively mild conditions (pressures, for example, of 30 bar below 100° C.).

JOC, 53 1988, 3832-3828 describes the Pd- or Pt-catalyzed cyclizing carbonylation of cinnamyl acetates to 1-naphthol derivatives. The reaction is effected in the presence of acetic anhydride and triethylamine at 160° C. and 60 bar CO. The reason given for the addition of acetic anhydride is the necessity of converting the 1-naphthol formed as an intermediate to the corresponding acetate, since free 1-naphthol would inhibit the cyclocarbonylation. In terms of type, this reaction is a carbonylation in the presence of Pd and acetic anhydride, but does not lead to carboxylic acid derivatives.

Tetrahedron Letters, 29, 1988, 4945-4948 describes the conversion of allyl acetates in ethanol to the corresponding C1-extended carboxylic esters. The conversions are effected at 30 to 80 bar CO and 50 to 80° C. However, the conversion is effected not just in the presence of a base but also of catalytic amounts of bromide ions, which is said to dramatically accelerate the reaction. This document additionally points out that poor results were achieved with Pd(II) catalysts such as palladium(II) acetate (Pd(OAc)$_2$).

JOC, 58, 1993, 1538-1545 describes the Pd(0)-catalyzed alkoxycarbonylation of allyl acetates. This document too refers to the necessity of the presence of halide ions for acceleration of the reaction. By contrast, only a low reactivity in the carbonylation is ascribed to the allyl acetates.

There is thus no specific method in the literature for direct carbonylation of allyl alcohols and specifically of E-nerolidol to give homofarnesylic acid (or derivatives of homofarnesylic acid such as the corresponding salts or esters) that proceeds effectively and economically under mild reaction conditions. This is understood to mean that the conversion proceeds at pressures in the region of not more than 30 bar CO and/or at temperatures below 100° C. and/or in the absence of halogen compounds selected from hydrohalic acids and alkali metal, alkaline earth metal or ammonium halides or a combination of at least two of these measures.

It has been found that, surprisingly, even the addition of catalytic amounts of a carboxylic anhydride, such as Ac$_2$O (acetic anhydride) is sufficient to fully carbonylate allyl alcohols under mild reaction conditions and with low catalyst loadings to the corresponding carboxylic acid. Particularly advantageous results are achieved here with addition of a nucleophilic reagent such as an alkylpyridine, 4-(1-pyrrolidinyl)pyridine or a dialkylaminopyridine, specifically DMAP (4-dimethylaminopyridine). Particularly surprisingly, even the addition of catalytic amounts of acylation products of allyl alcohols without the addition of carboxylic anhydrides is sufficient to accelerate the reaction by a number of orders of magnitude. These acylation products of allyl alcohols may also be esters of allyl alcohols other than the substrate itself with carboxylic acids (for example allyl acetate). In the light of the prior art, the person skilled in the art, if considering the use of acylation products of allyl alcohol at all, would have used at least a stoichiometric amount of acylated allyl alcohol (or of an acylating agent). The fact that this reaction regime works as described with catalytic amounts of activating reagent was unknown, was not obvious and is very advantageous for the efficiency of the overall process.

It is therefore an object of the present invention to provide a process for carbonylating allyl alcohols or the acylation products thereof to obtain unsaturated carboxylic acids or salts thereof, in which the aforementioned disadvantages are avoided.

In a specific embodiment, it is an object of the invention to provide a process for carbonylating E-nerolidol in which a product mixture comprising (3E,7E)-4,8,12-trimethyltrideca-3,7,11-trienoic acid (homofarnesylic acid) and (3Z,7E)-4,8,12-trimethyltrideca-3,7,11-trienoic acid or the salts thereof is obtained.

It has now been found that, surprisingly, the carbonylation of allyl alcohols and derivatives of allyl alcohol to give C1-extended unsaturated carboxylic acids or corresponding carboxylic salts can be conducted at temperatures of not more than 100° C. It has been found that, advantageously, the carbonylation of alcohols and derivatives of allyl alcohol to give C1-extended unsaturated carboxylic acids or corresponding carboxylic salts can be conducted at temperatures of not more than 100° C. and at low pressure, for example at a pressure of not more than 30 bar. It has additionally been found that, advantageously, the carbonylation of alcohols and derivatives of allyl alcohol to give C1-extended unsaturated carboxylic acids or corresponding carboxylic salts can be conducted at temperatures of not more than 100° C. with simultaneously low catalyst loadings of less than 0.3 mol % and at simultaneously low pressure, for example at a pressure of not more than 30 bar. It has additionally been found that the conversion can also be effected without addition of accelerating halides.

SUMMARY OF THE INVENTION

The invention firstly provides a process for preparing a composition comprising at least one unsaturated carboxylic acid of the general formula (I)

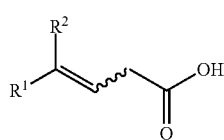

(I)

or a salt thereof, in which
R$^1$ is hydrogen, linear or branched C$_1$-C$_{24}$-alkyl, linear or branched C$_2$-C$_{24}$-alkenyl having 1, 2, 3 or more than 3 C—C double bonds, unsubstituted C$_5$-C$_{12}$-cycloalkyl or C$_5$-C$_{12}$-cycloalkyl substituted by 1, 2 or 3 C$_1$-C$_6$-alkyl radicals or unsubstituted aryl or aryl substituted by 1, 2 or 3 C$_1$-C$_6$-alkyl radicals,
R$^2$ is hydrogen, linear or branched C$_1$-C$_{24}$-alkyl or linear or branched C$_2$-C$_{24}$-alkenyl having 1, 2, 3 or more than 3 C—C double bonds, or
R$^1$ and R$^2$ together with the carbon atom to which they are bonded are unsubstituted C$_5$-C$_7$-cycloalkyl or are C$_5$-C$_7$-cycloalkyl bearing 1, 2 or 3 linear or branched C$_1$-C$_6$-alkyl radicals,
in which an allyl alcohol selected from compounds of the general formulae (II.1) and (II.2)

(II.1)

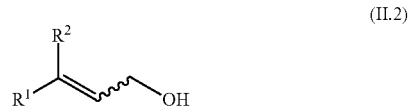

(II.2)

is subjected to a carbonylation by reaction with carbon monoxide in the presence of a transition metal catalyst comprising at least one metal of groups 8, 9 and 10 of the Periodic Table of the Elements, wherein the reaction is additionally effected in the presence of at least one organic phosphorus compound as ligand and in the presence of a substoichiometric amount, based on the allyl alcohol, of a compound A) selected from anhydrides of aliphatic C$_1$-C$_{12}$-monocarboxylic acids, anhydrides of aliphatic C$_4$-C$_{20}$-dicarboxylic acids, anhydrides of cycloaliphatic C$_7$-C$_{20}$-dicarboxylic acids, anhydrides of aromatic C$_8$-C$_{20}$-dicarboxylic acids and acylated allyl alcohols of the formulae (III.1) and (III.2)

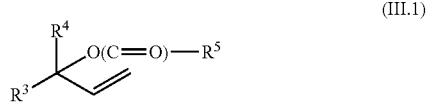

(III.1)

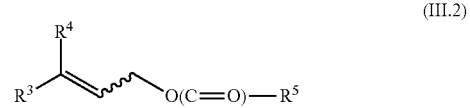

(III.2)

in which
R$^3$ is hydrogen, linear or branched C$_1$-C$_{24}$-alkyl, linear or branched C$_2$-C$_{24}$-alkenyl having 1, 2, 3 or more than 3 C—C double bonds, unsubstituted C$_5$-C$_{12}$-cycloalkyl or C$_5$-C$_{12}$-cycloalkyl substituted by 1, 2 or 3 C$_1$-C$_6$-alkyl radicals or unsubstituted aryl or aryl substituted by 1, 2 or 3 C$_1$-C$_6$-alkyl radicals,
R$^4$ is hydrogen, linear or branched C$_1$-C$_{24}$-alkyl or linear or branched C$_2$-C$_{24}$-alkenyl having 1, 2, 3 or more than 3 C—C double bonds, or
R$^3$ and R$^4$ together with the carbon atom to which they are bonded are unsubstituted C$_5$-C$_7$-cycloalkyl or are C$_5$-C$_7$-cycloalkyl bearing 1, 2 or 3 linear or branched C$_1$-C$_6$-alkyl radicals, R$^5$ is C$_1$-C$_5$-alkyl, and wherein the reaction is effected at a temperature of not more than 100° C.

The embodiment of the process of the invention in which an allyl alcohol selected from compounds of the general formulae (II.1) and (II.2) is used in the presence of a compound A) for the reaction is also referred to hereinafter as "Variant 1".

A specific embodiment of variant 1 is a process for preparing a composition comprising at least one unsaturated carboxylic acid of the general formula (I)

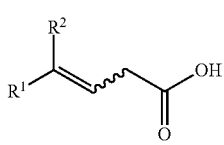

(I)

or of a salt thereof, in which
$R^1$ is hydrogen, linear or branched $C_1$-$C_{24}$-alkyl, linear or branched $C_2$-$C_{24}$-alkenyl having 1, 2, 3 or more than 3 C—C double bonds, unsubstituted $C_5$-$C_{12}$-cycloalkyl or $C_5$-$C_{12}$-cycloalkyl substituted by 1, 2 or 3 $C_1$-$C_6$-alkyl radicals or unsubstituted aryl or aryl substituted by 1, 2 or 3 $C_1$-$C_6$-alkyl radicals,
$R^2$ is hydrogen, linear or branched $C_1$-$C_{24}$-alkyl or linear or branched $C_2$-$C_{24}$-alkenyl having 1, 2, 3 or more than 3 C—C double bonds, or
$R^1$ and $R^2$ together with the carbon atom to which they are bonded are unsubstituted $C_5$-$C_7$-cycloalkyl or are $C_5$-$C_7$-cycloalkyl bearing 1, 2 or 3 linear or branched $C_1$-$C_6$-alkyl radicals,
in which an allyl alcohol selected from compounds of the general formulae (II.1) and (II.2)

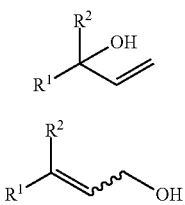

(II.1)

(II.2)

is subjected to a carbonylation by reaction with carbon monoxide in the presence of a transition metal catalyst comprising at least one metal of groups 8, 9 and 10 of the Periodic Table of the Elements, wherein the reaction is additionally effected in the presence of at least one organic phosphorus compound as ligand and in the presence of a substoichiometric amount, based on the allyl alcohol, of a compound A) selected from anhydrides of aliphatic $C_1$-$C_{12}$-monocarboxylic acids, anhydrides of aliphatic $C_4$-$C_{20}$-dicarboxylic acids, anhydrides of cycloaliphatic $C_7$-$C_{20}$-dicarboxylic acids, anhydrides of aromatic $C_8$-$C_{20}$-dicarboxylic acids and acylated allyl alcohols of the formulae (III.1) and (III.2)

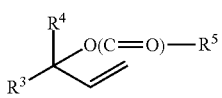

(III.1)

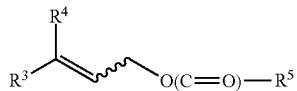

(III.2)

in which
$R^3$ is hydrogen, linear or branched $C_1$-$C_{24}$-alkyl, linear or branched $C_2$-$C_{24}$-alkenyl having 1, 2, 3 or more than 3 C—C double bonds, unsubstituted $C_5$-$C_{12}$-cycloalkyl or $C_5$-$C_{12}$-cycloalkyl substituted by 1, 2 or 3 $C_1$-$C_6$-alkyl radicals or unsubstituted aryl or aryl substituted by 1, 2 or 3 $C_1$-$C_6$-alkyl radicals,
$R^4$ is hydrogen, linear or branched $C_1$-$C_{24}$-alkyl or linear or branched $C_2$-$C_{24}$-alkenyl having 1, 2, 3 or more than 3 C—C double bonds, or
$R^3$ and $R^4$ together with the carbon atom to which they are bonded are unsubstituted $C_5$-$C_7$-cycloalkyl or are $C_5$-$C_7$-cycloalkyl bearing 1, 2 or 3 linear or branched $C_1$-$C_6$-alkyl radicals,
$R^5$ is $C_1$-$C_5$-alkyl,
and wherein the reaction is effected at a temperature of not more than 100° C. and at a pressure of not more than 30 bar.

In an alternative embodiment, it is possible to use an acylated allyl alcohol for the carbonylation. In this variant too, it is possible to conduct the reaction under advantageously mild reaction conditions. According to the invention, the conversion in this variant is effected in the presence of water. The invention therefore further provides a process for preparing a composition comprising at least one unsaturated carboxylic acid of the general formula (I)

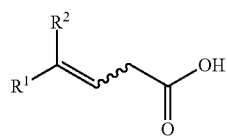

(I)

or of a salt thereof, in which
$R^1$ is hydrogen, linear or branched $C_1$-$C_{24}$-alkyl, linear or branched $C_2$-$C_{24}$-alkenyl having 1, 2, 3 or more than 3 C—C double bonds, unsubstituted $C_5$-$C_{12}$-cycloalkyl or $C_5$-$C_{12}$-cycloalkyl substituted by 1, 2 or 3 $C_1$-$C_6$-alkyl radicals or unsubstituted aryl or aryl substituted by 1, 2 or 3 $C_1$-$C_6$-alkyl radicals,
$R^2$ is hydrogen, linear or branched $C_1$-$C_{24}$-alkyl or linear or branched $C_2$-$C_{24}$-alkenyl having 1, 2, 3 or more than 3 C—C double bonds, or
$R^1$ and $R^2$ together with the carbon atom to which they are bonded are unsubstituted $C_5$-$C_7$-cycloalkyl or are $C_5$-$C_7$-cycloalkyl bearing 1, 2 or 3 linear or branched $C_1$-$C_6$-alkyl radicals,
in which an acylated allyl alcohol selected from compounds of the general formulae (IV. 1) and (IV.2)

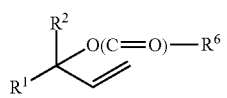

(IV.1)

-continued

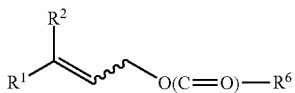
(IV.2)

in which $R^6$ is $C_1$-$C_5$-alkyl,
is subjected to a carbonylation by reaction with carbon monoxide in the presence of a transition metal catalyst comprising at least one metal of groups 8, 9 and 10 of the Periodic Table of the Elements, wherein the reaction is additionally effected in the presence of at least one organic phosphorus compound as ligand and in the presence of water and wherein the reaction is effected at a temperature of not more than 100° C.

The embodiment of the process of the invention in which an acylated allyl alcohol selected from compounds of the general formulae (IV.1) and (IV.2) is used for the reaction is also referred to hereinafter as "Variant 2".

A specific embodiment of variant 2 is a process for preparing a composition comprising at least one unsaturated carboxylic acid of the general formula (I)

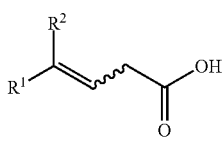
(I)

or of a salt thereof,
in which
$R^1$ is hydrogen, linear or branched $C_1$-$C_{24}$-alkyl, linear or branched $C_2$-$C_{24}$-alkenyl having 1, 2, 3 or more than 3 C—C double bonds, unsubstituted $C_5$-$C_{12}$-cycloalkyl or $C_5$-$C_{12}$-cycloalkyl substituted by 1, 2 or 3 $C_1$-$C_6$-alkyl radicals or unsubstituted aryl or aryl substituted by 1, 2 or 3 $C_1$-$C_6$-alkyl radicals,
$R^2$ is hydrogen, linear or branched $C_1$-$C_{24}$-alkyl or linear or branched $C_2$-$C_{24}$-alkenyl having 1, 2, 3 or more than 3 C—C double bonds, or
$R^1$ and $R^2$ together with the carbon atom to which they are bonded are unsubstituted $C_5$-$C_7$-cycloalkyl or are $C_5$-$C_7$-cycloalkyl bearing 1, 2 or 3 linear or branched $C_1$-$C_6$-alkyl radicals,
in which an acylated allyl alcohol selected from compounds of the general formulae (IV.1) and (IV.2)

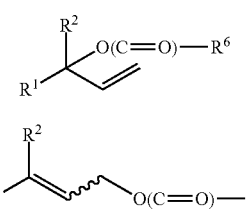
(IV.1)

(IV.2)

in which $R^6$ is $C_1$-$C_5$-alkyl,
is subjected to a carbonylation by reaction with carbon monoxide in the presence of a transition metal catalyst comprising at least one metal of groups 8, 9 and 10 of the Periodic Table of the Elements, wherein the reaction is additionally effected in the presence of at least one organic phosphorus compound as ligand and in the presence of water and wherein the reaction is effected at a temperature of not more than 100° C. and at a pressure of not more than 30 bar.

A further alternative embodiment relates to processes for preparing a composition comprising at least one unsaturated carboxylic acid of the general formula (I)

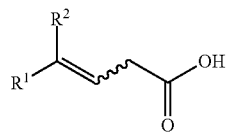
(I)

or a salt thereof, in which
$R^1$ is hydrogen, linear or branched $C_1$-$C_{24}$-alkyl, linear or branched $C_2$-$C_{24}$-alkenyl having 1, 2, 3 or more than 3 C—C double bonds, unsubstituted $C_5$-$C_{12}$-cycloalkyl or $C_5$-$C_{12}$-cycloalkyl substituted by 1, 2 or 3 $C_1$-$C_6$-alkyl radicals or unsubstituted aryl or aryl substituted by 1, 2 or 3 $C_1$-$C_6$-alkyl radicals,
$R^2$ is hydrogen, linear or branched $C_1$-$C_{24}$-alkyl or linear or branched $C_2$-$C_{24}$-alkenyl having 1, 2, 3 or more than 3 C—C double bonds, or
$R^1$ and $R^2$ together with the carbon atom to which they are bonded are unsubstituted $C_5$-$C_7$-cycloalkyl or are $C_5$-$C_7$-cycloalkyl bearing 1, 2 or 3 linear or branched $C_1$-$C_6$-alkyl radicals,
in which an allyl alcohol selected from compounds of the general formulae (II.1) and (II.2)

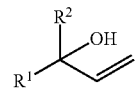
(II.1)

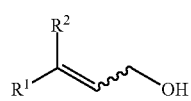
(II.2)

is subjected to a carbonylation by reaction with carbon monoxide in the presence of a transition metal catalyst comprising at least one metal of groups 8, 9 and 10 of the Periodic Table of the Elements, wherein the reaction is additionally effected in the presence of at least one organic phosphorus compound as ligand and in the presence of a substoichiometric amount, based on the allyl alcohol, of a compound B)

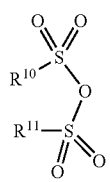
(B)

in which
$R^{10}$ and $R^{11}$, independently of one another, are $C_1$-$C_6$-alkyl, $C_1$-$C_6$-fluoroalkyl or phenyl which is unsubstituted or substituted by a substituent selected from bromo, nitro and $C_1$-$C_4$-alkyl;

and wherein the reaction is effected at a temperature of not more than 100° C. Specifically, the reaction is effected at a temperature of not more than 100° C. and a pressure of not more than 30 bar.

In this variant too, it is possible to conduct the reaction under advantageously mild reaction conditions. The embodiment of the process of the invention in which an allyl alcohol selected from compounds of the general formulae (II.1) and (II.2) is used for reaction in the presence of a compound B) is also referred to hereinafter as "variant 3".

The invention further provides a process for preparing (−)-ambrox (VIII)

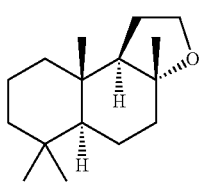

(VIII)

in which
a1) a mixture of (3E,7E)-4,8,12-trimethyltrideca-3,7,11-trienoic acid and (3Z,7E)-4,8,12-trimethyltrideca-3,7,11-trienoic acid obtainable by a process as defined above is provided;
b1) the mixture of (3E,7E)-4,8,12-trimethyltrideca-3,7,11-trienoic acid and (3Z,7E)-4,8,12-trimethyltrideca-3,7,11-trienoic acid is subjected to a separation to obtain (3E,7E)-4,8,12-trimethyltrideca-3,7,11-trienoic acid;
c1) the (3E,7E)-4,8,12-trimethyltrideca-3,7,11-trienoic acid is subjected to a reduction to obtain (3E,7E)-homofarnesol (VI);
d1) the (3E,7E)-homofarnesol (VI) is subjected to a cyclization to obtain (−)-ambrox (VIII);
or
a2) a mixture of (3E,7E)-4,8,12-trimethyltrideca-3,7,11-trienoic acid and (3Z,7E)-4,8,12-trimethyltrideca-3,7,11-trienoic acid obtainable by a process as defined above is provided;
b2) the mixture of (3E,7E)-4,8,12-trimethyltrideca-3,7,11-trienoic acid and (3Z,7E)-4,8,12-trimethyltrideca-3,7,11-trienoic acid is subjected to a separation to obtain (3E,7E)-4,8,12-trimethyltrideca-3,7,11-trienoic acid;
c2) the (3E,7E)-4,8,12-trimethyltrideca-3,7,11-trienoic acid is subjected to a cyclization to obtain sclareolide (VII);
d2) the sclareolide (VII) is subjected to a reduction to obtain (−)-ambrox (VIII).

DESCRIPTION OF THE INVENTION

The processes of the invention for preparing a composition comprising at least one unsaturated carboxylic acid of the general formula (I) have the following advantages:
Variant 1 of the process enables the effective and economic conversion of allyl alcohols to their C1-extended unsaturated carboxylic acids or corresponding carboxylic salts. Much milder reaction conditions (with simultaneously very low catalyst loadings) are possible here than in the processes known from the prior art. Specifically, conversion is possible at lower temperature and/or a lower pressure and/or a lower catalyst loading than in the known processes.
It is particularly advantageous that, in variant 1 of the process of the invention, conversion in the presence of catalytic (i.e. substoichiometric) amounts of anhydride is sufficient to fully carbonylate the allylic alcohols under mild reaction conditions and at low catalyst loadings to the corresponding carboxylic acids. Particularly surprisingly, even the addition of catalytic amounts of other anhydride formers, such as allyl acetate (propenyl acetate) or different acylation products of allyl alcohols is sufficient to distinctly accelerate the reaction. The addition of additional anhydride is not required here. Without wishing to be bound to any theory, it is assumed that this is attributable to the fact that, under the reaction conditions, there is initial carbonylation of the acylated allyl alcohol added (e.g. allyl acetate $CH_2$=$CHCH_2OAc$) to give an anhydride intermediate (e.g. $CH_2$=$CHCH_2C(O)OAc$), and the anhydride formed in situ activates the allylic alcohol used (e.g. nerolidol) with elimination of carboxylic acid (e.g. $CH_2$=$CHCH_2CO_2H$), simultaneously generating new acylated allyl alcohol (e.g. nerolidyl acetate) which can in turn be carbonylated again to give the corresponding anhydride intermediate (mixed anhydride of acetic acid and homofarnesylic acid).

The possibility of using catalytic amounts of a nucleophilic reagent in variant 1 of the process is very advantageous for the efficiency of the overall process.

The process of the invention according to variant 1 enables the carbonylation of allyl alcohols to obtain the corresponding carboxylic acids or carboxylic salts in a single reaction stage, i.e. without the isolation of an intermediate. For example, it is unnecessary to activate the allyl alcohol used in a first reaction step using stoichiometric amounts of acylating agent.

If the allyl alcohols used for carbonylation comprise further internal double bonds, these are essentially neither carbonylated nor isomerized.

The alternative variant 2 of the process is based on the carbonylation of acylated alcohols to give their C1-extended unsaturated carboxylic acids in the presence of water under mild reaction conditions.

The processes according to variants 1 and 2 make it possible to dispense with the use of added hydrohalic acids and salts thereof.

The process according to variant 1 specifically enables the carbonylation of allyl alcohols having terpene-like hydrocarbyl radicals and specifically the carbonylation of linalool to give E/Z-4,8-dimethyl-3,7-nonadienoic acid and of E-nerolidol or farnesol to give E/Z-homofarnesylic acid under mild reaction conditions.

By the process according to variant 1, it is advantageously possible to carbonylate E-nerolidol to obtain a reaction mixture composed of (3E,7E)-4,8,12-trimethyltrideca-3,7,11-trienoic acid (homofarnesylic acid) and (3Z,7E)-4,8,12-trimethyltrideca-3,7,11-trienoic acid or the salts thereof.

In the compounds of the general formulae (I), (II.2), (III.2) and (IV.2)

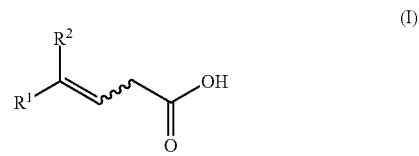

(I)

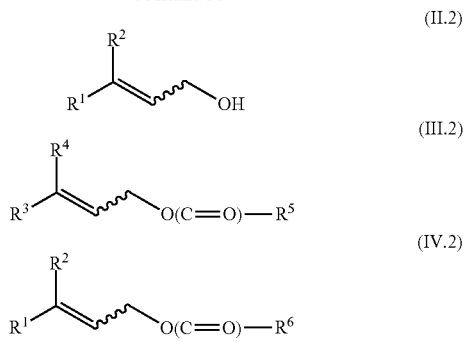

(II.2)

(III.2)

(IV.2)

the wavy bond is supposed to indicate that the compound may be the pure Z isomer, the pure E isomer or any E/Z mixture. It will be self-evident to the person skilled in the art that, in the compounds of the general formulae (I), (II.2), and (IV.2), E and Z isomers can only exist when two different substituents $R^1$ and $R^2$ are bonded to the double bond. In the compounds of the general formula (III.2), E and Z isomers may exist only when two different substituents $R^3$ and $R^4$ are bonded to the double bond. The stereochemical configuration at the double bond is ascertained with the aid of the Cahn-Ingold-Prelog rules (see E/Z notation, en.wikipedia.org/wiki/E-Z_notation).

In the context of the present invention, the E/Z mixture of the general formula (I) is also referred to as E/Z acid mixture of the formula (I). In the E/Z acid mixture of the general formula (I), $R^1$ and $R^2$ have different meanings. The E/Z acid mixture of the formula (I) comprises the 3-(E) isomer of the unsaturated carboxylic acid of the formula I and the 3-(Z) isomer of the unsaturated carboxylic acid of the formula I. The 3-(E) isomer of the unsaturated carboxylic acid of the formula I is referred to hereinafter as 3-(E) isomer of the formula (I-E), and the 3-(Z) isomer of the unsaturated carboxylic acid as the 3-(Z) isomer of the formula (I-Z).

In the general formulae of the compounds I-Z and I-E

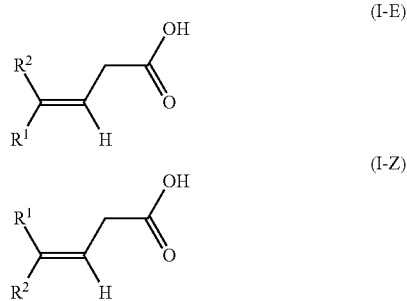

(I-E)

(I-Z)

the substituent $R^1$ has a higher priority according to IUPAC (International Union of Pure and Applied Chemistry) than the substituent $R^2$. According to IUPAC, the sequence of priority of the substituents is according to the Cahn-Ingold-Prelog rule.

It is generally assumed that the transition metal-catalyzed and specifically the Pd-catalyzed carbonylation proceeds via a pi-allyl complex which makes it possible to obtain respective reaction products comprising the compounds (I) either proceeding from the compounds (II.1) or from the compounds (II.2).

Preferably, the carbonylation is not effected in the presence of an added hydrohalic acid and not in the presence of added alkali metal halide, alkaline earth metal halide or ammonium halide. The expression "ammonium salt" means both salts that derive from $NH_4+$ and mono-, di-, tri- and tetraorganylammonium salts. Specifically, the carbonylation is not effected in the presence of an added alkyl halide, such as NaCl, NaBr, KCl, KBr, LiCl, LiBr, etc.

Preferably, the halide content of the reaction mixture of the carbonylation is not more than 2 mol %, preferably not more than 1 mol %, based on the content of allyl alcohol of the general formulae (II.1) and (II.2).

In the context of the present invention, the terms "acylated allyl alcohol", "allyl carboxylate", "acylation product of allyl alcohol" and "acylation product of an allyl alcohol" are used synonymously.

The expression "aliphatic" in the context of the present invention comprises hydrocarbyl radicals in which the carbon atoms are arranged in straight or branched chains.

The expression "alkyl" and all alkyl moieties in alkoxy, alkylamino and dialkylamino in the context of the present invention comprises saturated, linear or branched hydrocarbon radicals having 1 to 4 ("$C_1$-$C_4$-alkyl"), 1 to 6 ("$C_1$-$C_6$-alkyl"), 1 to 10 ("$C_1$-$C_{10}$-alkyl"), 1 to 20 ("$C_1$-$C_{20}$-alkyl") or 1 to 24 ("$C_1$-$C_{24}$-alkyl") carbon atoms. Examples of linear or branched $C_1$-$C_4$-alkyl are methyl, ethyl, n-propyl, 1-methylethyl, n-butyl, 1-methylpropyl, 2-methylpropyl, 1,1-dimethylethyl. Examples of linear or branched $C_1$-$C_6$-alkyl, in addition to the definitions given for $C_1$-$C_4$-alkyl, are n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Examples of linear or branched $C_1$-$C_{10}$-alkyl, in addition to the definitions given for $C_1$-$C_6$-alkyl, are heptyl, octyl, nonyl, decyl and positional isomers thereof. Examples of $C_1$-$C_{20}$-alkyl, in addition to the definitions given for $C_1$-$C_{10}$-alkyl, are undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, eicosyl and positional isomers thereof.

The expression "alkenyl" in the context of the present invention comprises unsaturated, linear or branched hydrocarbon radicals having 2 to 4 ($C_2$-$C_4$-alkenyl), to 6, to 8, to 10, to 16, to 20 or to 24 carbon atoms and one, two, three or more than three double bonds in any position. Examples of linear or branched $C_2$-$C_{24}$-alkenyl having one double bond are vinyl, allyl (2-propen-1-yl), 1-methylprop-2-en-1-yl, 2-buten-1-yl, 3-buten-1-yl, n-pentenyl, n-hexenyl, n-heptenyl, n-octenyl, n-nonenyl, n-decenyl, n-undecenyl, n-dodecenyl, n-tridecenyl, n-tetradecenyl, n-pentadecenyl, n-hexadecenyl, n-heptadecenyl, n-octadecenyl, oleyl, n-nonadecenyl, n-eicosenyl, n-heneicosenyl, n-docosenyl, n-tricosenyl, n-tetracosenyl and the constitutional isomers thereof. Examples of linear or branched $C_4$-$C_{24}$-alkenyl having two or three double bonds in any position are n-butadienyl, n-pentadienyl, n-hexadienyl, n-heptadienyl, n-octadienyl, n-octatrienyl, n-nonadienyl, n-nonatrienyl, n-decadienyl, n-decatrienyl, n-undecadienyl, n-undecatrienyl, n-dodecadienyl, n-dodecatrienyl, n-tridecadienyl, n-tridecatrienyl, n-tetradecadienyl, n-tetradecatrienyl, n-pentadecadienyl, n-pentadecatrienyl, n-hexadecadienyl, n-hexadecatrienyl, n-heptadecadienyl, n-heptadecatrienyl, n-octadecadienyl, n-octadecatrienyl, n-nonadecadienyl, n-nonadecatrienyl, n-eicosadienyl, n-eicosatrienyl, n-heneicosadienyl, n-heneicosatrienyl, n-docosadienyl, n-docosatrienyl, n-tricosadienyl, n-tricosatrienyl, n-tetracosadienyl, n-tetracosatrienyl, linolenyl and constitutional isomers thereof. Every double bond in $C_2$-$C_{24}$-alkenyl may (unless stated otherwise) in each case independently be in the E configuration or in the Z configuration.

The expression "cycloalkyl" in the context of the present invention comprises monocyclic saturated hydrocarbon radicals having 3 to 8 ("$C_3$-$C_8$-cycloalkyl"), preferably 5 to 7 carbon ring members ("$C_5$-$C_7$-cycloalkyl"). Examples of $C_3$-$C_8$-cycloalkyl are cyclopropyl, cyclobutyl, cyclopentyl, cyclohexyl, cycloheptyl and cyclooctyl.

The expression "heterocyclyl" (also referred to as heterocycloalkyl) in the context of the present invention encompasses monocyclic saturated cycloaliphatic groups having generally 5 to 8 ring atoms, preferably 5 or 6 ring atoms, in which 1 or 2 of the ring carbon atoms are replaced by heteroatoms or heteroatom-containing groups selected from oxygen, nitrogen, NH and N($C_1$-$C_4$-alkyl). Examples of such heterocycloaliphatic groups are pyrrolidinyl, piperidinyl, tetrahydrofuranyl and tetrahydropyranyl.

The expression "aryl" in the context of the present invention comprises a mono-, di- or tricyclic aromatic ring system comprising 6 to 20 carbon ring members. Examples of unsubstituted $C_6$-$C_{10}$-aryl are phenyl and naphthyl. Examples of $C_6$-$C_{14}$-aryl are phenyl, naphthyl, anthracenyl and phenanthrenyl. Substituted aryl groups generally bear 1, 2, 3, 4 or 5 identical or different substituents, preferably 1, 2 or 3 substituents. Suitable substituents are especially selected from alkyl, cycloalkyl, aryl, alkoxy, dialkylamino. Examples of aryl that bears 1, 2 or 3 substituents selected from $C_1$-$C_6$-alkyl are tolyl, xylyl and mesityl.

The expression "hetaryl" in the context of the present invention comprises a five- to six-membered aromatic heteromonocycle comprising one, two, three or four heteroatoms from the group of oxygen, nitrogen and sulfur, and 9- or 10-membered aromatic heterobicycles, e.g. carbon-bonded 5-membered heteroaryl comprising one to three nitrogen atoms or one or two nitrogen atoms and one sulfur or oxygen atom as ring members, such as furyl, thienyl, pyrrolyl, isoxazolyl, isothiazolyl, pyrazolyl, oxazolyl, thiazolyl, imidazolyl, 4-imidazolyl, 1,2,4-oxadiazolyl, 1,2,4-thiadiazolyl, 1,2,4-triazolyl, 1,3,4-oxadiazolyl; nitrogen-bonded 5-membered heteroaryl comprising one to three nitrogen atoms as ring members, such as pyrrol-1-yl, pyrazol-1-yl, imidazol-1-yl, 1,2,3-triazol-1-yl and 1,2,4-triazol-1-yl; 6-membered heteroaryl comprising one to three nitrogen atoms as ring members, such as pyridinyl, pyridazinyl, pyrimidinyl, pyrazinyl, 1,3,5-triazinyl and 1,2,4-triazinyl.

Halogen is fluorine, chlorine, bromine or iodine. Halide is fluoride, chloride, bromide or iodide.

Alkali metals correspond to the group 1 elements of the Periodic Table of the Elements according to IUPAC, for example lithium, sodium, potassium, rubidium or cesium, preferably lithium, sodium or potassium, especially sodium or potassium.

Alkaline earth metals correspond to the group 2 elements of the Periodic Table of the Elements according to IUPAC, for example beryllium, magnesium, calcium, strontium or barium, preferably magnesium or calcium.

Group 8 of the Periodic Table of the Elements according to IUPAC comprises, inter alia, iron, ruthenium and osmium. Group 9 of the Periodic Table of the Elements according to IUPAC comprises, inter alia, cobalt, rhodium, iridium. Group 10 of the Periodic Table of the Elements according to IUPAC comprises, inter alia, nickel, palladium and platinum.

The expression "ammonium salts" in the context of the present invention comprises both salts that derive from $NH_4+$ and mono-, di-, tri- and tetraorganylammonium salts. The radicals bonded to the ammonium nitrogen are generally each independently selected from hydrogen and aliphatic, alicyclic and aromatic hydrocarbon groups. Preferably, the radicals bonded to the ammonium nitrogen are each independently selected from hydrogen and aliphatic radicals, especially selected from hydrogen and $C_1$-$C_{20}$-alkyl.

The expression "acyl" in the context of the present invention comprises alkanoyl or aroyl groups having generally 1 to 11 and preferably 2 to 8 carbon atoms, for example the formyl, acetyl, propionyl, butyryl, pentanoyl, benzoyl or naphthoyl group.

Acetylation in the context of the present invention is the exchange of hydrogen for an acetyl group (—C(=O)—$CH_3$).

Unless stated more specifically hereinafter, the general formulae (I), (II.2), (III.2) and (IV.2) refer to E/Z mixtures of any composition and the pure configurational isomers. In addition, the general formulae (I), (II.2), (III.2) and (IV.2) refer to all stereoisomers in pure form and to racemic and optically active mixtures of the compounds of the formulae (II.2), (III.2) and (IV.2).

"Stereoisomers" are compounds of the same constitution but different atomic arrangement in three-dimensional space.

"Enantiomers" are stereoisomers which behave with respect to one another like an image and mirror image.

The term "terpene-like hydrocarbyl radicals" in the context of the present invention comprises hydrocarbyl radicals that derive in a formal sense from one, two, three or more than three isoprene units. The terpene-like hydrocarbyl radicals may still have double bonds or may be fully saturated. The double bonds can assume any desired positions, excluding cumulated double bonds.

The term "farnesol (3,7,11-trimethyl-2,6,10-dodecatrien-1-ol)" in the context of the present invention comprises the (2E,6E), (2Z,6Z), (2Z,6E) and (2E,6Z) isomers and mixtures of two, three or all the isomers of farnesol mentioned. Farnesol is commercially available.

Nerolidol has one chiral center and may be in the form of an E/Z mixture, meaning that there are four stereoisomers. The term "nerolidol (3,7,11-trimethyl-1,6,10-dodecatrien-3-ol)" in the context of the present invention comprises the (3S), (6Z) isomer, (3R), (6Z) isomer, (3S), (6E) isomer, (3R), (6E) isomer and any desired mixtures thereof. Nerolidol is commercially available. Nerolidyl acetate (3,7,11-trimethyl-1,6,10-octatrienyl acetate) is the acetylation product of nerolidol. It is likewise commercially available.

Another name for homofarnesylic acid is 4,8,12-trimethyltrideca-3,7,11-trienoic acid.

A first embodiment of the present invention (variant 1) relates to the carbonylation of an allylic alcohol (allyl alcohol) selected from compounds of the formulae (II.1) and (II.2) to give the corresponding C1-extended unsaturated carboxylic acids of the formula (I).

The starting compounds of the formula (II.1) are commercially available or can be prepared, for example, from the corresponding carbonyl compounds $R^1$—CO—$R^2$ and vinylmagnesium halides. The compounds of the formula (II.1) can also be prepared from the corresponding carbonyl compound and acetylides such as sodium acetylide and subsequent partial hydrogenation of the ethynyl group to give the vinyl group.

Allyl alcohols of the formula (II.1) and (II.2) that are preferred in the context of the process of the invention are those in which the $R^1$ and $R^2$ radicals are the same or different and are hydrogen, linear or branched $C_1$-$C_{16}$-alkyl, linear or branched $C_2$-$C_{16}$-alkenyl having one or two nonconjugated double bonds, or $R^1$ and $R^2$ together with the carbon atom to which they are bonded are unsubstituted $C_5$-$C_7$-cycloalkyl or $C_5$-$C_7$-cycloalkyl bearing 1, 2 or 3 linear or branched $C_1$-$C_6$-alkyl radicals.

Especially preferred are compounds of the formulae (II.1) and (II.2) having terpene-like hydrocarbyl radicals. $R^1$ is preferably linear or branched $C_6$-$C_{16}$-alkyl or linear or branched $C_6$-$C_{16}$-alkenyl having one or two nonconjugated double bonds. $R^2$ is preferably hydrogen or $C_1$-$C_4$-alkyl, especially $C_1$-$C_2$-alkyl. Allyl alcohols of the formula (II.1) that are particularly preferred in accordance with the invention are 3-methyl-1-penten-3-ol, 1-hepten-3-ol, 1-vinylcyclohexanol, linalool and nerolidol, especially linalool and nerolidol, specifically 6E-nerolidol. Allyl alcohols of the formula (II.2) which are particularly preferred in accordance with the invention are geraniol and farnesol.

If the compounds of the formulae (II.1) and (II.2) have one or more centers of asymmetry, it is also possible to use enantiomer mixtures or diastereomer mixtures. The process of the invention can be conducted with a mixture of the compounds of the formulae (II.1) and (II.2).

According to the invention, the process is executed according to variant 1 in which an allyl alcohol selected from compounds of the general formulae (II.1) and (II.2) is used for the reaction, in the presence of a compound A). Useful compounds A) preferably include the anhydrides of linear or branched monobasic $C_1$-$C_{12}$-alkanecarboxylic acids. Examples of such anhydrides are acetic anhydride, propionic anhydride, isopropionic anhydride, butyric anhydride, n-valeric anhydride, the mixed anhydride of formic acid and acetic acid, and the like. Especially preferred are the symmetric anhydrides of the alkanemonocarboxylic acids having up to 5 carbon atoms. Likewise suitable are the anhydrides of linear or branched monobasic $C_3$-$C_{12}$-alkenecarboxylic acids. Examples of these are (meth)acrylic anhydride, crotonic anhydride and isocrotonic anhydride. Likewise suitable are the anhydrides of linear or branched dibasic $C_4$-$C_{20}$-alkanecarboxylic acids, for example the anhydride of succinic acid, glutaric acid, adipic acid, pimelic acid, suberic acid, azelaic acid, sebacic acid, undecanedioic acid, dodecanedioic acid, brassylic acid, tetradecanedioic acid, pentadecanedioic acid, hexadecanedioic acid, heptadecanedioic acid, octadecanedioic acid. Likewise suitable are the anhydrides of linear or branched dibasic $C_4$-$C_{20}$-alkenecarboxylic acids, for example maleic anhydride or itaconic anhydride. Likewise suitable are the anhydrides of cycloaliphatic $C_7$-$C_{20}$-dicarboxylic acids such as cyclopentanedicarboxylic anhydride or cyclohexanecarboxylic anhydride. Likewise suitable are the anhydrides of aromatic $C_8$-$C_{20}$-dicarboxylic acids, such as phthalic anhydride, 1,8-naphthalenecarboxylic anhydride or 2,3-naphthalenecarboxylic anhydride. Particular preference is given to using acetic anhydride, propionic anhydride, isopropionic anhydride, butyric anhydride, succinic anhydride, maleic anhydride or phthalic anhydride, especially acetic anhydride.

Suitable compounds A) are likewise the esters of the formulae (III.1) and (III.2). In the process of the invention, it does not matter whether the double bond is arranged in a terminal position (compound of the formula (III.1)) or whether the double bond is arranged in an internal position (compound of the formula (III.2)). Therefore, it is also possible to use a mixture of compounds of the formulae (III.1) and (III.2). In general, however, no mixture of the compounds of the formulae (III.1) and (III.2) is used.

Preference is given to compounds of the formulae (III.1) and (III.2) in which the $R^3$ and $R^4$ radicals are the same or different and are hydrogen, linear or branched $C_1$-$C_{16}$-alkyl, linear or branched $C_2$-$C_{16}$-alkenyl having one or two nonconjugated double bonds, or $R^3$ and $R^4$ together with the carbon atom to which they are bonded are unsubstituted $C_5$-$C_7$-cycloalkyl or $C_5$-$C_7$-cycloalkyl bearing 1, 2 or 3 linear or branched $C_1$-$C_6$-alkyl radicals. Alternatively, in the compounds of the formulae (III.1) and (III.2), $R^3$ and $R^4$ together with the carbon atom to which they are bonded are preferably unsubstituted $C_5$-$C_7$-cycloalkyl. In the compounds of the formulae (III.1) and (III.2), $R^5$ is preferably hydrogen or $C_1$-$C_4$-alkyl. Specifically, $R^5$ is $C_1$-$C_2$-alkyl. Particular preference is given to allyl acetate.

Likewise preferred as compound A) is an ester of the formula (III.1) or (III.2) which derives from the alcohol of the formula (II.1) or (II.2) used as reactant for the carbonylation. Esters of the formula (III.1) that are particularly preferred in accordance with the invention are esters of a linear or branched monobasic $C_1$-$C_3$-alkanecarboxylic acid and an alcohol selected from 3-methyl-1-penten-3-ol, 1-hepten-3-ol, 1-vinylcyclohexanol, linalool and nerolidol. Especially preferred are linaloyl acetate and nerolidyl acetate, specifically 6E-nerolidyl acetate. A compound of the formula (III.2) which is particularly preferred in accordance with the invention is farnesyl acetate.

If the compounds of the formulae (III.1) and (III.2) have one or more centers of asymmetry, it is also possible to use enantiomer mixtures or diastereomer mixtures.

In variant 1, in which an allyl alcohol selected from compounds of the general formulae (II.1) and (II.2) is used for the reaction, the carbonylation is effected in accordance with the invention in the presence of a substoichiometric amount, based on the allyl alcohol used, of a compound A), i.e. the molar amount of compound A) is less than the molar amount of allyl alcohol. The molar ratio of compound A) to the allyl alcohol selected from compounds of the formulae (II.1) and (II.2) is typically in the range from 0.001:1 to about 0.95:1. Preferably, the total amount of the compound A) is not more than 50 mol %, preferably not more than 40 mol %, preferably not more than 30 mol %, based on the total molar amount of the compounds (II.1) and (II.2). Molar ratios in the range from 0.1:1 to 0.35:1 and specifically from 0.15:1 to 0.30:1 are particularly preferred.

In the processes of the invention for preparation of the carboxylic acid of the formula (I), the effect of the added anhydride is equivalent to the effect of the acylated allyl alcohol of the formulae (III.1) and (III.2) added.

In addition, it may be appropriate to conduct the carbonylation according to variant 1 in the presence of a nucleophilic reagent. Examples of nucleophilic reagents are 4-($C_1$-$C_4$-alkyl)pyridines, 4-(1-pyrrolidinyl)pyridine and 4-(di($C_1$-$C_4$-alkyl)amino)pyridine. Suitable 4-($C_1$-$C_4$-alkyl)pyridines are 4-methylpyridine and 4-ethylpyridine. Suitable 4-(di($C_1$-$C_4$-alkyl)amino)-pyridines are 4-(dimethylamino)pyridine and 4-(diethylamino)pyridine, especially 4-dimethylaminopyridine. Typically, the nucleophilic reagent selected from 4-($C_1$-$C_4$-alkyl)pyridine, 4-(1-pyrrolidinyl)pyridine and 4-(di($C_1$-$C_4$-alkyl)amino)pyridine is used in an amount of 0.01 to 5 mol %, preferably of 0.05 to 2 mol %, especially of 0.1 to 1 mol %, based on the total molar amount of the compounds (II.1) and (II.2).

The remarks which follow relating to the preparation of a composition comprising at least one unsaturated carboxylic acid of the general formula (I) relate to all variants of the process of the invention (variant 1, variant 2 and variant 3), unless explicitly stated otherwise.

In all variants, the upper limit for the amount of carbon monoxide is determined by economic reasons, although the use of an excess amount does not adversely affect the reaction. Advantageously, carbon monoxide is used in excess. Carbon monoxide is usually used in an amount of at least 1.1 mol per total molar amount of the compounds (II.1) and (II.2) or per total molar amount of the compounds (IV.1) and (IV.2).

The carbonylation (by all variants) is effected in accordance with the invention in the presence of a transition metal catalyst comprising at least one metal of group 8, 9 or 10 of the Periodic Table of the Elements. Transition metals used are preferably palladium, ruthenium, rhodium, iridium and iron, more preferably palladium.

Typically, the transition metal catalyst is used in an amount of not more than 0.5 mol %, in particular 0.001 to 0.3 mol %, based on the total amount of the compounds (II.1) and (II.2) or based on the total amount of the compounds (IV.1) and (IV.2).

According to the invention, at least one organic phosphorus compound is additionally used as ligand. Suitable organic phosphorus compounds are monodentate and bidentate phosphorus ligands. The nature of the organic phosphorus compound is unimportant in principle, and so it is generally advisable to use inexpensive tertiary monodentate phosphines of the formula (V)

(V)

in which
$R^7$, $R^8$ and $R^9$ are independently selected from unsubstituted and substituted alkyl, unsubstituted and substituted cycloalkyl, unsubstituted and substituted heterocyclyl, unsubstituted and substituted aryl and unsubstituted and substituted hetaryl.

Preferably, $R^7$, $R^8$ and $R^9$ are independently
$C_1$-$C_{16}$-alkyl which is unsubstituted or substituted by phenyl;
$C_5$-$C_8$-cycloalkyl which is unsubstituted or substituted by 1, 2 or 3 $C_1$-$C_6$-alkyl radicals;
$C_6$-$C_{10}$-aryl which is unsubstituted or substituted by 1, 2 or 3 $C_1$-$C_6$-alkyl radicals, $C_1$-$C_6$-alkoxy radicals, di($C_1$-$C_4$-dialkyl)amino, $SO_3H$ or $SO_3M$ where M is Li, Na, K, $NH_4$;
$C_6$-$C_{10}$-aryl substituted by 1, 2 or 3 radicals selected from fluorine, chlorine and $C_1$-$C_{10}$-fluoroalkyl;
5- or 6-membered saturated heterocyclyl comprising, as well as carbon atoms, a nitrogen atom or an oxygen atom as ring member;
$C_5$-$C_8$-Cycloalkyl; or
5- or 6-membered hetaryl comprising, as well as carbon atoms, a heteroatom selected from nitrogen and oxygen.

Examples of preferred phosphines of the formula (V) are trialkylphosphines, triarylphosphines, dialkylarylphosphines, alkyldiarylphoshines, cycloalkyldiaryiphosphines, dicycloalkylarylphosphines, and tricycloalkylphosphines.

Examples of preferred phosphines of the formula (V) are likewise triheterocyclylphosphines and trihetarylphosphines. Examples of preferred trialkylphosphines are triethylphosphine, tri-n-butylphosphine, tri-tert-butylphosphine, tribenzylphosphine, etc. Examples of preferred tricycloalkylphosphines are tri(cyclopentyl)phosphine, tri(cyclohexyl)phosphine, etc. Examples of preferred triarylphosphines are triphenylphosphine, tri(p-tolyl)phosphine, tri(m-tolyl)phosphine, tri(o-tolyl)phosphine, tri(p-methoxyphenyl)phosphine, tri(p-dimethylaminophenyl)phosphine, tri(sodium meta-sulfonatophenyl)phosphine, diphenyl(2-sulfonatophenyl)phosphine, tri(1-naphthyl)phosphine and diphenyl-2-pyridylphosphine. Examples of preferred dialkylarylphosphine are dimethylphenylphosphine and di-tert-butylphenylphosphine. Examples of preferred alkyldiarylphosphines are ethyldiphenylphosphine and isopropyldiphenylphosphine. One example of preferred cycloalkyldiaryiphosphine is cyclohexyldiphenylphosphine. One example of preferred dicycloalkylarylphosphine is dicyclohexylphenylphosphine. Further examples of preferred triarylphosphines are tri(o-methoxyphenyl)phosphine, tri(m-methoxyphenyl)phosphine, tri(p-fluorophenyl)phosphine, trim-fluorophenyl)phosphine, tri(o-fluorophenyl)phosphine, tri(p-chlorophenyl)phosphine, tri (m-chlorophenyl)phosphine, tri(pentafluorophenyl)phosphine, tris(p-trifluoromethylphenyl)phosphine, tri[3,5-bis(trifluoromethyl)phenyl]phosphine, diphenyl(o-methoxyphenyl)phosphine, diphenyl(o-methylphenyl)phosphine, tris(3,5-dimethylphenyl)phosphine and tri-2-naphthylphosphine. One example of preferred trihetarylphosphine is tri(o-furyl)phosphine. A further example of preferred trialkylphosphine is triisobutylphosphine. One example of preferred trihetercyclylphosphine is tris(1-pyrrolidinyl)phosphine. Especially preferred are triphenylphosphine, di-tert-butylphenyiphosphine, cyclohexyldiphenylphosphine, dicyclohexylphenylphosphine, tri(p-tolyl)phosphine and tri(cyclohexyl)phosphine.

Suitable bidentate phosphine ligands are 2,2'-bis(diphenylphosphino)-1,1'-binaphthyl (BINAP), 2-bis(diphenylphosphino)ethane (DPPE), 1,3-bis(diphenylphosphino)propane (DPPP), 1,4-bis(diphenylphosphino)butane (DPPB), 1,1'-bis(diphenylphosphino)ferrocene (DPPF), 4,5-bis(diphenylphosphino)-9,9-dimethylxanthene (Xantphos), 1,2-bis(di-tert-butylphosphinomethyl)benzene, 1,2-bis(di-tert-pentylphosphinomethyl)benzene and 1,2-bis(di-tert-butylphosphinomethyl)naphthalene.

In addition, it may be appropriate to conduct the reaction in the presence of phosphine of the formula (V) in free form, i.e. not bound within the complex, and/or bidentate phosphines.

The molar ratio of organic phosphorus compound to transition metal is typically 1:1 to 10:1, preferably 2:1 to 5:1, Specifically, the molar ratio of organic phosphorus compound of the formula (V) to transition metal is typically 1:1 to 10:1, preferably 2:1 to 5:1.

It is advantageous to conduct the carbonylation with exclusion of or with a reduced content of atmospheric oxygen.

In addition to the organic phosphorus compounds described as ligand above, the carbonylation catalysts used in accordance with the invention may also include at least one further ligand preferably selected from halides, amines, acetate, carboxylates, acetylacetonate, aryl- or alkylsulfonates, hydride, CO, olefins, dienes, cycloolefins, nitriles, N-containing heterocycles, aromatics and heteroaromatics, ethers and monodentate phosphinite, phosphonite, phosphoramidite and phosphite ligands. Particularly suitable further ligands are carbonyl, acetate, acetylacetonate and cycloolefins such as cyclooctadiene or norbornadiene. Halides are likewise suitable, specifically chlorides and bromides.

Suitable transition metal sources are quite generally transition metals, transition metal compounds and transition metal complexes, from which the carbonylation catalyst is formed in situ under the carbonylation conditions in the reaction zone.

Suitable compounds of the transition metals mentioned are especially those that are soluble in the reaction medium chosen, for example salts or complexes with suitable ligands, for example carbonyl, acetylacetonate, hydroxyl, cyclooctadiene, norbornadiene, cyclooctene, methoxy, acetyl or other aliphatic or aromatic carboxylates. Transition metal compounds that are preferred in the context of the process of the invention are Ru(II), Ru(III), Ru(IV), Ru(0), Rh(I), Rh(III), Rh(0), Ir(I), Ir(III), Ir(IV), Ir(0) compounds, Pd(II), Pd(IV), Pd(0), Pt(II), Pt(IV), Pt(0) compounds and Fe(II) and Fe(III) compounds.

Suitable ruthenium salts are, for example, ruthenium(III) chloride, ruthenium(IV) oxide, ruthenium(VI) oxide or ruthenium(VIII) oxide, alkali metal salts of the ruthenium-oxygen acids, such as $K_2RuO_4$ or $KRuO_4$, or complexes of ruthenium. These include the metal carbonyls, such as trisruthenium dodecacarbonyl or hexaruthenium octadecacarbonyl, or mixed forms in which CO has been partly replaced by ligands of the formula $PR^7R^8R^9$, such as $Ru(CO)_3(P(C_6H_5)_3)_2$ or tris(acetylacetonato)ruthenium(III).

Examples of transition metal sources for suitable palladium compounds or complexes include palladium(II) acetate, palladium(II) chloride, palladium(II) bromide, palladium(II) nitrate, palladium(II) acetylacetonate, palladium (0) dibenzylideneacetone complex, tetrakis(triphenylphosphine)palladium(0), bis(tri-o-tolylphosphine)palladium(0), palladium(II) propionate, bis(triphenylphosphine)palladium (II) dichloride, palladium(II) nitrate, bis(acetonitrile)palladium(II) dichloride, bis(benzonitrile)palladium(II) dichloride.

Examples of rhodium compounds or complexes suitable as transition metal source include rhodium(II) and rhodium (III) salts, such as rhodium(II) or rhodium(III) carboxylate, rhodium(II) and rhodium(III) acetate, etc. Additionally suitable are rhodium complexes, such as rhodium biscarbonyl acetylacetonate, acetylacetonatobisethylenerhodium(I), acetyl-acetonatocyclooctadienylrhodium(I), acetylacetonatonorbornadienylrhodium(I), acetyl-acetonatocarbonyltriphenylphosphinerhodium(I), $Rh_4(CO)_{12}$, $Rh_6(CO)_{18}$ etc.

Iron compounds suitable as transition metal source are $Fe_2(CO)_{10}$, $Fe_2(CO)_9$, tris(acetylacetonato)iron(III).

The catalyst used may be homogeneously dissolved in the liquid reaction medium or, in the case of a polyphasic reaction, may be dissolved in the liquid phase of the reaction medium as what is called a homogeneous catalyst, or may be in supported or unsupported form as what is called a heterogeneous catalyst.

If the conversion is effected in the absence of further coreactants, the acid of the formula (I) is obtained. The acid of the formula (I) obtained can be removed from the reaction mixture by methods known per se to those skilled in the art, for example by distillation, and the remaining catalyst can be utilized in further reactions. The acid of the formula (I) can also be obtained by extracting from the reaction mixture.

The carbonylation can (in all variants) be conducted in the presence or absence of a base. The base is different than the nucleophilic reagent. Suitable bases are inorganic and organic bases. Examples of preferred inorganic bases are alkali metal carbonates and alkaline earth metal carbonates. Preferred alkali metals are sodium and potassium, particular preference being given to sodium. Preferred alkaline earth metals are magnesium and calcium. Suitable bases are likewise organic bases other than the nucleophilic reagent which is selected from 4-($C_1$-$C_4$-alkyl)pyridine, 4-(1-pyrrolidinyl)pyridine and 4-(di-($C_1$-$C_4$-alkyl)amino)pyridine such as 4-(dimethylamino)pyridine. The presence of the base, for example an additional amine, promotes the formation of the salt of the carboxylic acid of the general formula (I), such that the conversion rate is distinctly improved. In addition, acids which form from the anhydrides under the reaction conditions are neutralized or buffered by the base. It is possible in turn to generate the free acid from the salts of the carboxylic acid of the formula (I) by thermal means, for example by distillation of the reaction output, or by acidifying. Preference is given to effecting the carbonylation in the presence of an amine other than the nucleophilic reagent such as 4-(dimethylamino)pyridine. More particularly, a tertiary amine or a basic N-heteroaromatic is used.

Examples of the tertiary amine comprise a trialkylamine, specifically a tri($C_1$-$C_{15}$-alkyl)amine such as trimethylamine, triethylamine, tripropylamine, tributylamine, trihexylamine, trioctylamine, tridecylamine, N,N-dimethylethylamine, dimethylpropylamine or 1,4-diaza-bicyclo[2.2.2]octane (DABCO); an aromatic amine such as dimethylaniline or tribenzylamine; a cyclic amine such as N-methylpyrrolidine, N-methylpiperidine, N-methylmorpholine, N,N'-dimethylpiperazine. Among these, preference is given to a trialkylamine, such as triethylamine. Likewise suitable are N-heteroaromatics such as pyridine, N-methylimidazole or quinoline. The base other than the nucleophilic reagent selected from 4-($C_1$-$C_4$-alkyl)pyridine, 4-(1-pyrrolidinyl) pyridine and 4-(di-($C_1$-$C_4$-alkyl)amino)pyridine such as 4-(dimethylamino)-pyridine, is typically used in an amount of 0.8 mol to 1.2 mol per mole of the compound (I).

Especially in the case of carbonylation in the presence of an amine, acidification of the reaction mixture and extraction is a suitable method of obtaining the free acid. Alternatively, the free acid can be separated from the reaction mixture by distillation, since the salt of the unsaturated acid of the formula (I) breaks down under the action of heat to give the free unsaturated acid of the formula (I) and the amine, The carbonylation (in all variants) can be effected in the presence or absence of an added inert solvent. Inert solvents are understood to mean solvents that do not react chemically under the reaction conditions with the compounds used, i.e. the reactants, the products and the catalysts. Suitable inert solvents are aprotic organic solvents, for example aromatic hydrocarbons such as toluene or xylenes, alicyclic hydrocarbons such as cyclohexane, and cyclic ethers such as tetrahydrofuran or dioxane. For practical reasons, the carbonylation is preferably conducted in the absence of an inert solvent. If the reactant used, however, is sparingly soluble under the reaction conditions, the use of a solvent is advisable.

The carbonylation can be conducted continuously, semi-continuously or batchwise.

The pressure (in all variants) can be chosen within a wide range such as from atmospheric pressure to not more than 90 bar, preferably to not more than 30 bar, more preferably to not more than 25 bar, more preferably not more than 20 bar and especially not more than 15 bar. Suitable pressure ranges are, for example, 1.1 to 90 bar, 1.1 to 30 bar, 2 to 20 bar, 5 to 15 bar.

The reaction temperature (in all variants) can be chosen within a wide range from room temperature (25° C.) to 100° C., but it is preferably not more than 80° C., especially not more than 75° C.

In a specific embodiment of the process of the invention, the carbonylation is effected at a temperature of not more than 90° C. and at a pressure of not more than 20 bar.

Suitable pressure-resistant reactors are likewise known to those skilled in the art and are described, for example, in Ullmanns Enzyklopädie der technischen Chemie [Ullmann's Encyclopedia of Industrial Chemistry], vol. 1, 3rd edition, 1951, p. 769 ff. In general, an autoclave which may be provided if desired with a stirrer apparatus and an inner lining is used for the process of the invention.

The catalysts used in accordance with the invention can be separated from the output of the carbonylation reaction by customary methods known to those skilled in the art and can be reused for a carbonylation.

The reaction mixture can be subjected to a workup by customary methods known to those skilled in the art. For this purpose, the reaction mixture obtained in the carbonylation can be subjected to at least one workup step for removal of at least one of the following components:
- carbonylation catalyst,
- unconverted compounds of the formulae (II.1) and (II.2) or (IV.1) and (IV.2),
- reaction products other than the compounds of the formula (I),
- solvents.

A further embodiment of the present invention (variant 2) relates, as explained above, to the carbonylation of an acylated allyl alcohol selected from compounds of the formulae (IV.1) and (IV.2) to give the corresponding C1-extended unsaturated carboxylic acids of the formula (I) or a salt thereof, comprising the reaction of compounds selected from compounds of the formulae (IV.1) and (IV.2) with carbon monoxide in the presence of a transition metal catalyst comprising at least one metal of group 8, 9 or 10 of the Periodic Table of the Elements, wherein the reaction is additionally effected in the presence of at least one organic phosphorus compound as ligand and in the presence of water and wherein the reaction is effected at a temperature of not more than 100° C.

Compounds of the formulae (IV.1) and (IV.2) that are preferred in the context of the process of the invention are those in which the $R^1$ and $R^2$ radicals are the same or different and are hydrogen, linear or branched $C_1$-$C_{16}$-alkyl, linear or branched $C_2$-$C_{16}$-alkenyl having one or two nonconjugated double bonds, or $R^1$ and $R^2$ together with the carbon atom to which they are bonded are unsubstituted $C_5$-$C_7$-cycloalkyl or $C_5$-$C_7$-cycloalkyl bearing 1, 2 or 3 linear or branched $C_1$-$C_6$-alkyl radicals.

Especially preferred are compounds of the formulae (IV.1) and (IV.2) with terpene-like hydrocarbyl radicals. $R^1$ is preferably linear or branched $C_6$-$C_{16}$-alkyl or linear or branched $C_6$-$C_{16}$-alkenyl having one or two nonconjugated double bonds. $R^2$ is preferably hydrogen or $C_1$-$C_4$-alkyl, especially $C_1$-$C_2$-alkyl. $R^6$ is preferably $C_1$-$C_2$-alkyl. Particular preference is given in accordance with the invention to esters of a linear or branched monobasic $C_1$-$C_3$-alkanecarboxylic acid and of an allylic alcohol selected from 3-methy-1-penten-3-ol, 1-hepten-3-ol, 1-vinylcyclohexanol, linalool and nerolidol. Particular preference is given in accordance with the invention to linaloyl acetate and nerolidyl acetate, specifically 6E-nerolidyl acetate. A compound of the formula (IV.2) which is particularly preferred in accordance with the invention is farnesyl acetate.

If the compounds of the formulae (IV.1) and (IV.2) have one or more centers of asymmetry, it is also possible to use enantiomer mixtures or diastereomer mixtures. The process of the invention can be conducted with a mixture of the compounds of the formulae (IV.1) and (IV.2). However, preference is given to using a compound either of the formula (IV.1) or of the formula (IV.2).

Compounds of the formula (IV.1) are obtainable, for example, by esterifying carboxylic acids of the formula $R^6$—C(O)OH with the allyl alcohol of the formula (II.1), and compounds of the formula (IV.2), for example, by esterifying carboxylic acids of the formula $R^6$—C(O)OH with the allyl alcohol of the formula (II.2).

According to the invention, the carbonylation is effected in the presence of water. The molar ratio of water to the total molar amount of compounds of the formulae (IV.1) and (IV.2) is typically in the range from 1:1 to 10:1, but preferably in the range from 1.1:1 to 3:1.

With regard to suitable transition metal catalysts, suitable organic phosphorus compounds as ligand, reaction temperature, reaction pressure, reaction time, use of solvent, use of a nucleophilic reagent, use of bases other than the nucleophilic reagent, specifically the use of amines other than 4-(dimethylamino)pyridine and reaction apparatuses, reference is made to the above statements.

A further embodiment of the present invention (variant 3) relates, as stated above, to the carbonylation of compounds of the general formulae (II.1) and (II.2) to give the corresponding C-1-extended unsaturated carboxylic acids of the formula (I) or a salt thereof, comprising the reaction of compounds selected from compounds of the formulae (II.1) and (II.2) with carbon monoxide in the presence of a transition metal catalyst comprising at least one metal of groups 8, 9 and 10 of the Periodic Table of the Elements, wherein the reaction is additionally effected in the presence of at least one organic phosphorus compound as ligand and in the presence of a substoichiometric amount, based on the allyl alcohol, of a compound B), and wherein the reaction is effected at a temperature of not more than 100° C. In the compounds B, $R^{10}$ and $R^{11}$ preferably have the same meaning. Useful compounds B) preferably include methanesulfonic anhydride, trifluoromethanesulfonic anhydride, phenylsulfonic anhydride, p-toluenesulfonic anhydride, 4-bromophenylsulfonic anhydride and 4-nitrophenylsulfonic anhydride.

In variant 3, in which an allyl alcohol selected from compounds of the general formulae (II.1) and (II.2) is used for reaction, the carbonylation, according to the invention, is effected in the presence of a substoichiometric amount, based on the allyl alcohol used, of a compound B), meaning that the molar amount of compound B) is less than the molar amount of allyl alcohol. The molar ratio of compound B) to the allyl alcohol selected from compounds of the formulae (II.1) and (II.2) is typically in the range from 0.001:1 to about 0.95:1. Preferably, the total amount of the compound B) is not more than 50 mol %, preferably not more than 40 mol %, based on the total molar amount of the compounds (II.1) and (II.2). Molar ratios in the range from 0.1:1 to 0.35:1 and especially from 0.15:1 to 0.30:1 are particularly preferred.

In the processes of the invention for preparing the carboxylic acid of the formula (I) by variant 3, the effect of the added sulfonic anhydride is equivalent to the effect of the added compound A) in variant 1.

With regard to suitable transition metal catalysts, suitable organic phosphorus compounds as ligand, reaction temperature, reaction pressure, reaction time, use of solvents, use of nucleophilic agents, use of bases other than nucleophilic reagent, and reaction apparatuses, reference is made to the above statements.

The carbonylation by variant 3 is preferably effected at a temperature of not more than 100° C. and at a pressure of not more than 30 bar.

In the variants 1, 2 and 3 of the process of the invention, it is possible to obtain homofarnesylic acid proceeding from commercial substances, such as farnesol or nerolidol, in high yield under mild reaction conditions.

More particularly, the process of the invention is suitable for preparing E/Z-4,8-dimethyl-3,7-nonadienoic acid from linalool under mild reaction conditions.

More particularly, the process of the invention is likewise suitable for preparation of (3E,7E)-4,8,12-trimethyltrideca-3,7,11-trienoic acid or a salt thereof and (3Z,7E)-4,8,12-trimethyltrideca-3,7,11-trienoic acid or a salt thereof in a weight ratio of 80:20 to 50:50, preferably of 70:30 to 55:45, proceeding from E-nerolidol. The proportion of (3E,7E)-4,8,12-trimethyltrideca-3,7,11-trienoic acid in the isomer mixtures obtained is generally higher than the proportion of (3E,7E)-4,8,12-trimethyltrideca-3,7,11-trienoic acid. The composition obtained can be subjected to an at least partial enrichment of one isomer.

In the processes according to variants 1, 2 and 3, in general, E/Z isomer mixtures of the formula (I) or salts thereof are obtained when $R^1$ and $R^2$ in formula (I) have different meanings. The E/Z isomer mixtures of the formula (I) comprise a 3-(E) acid of the formula (I-E) and a 3-(Z) acid of the formula (I-Z)

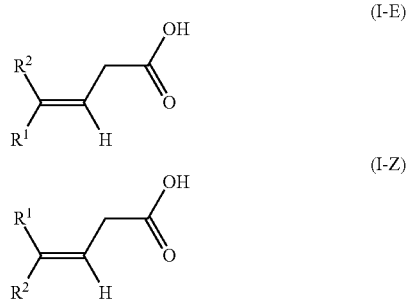

in which $R^1$ and $R^2$ have different definitions and $R^1$ has a higher priority according to IUPAC.

Frequently, just one of the two isomers is the product of value. Preference is given to subjecting the E/Z isomer mixture of the formula (I) which is obtained by the process of the invention to an at least partial enrichment of one isomer. A possible isomer separation of such a mixture for partial enrichment of one isomer can be effected by chromatography or distillation or as described in EP 17157974.1.

The product of value is frequently the 3-(E) acid of the formula (I-E), and not the 3-(Z) acid of the formula (I-Z) which is likewise obtained in significant amounts.

It would therefore be economically advisable first to separate at least a portion of the 3-(E) acid of the formula (I-E) from the composition obtained in accordance with the invention comprising the E/Z isomer mixture of the formula I, and to convert the unwanted 3-(Z) acid of the formula (I-Z) at least partly to the product of value, i.e. to the 3-(E) acid of the formula (I-E).

Therefore, in a preferred embodiment of the present invention, the process of the invention for preparing an E/Z isomer mixture of the formula (I) comprises the following additional steps:

(1) the composition comprising the E/Z isomer mixture of the formula (I), in the presence of an alcohol and of a lipase enzyme, is subjected to an enzyme-catalyzed esterification, wherein the 3-(E) acid of the formula (I-E) is converted at least partly to a 3-(E) ester, so as to obtain a composition comprising the 3-(E) ester, unconverted 3-(E) acid of the formula (I-E) and unconverted 3-(Z) acid of the formula (I-Z);

(2) the composition obtained in (1) is separated to obtain a composition depleted of 3-(E) acid of the formula (I-E) and enriched in 3-(Z) acid of the formula (I-Z), and to obtain a composition comprising the 3-(E) ester, (3) the composition obtained in (2) which is depleted of 3-(E) acid of the formula (I-E) and enriched in 3-(Z) acid of the formula (I-Z) is subjected to an isomerization to increase the content of 3-(E) acid of the formula (I-E), and (4) optionally, the 3-(E) ester obtained in (2) is cleaved to obtain the 3-(E) acid of the formula (I-E).

Processes for enzymatically catalyzed esterifications of a mixture of 3-(E)-unsaturated carboxylic acid and 3-(Z)-unsaturated carboxylic acid with an alcohol are known, for example, from EP 17157974.1.

Many lipases are capable of catalyzing esterifications with high substrate selectivity. Preferably, the lipase is *Candida antarctica* lipase (CALK) or a form immobilized on a polymeric carrier, such as Novozym 435®. The enzyme-catalyzed esterification is preferably effected in the presence of an aliphatic alcohol. Suitable aliphatic alcohols are $C_1$-$C_{20}$-alkanols such as methanol, ethanol, n-propanol, isopropanol, n-butanol, isobutanol, sec-butanol, n-pentanol, n-hexanol, n-heptanol and n-octanol. The enzyme-catalyzed esterification can optionally be conducted in the presence of a diluent or solvent. Examples of suitable diluents or solvents are especially aliphatic hydrocarbons such as hexane, cyclohexane, heptane, octane; aromatic hydrocarbons, for example toluene, xylene; dialkyl ethers such as methyl tert-butyl ether and diisopropyl ether. Typically 1-5 equivalents of alcohol are used per equivalent of 3-(E) acid. The esterification is typically conducted at a temperature within a range from 0 to 80° C.

The lipase esterifies the 3-(E) acid of the formula (I-E) with alcohols very much more quickly than the corresponding 3-(Z) acid of the formula (I-Z). Therefore, a separable composition is obtained, comprising the 3-(E) ester, unconverted 3-(E) acid of the formula (I-E) and unconverted 3-(Z) acid of the formula (I-Z).

The composition obtained in step (1) can be separated by extraction or distillation.

In step (4), the 3-(E) ester isolated in step (2) is optionally subjected to an acid-, base- or enzyme-catalyzed ester cleavage to obtain the 3-(E) acid of the formula (I-E) or salt thereof. Since the compound of the formula (I-E) is frequently the product of value, it is appropriate to conduct the ester cleavage.

In a further preferred embodiment, the process of the invention for preparing an E/Z isomer mixture of the formula (I) comprises the following additional steps:
(i) the composition comprising the E/Z isomer mixture of the formula (I) is subjected to an esterification in the presence of an alcohol to obtain the 3-(E) ester and the 3-(Z) ester;
(ii) the 3-(E) ester and the 3-(Z) ester obtained in (i) are subjected to a lipase-catalyzed enzymatic hydrolysis, wherein the lipase at least partly cleaves the 3-(E) ester to give the 3-(E) acid of the formula (I-E) to obtain a composition comprising the 3-(E) acid of the compound of the formula (I-E), unconverted 3-(E) ester and unconverted 3-(Z) ester;
(iii) the composition obtained in (ii) is separated to obtain a composition comprising the 3-(E) acid of the compound of the formula (I-E) and to obtain a composition comprising unconverted 3-(E) ester and unconverted 3-(Z) ester;
(iv) the composition which is obtained in (iii) and comprises unconverted 3-(E) ester and unconverted 3-(Z) ester is subjected to an ester cleavage to obtain a composition depleted of 3-(E) acid of the formula (I-E) or salt thereof and enriched in 3-(Z) acid of the formula (I-Z) or salt thereof; and
(v) the composition which is obtained in (iv) and is depleted of 3-(E) acid of the formula (I-E) and enriched in 3-(Z) acid of the formula (I-Z) is subjected to an isomerization to increase the content of 3-(E) acid of the formula (I-E).

Preferably, the esterification in step (i) is effected with an aliphatic alcohol. Suitable aliphatic alcohols are $C_1$-$C_{20}$-alkanols such as methanol, ethanol, n-propanol, isopropanol, n-butanol, isobutanol, sec butanol, n-pentanol, n-hexanol, n-heptanol and n-octanol. The esterification can be conducted under acid, base or enzyme catalysis. The esterification is typically conducted at a temperature within a range from 0 to 80° C.

Processes for enzymatically catalyzed ester cleavage of a mixture of 3-(E)-unsaturated carboxylic acid and 3-(Z)-unsaturated carboxylic acid in the presence of water are known, for example, from EP 17157974.1.

Many lipases are capable of catalyzing ester cleavages with high substrate selectivity. In step (ii), the composition obtained in step (i), in the presence of water and a lipase enzyme, is subjected to an enzyme-catalyzed ester cleavage to obtain a composition comprising 3-(E) acid of the formula (I-E), unconverted 3-(E) ester and unconverted 3-(Z) ester. The lipases are preferably *Candida antarctica* lipase (CALB) or a form immobilized on a polymeric carrier, such as Novozym 435®.

The composition obtained in step (ii) can be separated by distillation or extraction. This gives a composition comprising 3-(E) acid of the formula (I-E). Likewise obtained is a composition comprising the 3-(E) ester and 3-(Z) ester.

The ester cleavage in step (iv) can be effected under acid, base or enzyme catalysis. This gives a composition comprising 3-(E) acid of the formula (I-E) or salt thereof and 3-(Z) acid of the formula (I-Z) or salt thereof, with a reduced content of 3-(E) acid of the formula (I-E) and an increased content of 3-(Z) acid of the formula (I-Z) compared to the composition used in step (i).

In steps (3) and (v) of the aforementioned processes, the composition obtained is subjected to an isomerization of the 3-(Z) acid of the formula (I-Z) to the 3-(E) acid of the formula (I-E) in order to increase the proportion of product of value. The isomerization is preferably effected in the presence of an anhydride of an organic acid and a base. Suitable anhydrides are anhydrides of aliphatic $C_1$-$C_{12}$ monocarboxylic acids, anhydrides of aliphatic $C_4$-$C_{20}$ dicarboxylic acids, anhydrides of cycloaliphatic $C_7$-$C_{20}$ dicarboxylic acids, anhydrides of aromatic $C_8$-$C_{20}$ dicarboxylic acids, anhydrides of aliphatic sulfonic acids and anhydrides of aromatic sulfonic acids. Suitable bases are alkali metal carbonates, alkaline earth metal carbonates, alkali metal hydrogencarbonates, alkaline earth metal hydrogencarbonates, alkali metal phosphates, alkaline earth metal phosphates, amines, basic N-heteroaromatics, basic ion exchangers and mixtures thereof. The isomerization is preferably effected in the presence of an anhydride of an organic acid and a base. The process can advantageously be conducted at a temperature of 60 to 175° C., preferably 70 to 160° C.

The pressure is uncritical. Therefore, the isomerization can be conducted at elevated pressure, reduced pressure or atmospheric pressure. When using a base and/or an anhydride having a boiling point below the reaction temperature at standard pressure, the process is appropriately conducted in a pressure reactor. Advantageously, the isomerization can also be conducted under the conditions of the process of the invention. Advantageously, the presence of a transition metal catalyst is not required for the isomerization.

The compounds of the general formula (I) obtained by the process of the invention can be subjected to a reduction with conversion of the acid or ester group to the corresponding alcohols. In a specific embodiment, first of all, a mixture of (3E,7E)-4,8,12-trimethyltrideca-3,7,11-trienoic acid and (3Z,7E)-4,8,12-trimethyltrideca-3,7,11-trienoic acid, obtainable as described above, is subjected to a separation to obtain (3E,7E)-4,8,12-trimethyltrideca-3,7,11-trienoic acid, for example as described above, and (3E,7E)-4,8,12-trimethyltrideca-3,7,11-trienoic acid to a reduction to obtain (3E,7E)-homofarnesol (VI)

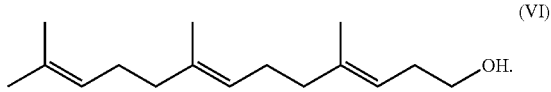 [SMILES: CC(C)=CCC/C(C)=C/CC/C(C)=C/CCO]

(VI)

(3E,7E)-Homofarnesol (VI) is likewise an important intermediate for preparation of aroma chemicals.

The invention further provides for the preparation of (−)-ambrox. The preparation can be effected by known methods proceeding from stereoisomerically pure (3E/7E)-homofarnesylic acid as shown in scheme 1 below.

Scheme 1

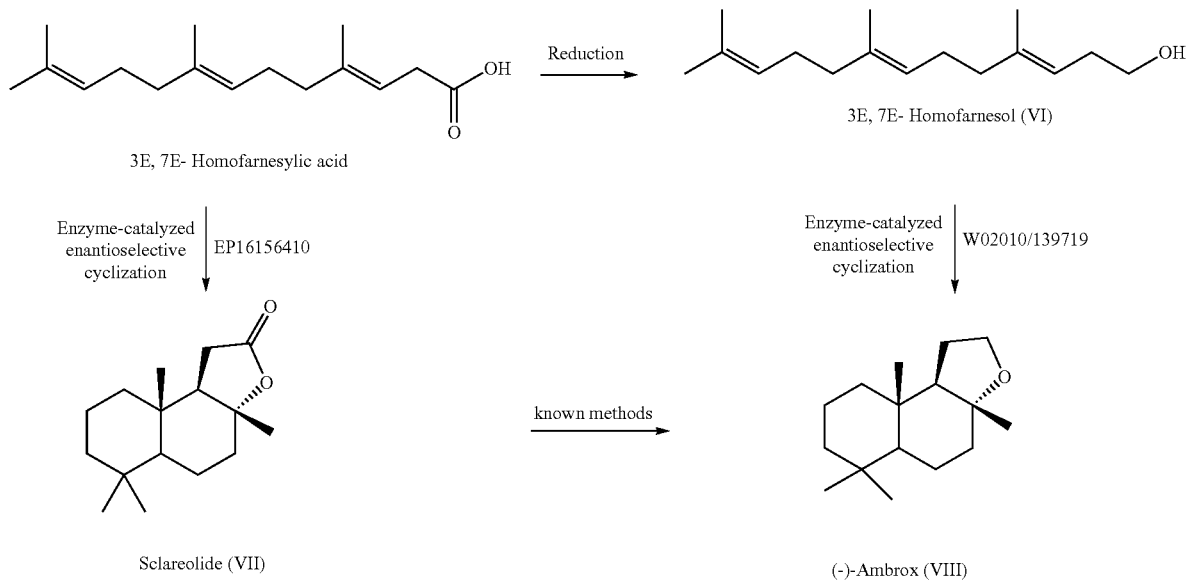

Reference is made here in full to the disclosure of EP 16156410, WO 2010/139719 and WO 2012/066059, which describe the biocatalytic cyclization of unsaturated substrates, for example of terpene-like hydrocarbons, using cyclase enzymes.

Sclareolide (VII) can be obtained, for example, by cyclase-catalyzed conversion of (3E/7E)-homofarnesylic acid prepared in accordance with the invention. Sclareolide (VII) can then be reduced chemically, for example by reaction with LiAlH$_4$ or NaBH$_4$, to obtain ambrox-1,4-diol (see Mookherjee et al.; Perfumer and Flavourist (1990), 15: 27). Ambrox-1,4-diol can then be converted further to (−)-ambrox by known methods.

Hydrogenation catalysts which enable good selectivity with respect to the hydrogenation of the terminal carboxylic acid group to obtain the corresponding alcohol are likewise known to those skilled in the art. The hydrogenation and isomerization of the double bonds present in the compounds (I) can essentially be avoided.

Likewise known is the cyclization of (3E,7E)-homofarnesol to ambrox, there being descriptions both of enzymatic and chemical cyclizations. In this regard, reference is made to the disclosure of the following documents:

P. F. Vlad et al. *Khimiya Geterotsiklicheskikh Soedinenii, Engl. Transl.* 1991, 746 describe cyclization reactions using a superacid (fluorosulfonic acid in 2-nitropropane). A further suitable method comprises the enantioselective polyene cyclization of homofarnesyl triethylsilyl ether in the presence of O-(o-fluorobenzyl)binol and SnCl$_4$, as described by H. Yamamoto et al. *J. Am. Chem. Soc.* 2002, 3647.

Preference is given to biocatalytic cyclization as described in WO 2010/139719. According to this, the cyclization in step d1) is effected in the presence of a polypeptide having the activity of a homofarnesol-ambrox cyclase as enzyme.

For preparation of (−)-ambrox by this variant, homofarnesol is contacted and/or incubated with the homofarnesol-ambroxan cyclase and then the ambrox formed is isolated.

In one embodiment, homofarnesol is contacted with the homofarnesol-ambroxan cyclase in a medium and/or incubated therewith such that homofarnesol is converted to ambrox in the presence of the cyclase. Preferably, the medium is an aqueous reaction medium. The aqueous reaction media are preferably buffered solutions that generally have a pH of preferably 5 to 8. The buffer used may be a citrate, phosphate, TRIS (tris(hydroxymethyl)aminomethane) or MES (2-(N-morpholino)ethanesulfonic acid) buffer. In addition, the reaction medium may comprise further additives, for example detergents (for example taurodeoxycholate).

The homofarnesol is preferably used in the enzymatic reaction in a concentration of 5 to 100 mM, more preferably of 15 to 25 mM. This reaction can be conducted continuously or batchwise.

The enzymatic cyclization is appropriately effected at a reaction temperature below the deactivation temperature of the cyclase used. The reaction temperature in step d1) is preferably within a range from −10 to 100° C., more preferably from 0 to 80° C., particularly from 15 to 60° C. and especially from 20 to 40° C.

The ambrox reaction product can be extracted with organic solvents and optionally distilled for purification. Suitable solvents are specified hereinafter.

As well as monophasic aqueous systems, it is also possible to use biphasic systems. In this variant, it is possible to enrich the ambrox formed in the nonaqueous phase in order to isolate it. The second phase here is preferably selected from ionic liquids and organic water-immiscible solvents. After the reaction, ambrox in the organic phase is easily separable from the aqueous phase comprising the biocatalyst. Nonaqueous reaction media are understood to mean reaction media comprising less than 1% by weight and preferably less than 0.5% by weight of water, based on the total weight of the liquid reaction medium. More particularly, the reaction can be conducted in an organic solvent. Suitable organic solvents are, for example, aliphatic hydrocarbons preferably having 5 to 8 carbon atoms, such as pentane, cyclopentane, hexane, cyclohexane, heptane, octane or cyclooctane, halogenated aliphatic hydrocarbons, preferably having one or two carbon atoms, such as dichloromethane, chloroform, carbon tetrachloride, dichloroethane or tetrachloroethane, aromatic hydrocarbons such as benzene, toluene, the xylenes, chlorobenzene or dichlorobenzene, aliphatic acyclic and cyclic ethers or alcohols, preferably having 4 to 8 carbon atoms, such as ethanol, isopropanol, diethyl ether, methyl tert-butyl ether, ethyl tert-butyl ether, dipropyl ether, diisopropyl ether, dibutyl ether, tetrahydrofuran, or esters such as ethyl acetate or n-butyl acetate, or ketones such as methyl isobutyl ketone or dioxane or mixtures thereof. Particular preference is given to using the aforementioned heptane, methyl tert-butyl ether, diisopropyl ether, tetrahydrofuran, ethyl acetate.

Suitable enzymes are described in WO 2010/139719, which is incorporated here by reference in full. According to this, the enzyme is a polypeptide encoded by a nucleic acid molecule comprising at least one nucleic acid molecule selected from:
  a) nucleic acid molecule which codes for a polypeptide comprising SEQ ID NO 2, 5, 6, 7, 8, 9, 10 or 11; b) nucleic acid molecule which comprises at least one polynucleotide of the sequence shown in SEQ ID NO 1; c) nucleic acid molecule which codes for a polypeptide whose sequence has an identity of at least 46% to the sequences SEQ ID NO 2, 5, 6, 7, 8, 9, 10 or 11; d) nucleic acid molecule according to (a) to (c) which is a functionally equivalent polypeptide or a fragment of the sequence according to SEQ ID NO 2, 5, 6, 7, 8, 9, 10 or 11; e) nucleic acid molecule coding for a functionally equivalent polypeptide with the activity of a homofarnesol-ambroxan cyclase which is obtained by amplifying a nucleic acid molecule from a cDNA bank or from genomic DNA by means of the primer according to sequence No. 3 and 4, or chemically synthesizing the nucleic acid molecule by de novo synthesis; f) nucleic acid molecule coding for a functionally equivalent polypeptide with the activity of a homofarnesol-ambroxan cyclase which hybridizes under stringent conditions with a nucleic acid molecule according to (a) to (c); g) nucleic acid molecule coding for a functionally equivalent polypeptide with the activity of a homofarnesol-ambroxan cyclase which can be isolated from a DNA bank using a nucleic acid molecule according to (a) to (c) or fragments thereof of at least 15 nt, preferably 20 nt, 30 nt, 50 nt, 100 nt, 200 nt or 500 nt as probe under stringent hybridization conditions; and h) nucleic acid molecule coding for a functionally equivalent polypeptide with the activity of a homofarnesol-ambroxan cyclase, where the sequence of the polypeptide has an identity of at least 46% to the sequences SEQ ID NO 2, 5, 6, 7, 8, 9, 10 or 11; i) nucleic acid molecule coding for a functionally equivalent polypeptide with the activity of a homofarnesol-ambroxan cyclase, where the polypeptide is encoded by a nucleic acid molecule selected from the group of those described in a) to h) and has been isolated, or can be isolated, by means of a monoclonal antibody; j) nucleic acid molecule coding for a functionally equivalent polypeptide with the activity of a homofarnesol-ambroxan cyclase, where the polypeptide has an analogous or similar binding site to a polypeptide encoded by a nucleic acid molecule selected from the group of those described in a) to h).

In spite of a multitude of existing aroma chemicals (fragrances and flavorings) and processes for preparation thereof, there is a constant need for novel components in order to be able to satisfy the multitude of properties desired for the extremely diverse fields of use and for simple synthesis routes in order to make them available. The process of the invention enables the effective preparation of compounds of the general formula (I) that can serve as synthesis units of interest in the provision of novel and already known aroma chemicals, such as (−)-ambrox. After hydrogenation of the acid function, it is possible to obtain alcohols which may in turn be synthesis units of interest and be suitable for use as surfactant alcohols The invention is elucidated in detail by the working examples which follow. The examples which follow demonstrate that the invention can be conducted advantageously with different reactants and transition metal catalysts.

Abbreviations $Ac_2O$ represents acetic anhydride; DMAP stands for 4-(dimethylamino)pyridine; eq. stands for equivalent(s); $Fe(acac)_3$ represents tris(acetylacetonato)iron(III); area % stands for area percent; GC stands for gas chromatography; $[Ir(COD)Cl]_2$ represents bis(1,5-cyclooctadiene)diiridium(I) dichloride; MTBE stands for methyl tert-butyl ether; $NEt_3$ represents triethylamine; org. stands for organic; $P(Cy)_3$ represents tricyclohexylphosphine; $Pd(acac)_2$ represents bis(acetylacetonato)palladium(II); $Pd(dba)_2$ represents bis(dibenzylideneacetone)palladium(0); $Pd(OAc)_2$ represents palladium(II) acetate; $Rh(CO)_2(acac)$ represents (acetylacetonato)dicarbonylrhodium(I); $Ru(acac)_3$ represents tris(acetylacetonato)ruthenium(III); Acid sel. stands for acid selectivity; THF stands for tetrahydrofuran; TPP stands for triphenylphosphine; rpm stands for revolutions per minute.

The products were identified with the aid of GC, $^1H$ NMR and $^{13}C$ NMR analysis. The workup of the reaction mixtures was not optimized.

Example 1: Pd-Catalyzed Carbonylation Proceeding from Linalool

Palladium(II) acetate (19 mg, 0.085 mmol), triphenylphosphine (51 mg, 0.195 mmol) and DMAP (49 mg, 0.4 mmol) were initially charged in a glass autoclave under argon. Linalool (10.8 g, 70 mmol), triethylamine (6.9 g, 68 mmol) and acetic anhydride (2 g, 20 mmol) were added in an argon counterflow. Subsequently, 10 bar CO was applied and the mixture was stirred at 1000 rpm at this pressure and at internal temperature 60° C. for 24 h. Thereafter, the mixture was cooled to room temperature and decompressed. GC analysis of the reaction output gave a conversion of 94% with a selectivity for the E/Z-4,8-dimethyl-3,7-nonadienoic acid target product of 62%.

After the reaction had ended, MTBE (25 mL) and aqueous NaOH (5%, 70 mL) were added. The phases were separated and the aqueous phase was washed with MTBE (2×50 mL). The aqueous phase was brought to pH=1 with $H_2SO_4$ (20%) and extracted with MTBE (3×50 mL). The organic phases from the acidic extraction were combined, washed to neutrality with water (3×70 mL) and dried over $MgSO_4$. After concentration, 7.1 g (56%) of E/Z-4,8-dimethyl-3,7-nonadienoic acid were obtained with an E/Z ratio of 55:45 ($^1H$ NMR). The NMR data correspond to the data of Snyder et al. Angew. Chem., 121, 2009, 8039. $^{13}C$ NMR ($CDCl_3$), E-homomyrcenylcarboxylic acid: 179.9, 139.5, 131.7, 125.1, 116.2, 40.2, 34.0, 27.2, 26.2, 18.0, 16.6; Z-homomyrcenylcarboxylic acid: 179.9, 139.5, 132.1, 124.8, 117.0, 34.0, 32.6, 27.0, 26.2, 23.7, 18.0.

Examples 1.1-1.12: Pd-Catalyzed Carbonylation Proceeding from Linalool

Example 1 was repeated. The feedstocks for carbonylation of linalool, the conversion after 24 h and the selectivity for the E/Z-4,8-dimethyl-3,7-nonadienoic acid target product are reported in table I.

TABLE I

Carbonylation of linalool

| Example | Transition metal compound/ (mol %) | TPP (mol %) | DMAP (mol %) | Ac$_2$O (mol %) | CO (bar) | Conversion after 24 h | Acid sel. (GC area %) |
|---|---|---|---|---|---|---|---|
| 1 | Pd(OAc)$_2$/0.12 | 0.28 | 0.6 | 28 | 10 | 94% | 62 |
| 1.1[a] | Pd(OAc)$_2$/0.12 | 0.28 | 0.6 | 28 | 10 | 56% | 79 |
| 1.2[b] | Pd(OAc)$_2$/0.12 | 0.28 | 0.6 | 28 | 10 | 27% | 66 |
| 1.3[c] | Pd(OAc)$_2$/0.12 | 0.28 | 0.6 | 28 | 10 | 41% | 47 |
| 1.4[d] | Pd(OAc)$_2$/0.12 | 0.28 | 0.6 | 28 | 10 | 30% | 50 |
| 1.5 | Pd(acac)$_2$/0.12 | 0.28 | 0.6 | 28 | 10 | 80% | 70 |
| 1.6 | Pd(dba)$_2$/0.12 | 0.28 | 0.6 | 28 | 10 | 75% | 60 |
| 1.7[e] | PdCl$_2$/0.15 | 0.28 | 0.3 | 28 | 10 | 69% | 58 |
| 1.8[f] | Pd(OAc)$_2$/0.12 | 0.28 | 0.3 | 28 | 10 | 40% | 44 |
| 1.9[g] | Pd(OAc)$_2$/0.12 | 0.28 | 0.3 | 28 | 10 | 77% | 63 |
| 1.10 | PdCl$_2$/0.15 | 0.28 | — | — | 10 | 0% | — |
| 1.11[f] | PdCl$_2$/0.15 | 0.28 | — | — | 10 | 14% | 6 |
| 1.12[f] | Pd(OAc)$_2$/0.12 | 0.28 | — | — | 10 | 3% | — |

[a] addition of 10 mL of pyridine rather than NEt$_3$;
[b] addition of 10 mL of THF rather than NEt$_3$;
[c] addition of 10 mL of toluene rather than NEt$_3$;
[d] addition of 10 mL of dioxane rather than NEt$_3$;
[e] 80° C. rather than 60° C.;
[f] addition of 10 mL of THF rather than NEt$_3$, 100° C. rather than 60° C.;
[g] addition of 10 mL of THF rather than NEt$_3$, 80° C. rather than 60° C.

Comparative example 1.10 shows that no conversion was achieved at 10 bar under the conditions of EP 0146859 (PdCl$_2$/TPP) in the absence of an anhydride source, and even at 100° C. very small conversions at most to the target product (comparative example 1.11). Comparative example 1.12 shows that only a minimal conversion was achieved in the case of use of Pd(OAc)$_2$ in the absence of an anhydride source.

Examples 1.13-1.17: Carbonylation Proceeding from Linalool Using Transition Metal Catalysts of Groups 8 and 9 of the Periodic Table Example 1 was repeated. The feedstocks for carbonylation of linalool, the conversion after 24 h and the selectivity for the target product (E/Z-4,8-dimethyl-3,7-nonadienoic acid) are reported in table II.

pressure and at internal temperature 60° C. for 24 h. Thereafter, the mixture was cooled to room temperature and decompressed. GC analysis of the reaction output gave a conversion of 70% with a selectivity for the E/Z-(4-methyl)-3-hexenoic acid target product of 75%.

After the reaction had ended, MTBE (25 mL) and aqueous NaOH (5%, 50 mL) were added. The phases were separated and the aqueous phase was washed with MTBE (2×25 mL). The aqueous phase was brought to pH=1 with H$_2$SO$_4$ (20%) and extracted with MTBE (3×25 mL). The organic phases from the acidic extraction were combined, washed to neutrality with water (5×25 mL) and dried over MgSO$_4$. After concentration, 2.3 g (27%) of E/Z-(4-methyl)-3-hexenoic acid were obtained as a pale yellow oil with an E/Z ratio of 3:2 ($^1$H NMR). $^{13}$C NMR (d$_8$-toluene); E-(4-methyl)-3-hexenoic acid: 179.7, 140.8, 114.5, 33.7, 32.5, 16.1, 12.6; Z-(4-methyl)-3-hexenoic acid: 179.7, 141.1, 115.5, 33.4, 25.2, 22.8, 12.6.

TABLE II

Carbonylation of linalool

| Example | Transition metal compound | Transition metal (mol %) | TPP/DMAP (mol %) | Ac$_2$O (mol %) | CO (bar) | Conversion after 24 h | Acid sel. (GC area %) |
|---|---|---|---|---|---|---|---|
| 1.13 | Ru(acac)$_3$ | 0.12 | 0.28/0.3 | 28 | 10 | 56% | 60 |
| 1.14 | Ru$_3$(CO)$_{12}$ | 0.04 | 0.28/0.3 | 28 | 10 | 47% | 31 |
| 1.15 | Rh(CO)$_2$(acac) | 0 12 | 0.28/0.3 | 28 | 10 | 58% | 49 |
| 1.16 | Fe(acac)$_2$ | 0.12 | 0.28/0.3 | 28 | 10 | 36% | 49 |
| 1.17 | [Ir(COD)Cl]$_2$ | 0.06 | 0.28/0.3 | 28 | 10 | 49% | 27 |

Example 2: Carbonylation of 3-methyl-1-penten-3-ol

Palladium(II) acetate (22 mg, 0.1 mmol), triphenylphosphine (52 mg, 0.2 mmol) and DMAP (49 mg, 0.4 mmol) were initially charged in a glass autoclave under argon. 3-Methyl-1-penten-3-ol (6.7 g, 67 mmol), triethylamine (6.7 g, 67 mmol) and acetic anhydride (2 g, 20 mmol) were added in an argon counterflow. Subsequently, 10 bar CO was applied and the mixture was stirred at 1000 rpm at this

Example 3: Carbonylation of 1-hepten-3-ol

Palladium(II) acetate (22 mg, 0.1 mmol), triphenylphosphine (52 mg, 0.22 mmol) and DMAP (55 mg, 0.45 mmol) were initially charged in a glass autoclave under argon. 1-Hepten-3-ol (7.6 g, 66 mmol), triethylamine (6.7 g, 67 mmol) and acetic anhydride (1.8 g, 17 mmol) were added in an argon counterflow. Subsequently, 10 bar CO was applied and the mixture was stirred at 1000 rpm at this pressure and at internal temperature 60° C. for 24 h. Thereafter, the mixture was cooled to room temperature and decompressed. GC analysis of the reaction output gave a conversion of 75% with a selectivity for the E/Z-3-octenoic acid target product of 50%.

After the reaction had ended, MTBE (25 mL) and aqueous NaOH (5%, 50 mL) were added. The phases were separated and the aqueous phase was washed with MTBE (2×50 mL). The aqueous phase was brought to pH=1 with $H_2SO_4$ (about 20 mL, 20%) and extracted with MTBE (3×50 mL). The organic phases from the acidic extraction were combined, washed to neutrality with water (4×50 mL) and dried over $MgSO_4$. After concentration, 2.4 g (26%) of E/Z-3-octenoic acid with an E/Z ratio of 78:22 ($^1$H NMR) were obtained.

gave 23 g (61%) of E/Z-homofarnesylic acid with a purity (GC) of 97% with an isomer ratio of E-homofarnesylic acid:Z-homofarnesylic acid of 64:36 (GC).

$^{13}$C NMR (CDCl$_3$): E-homofarnesylic acid: 179.1, 139.8, 135.4, 131.4, 124.4, 123.8, 114.9, 33.6, 39.8, 39.6, 26.8, 25.8, 26.4, 17.8, 16.5, 16.1; Z-homofarnesylic acid: 179.2, 139.7, 135.7, 131.2, 124.5, 123.7, 115.9, 39.8, 33.5, 32.2, 26.8, 26.3, 25.7, 23.4, 17.7, 16.0.

Example 4 was repeated. The feedstocks for carbonylation of E-nerolidol, conversion after 24 h and 6 h and the yield of E/Z-homofarnesylic acid target product (sum of the two isomers) are reported in table III.

TABLE III

Carbonylation of E-nerolidol

| Example | (Pd(OAc)$_2$ (mol %) | TPP (mol %) | DMAP (mol %) | Ac$_2$O (mol %) | CO (bar) | Conversion after 24 h/ (6 h) | (Yield$^\#$ (GC area %) |
|---|---|---|---|---|---|---|---|
| 4     | 0.13 | 0.3  | 0.3 | 23   | 10 | 95%/(65%) | 77% |
| 4.1   | 0.13 | 0.3  | —   | —    | 10 | 0%        | —   |
| 4.2   | 0.13 | 1.3  | 0.3 | 23   | 10 | 50%       | 33% |
| 4.3   | 0.13 | —    | 0.3 | 23   | 10 | 26%       | 1%  |
| 4.4   | 0.13 | 0.3  | 0.3 | —    | 10 | 0%        | —   |
| 4.5   | 0.13 | 0.3  | —   | 23   | 10 | 94%/(54%) | 77% |
| 4.6$^{a)}$ | 0.13 | 0.3 | 0.3 | 23 | 10 | 70% | 54% |
| 4.7   | 0.13 | 0.3  | 0.3 | $^{b)}$ | 10 | 52% | 32% |
| 4.8   | 0.13 | 0.3  | 0.3 | $^{c)}$ | 10 | >99% | 95% |
| 4.9   | 0.13 | 0.3  | —   | $^{d)}$ | 10 | >99% | 58% |
| 4.10$^{e)}$ | 0.13 | 0.3 | 0.3 | 23 | 10 | 34% | 16% |
| 4.11$^{f)}$ | 0.13 | 0.3 | 0.3 | 23 | 10 | 30% | 18% |
| 4.12  | 0.13 | $^{g)}$ | 0.3 | 23 | 10 | 76% | 58% |
| 4.13  | 0.13 | $^{h)}$ | 0.3 | 23 | 10 | 83% | 72% |
| 4.14  | 0.13 | 0.3  | 0.3 | 23   | 20 | 99% | 85% |
| 4.15  | 0.13 | 0.3  | 0.3 | 23   | 40 | 97% | 85% |
| 4.16  | 0.13 | 0.3  | 0.3 | 23   | 80 | 94% | 79% |
| 4.17  | 0.13 | $^{i)}$ | 0.3 | 23 | 20 | 93% | 72% |
| 4.18  | 0.13 | $^{k)}$ | 0.3 | 23 | 20 | 95% | 80% |
| 4.19  | 0.13 | 0.3  | 0.3 | 16   | 20 | 93% | 79% |

$^{a)}$half the amount of NEt$_3$;
$^{b)}$ 23 mol % of allyl acetate (CAS 591-87-7) rather than Ac$_2$O;
$^{c)}$ 30 mol % of E-nerolidyl acetate rather than Ac$_2$O;
$^{d)}$ 30 mol % of E-nerolidyl acetate rather than Ac$_2$O;
$^{e)}$120° C.;
$^{f)}$THF in place of NEt$_3$;
$^{g)}$ 0.3 mol % of P(Cy)$_3$ rather than TPP;
$^{h)}$ 0.3 mol % of tri(p-tolyl)phosphine rather than TPP;
$^{i)}$ 0.3 mol % of di(tert-butyl)phenylphosphine rather than TPP;
$^{k)}$ 0.3 mol % of cyclohexyldiphenylphosphine rather than TPP;
$^\#$yield determined via GC area % as product of selectivity and conversion The NMR data correspond to the data from Wirth et al. Org. Lett., 9, 2007, 3169. $^{13}$C NMR (d$_e$-toluene), E-3-octenoic acid: 179.4, 135.0, 121.4, 38.0, 32.5, 31.6, 22.6, 14.1.

Example 4: Carbonylation of E-nerolidol

Palladium(II) acetate (46 mg, 0.2 mmol), triphenylphosphine (120 mg, 0.46 mmol) and DMAP (56 mg, 0.46 mmol) were initially charged in a steel autoclave under argon. E-nerolidol (34 g, 152.6 mmol), triethylamine (17 g, 167 mmol) and acetic anhydride (3.6 g, 35 mmol) were added in an argon counterflow. Subsequently, 10 bar CO was applied and the mixture was stirred at 1000 rpm at this pressure and at internal temperature 70° C. for 24 h. After 24 h, the mixture was cooled to room temperature and decompressed. GC analysis of the reaction output gave a conversion of 95% with a selectivity for the E/Z-homofarnesylic acid target product of 81%.

After the reaction had ended, the crude product was purified by Kugelrohr distillation (1 mbar, to 170° C.). This Example 5: Carbonylation of E-nerolidyl Acetate Palladium(II) acetate (50 mg, 0.22 mmol), triphenylphosphine (130 mg, 0.5 mmol) and DMAP (70 mg, 0.57 mmol) were initially charged in a steel autoclave under argon. E-Nerolidyl acetate (42.5 g, 142 mmol), triethylamine (9 g, 89 mmol) and water (2.8 g, 156 mmol) were added in an argon counterflow. Subsequently, 10 bar CO was applied and the mixture was stirred at 1000 rpm at this pressure and at internal temperature 70° C. for 24 h. Thereafter, the mixture was cooled to room temperature and decompressed. GC analysis of the reaction output gave a conversion of 97% with a selectivity for E/Z-homofarnesylic acid of 71%. Ratio of E-homofarnesylic acid:Z-homofarnesylic acid=64:36 (GC).

Example 5 was repeated. The feedstocks for carbonylation of E-nerolidyl acetate, conversion after 4 h and 24 h and the yield of the E/Z-homofarnesylic acid target product (sum of the two isomers) are reported in table IV.

TABLE IV

Carbonylation of E-nerolidyl acetate

| Example | Pd(OAc)$_2$ (mol %) | TPP (mol %) | DMAP (mol %) | H$_2$O (eq.) | CO (bar) | Conversion after 24 h (4 h) | GC yield of acid (area %) | Notes |
|---|---|---|---|---|---|---|---|---|
| 5   | 0.15 | 0.4 | 0.4 | 1.1 | 10 | 97% (93%) | 74%  | 70° C. |
| 5.1 | 0.13 | 0.3 | 0.3 | 1.1 | 10 | >99% (65%) | 69% | 70° C., THF rather than NEt$_3$ |
| 5.2 | 0.13 | 0.3 | 0.3 | —   | 10 | >99% | <20% | 70° C. |
| 5.3 | 0.13 | 0.3 | —   | 1.1 | 10 | >99% | 86%  | 70° C. |
| 5.4 | 0.13 | 0.3 | —   | 1.0 | 10 | 97%  | 84%  | 50° C. |

Example 6: Carbonylation of 1-vinylcyclohexanol

Palladium(II) acetate (22 mg, 0.1 mmol), triphenylphosphine (54 mg, 0.21 mmol) and DMAP (50 mg, 0.41 mmol) were initially charged in a glass autoclave under argon. 1-Vinylcyclohexanol (8.35 g, 66 mmol), triethylamine (6.7 g, 67 mmol) and acetic anhydride (1.8 g, 17 mmol) were added in an argon counterflow and 10 bar CO was applied. The mixture was stirred at 1000 rpm at internal temperature 60° C. for 20 h, the pressure was kept at 10 bar, and after 48 h the mixture was cooled to room temperature and decompressed. GC conversion: 54%; selectivity for 3-cyclohexylidenepropanoic acid: 63%.

After the reaction had ended, MTBE (25 mL) and aqueous NaOH (5%, 50 mL) were added. The phases were separated and the aqueous phase was washed with MTBE (2×50 mL). The aqueous phase was brought to pH=1 with H$_2$SO$_4$ (about 30 mL, 20%) and extracted with MTBE (3×50 mL). The organic phases from the acidic extraction were combined, washed to neutrality with water (4×50 mL) and dried over MgSO$_4$. Concentration gave 3.1 g (31%) of 3-cyclohexylidenepropanoic acid. $^{13}$C NMR (d$_6$-toluene): 180.0, 143.8, 112.9, 37.5, 33.3, 29.4, 29.0, 28.1, 27.4.

Example 7: Isomer Separation of a Composition Comprising E/Z-Homofarnesylic Acid and Isomerization for Enrichment of the E-Homofarnesylic Acid Isomer Separation:

The mixture obtained in example 4 was dissolved in n-heptane (100 g), isopropanol (10 g) and Novozym 435 (0.5 g) were added and the mixture was stirred at 60° C. for about 17 h. The enzyme was then filtered off. At a temperature of 0° C., methanol and water were added, and the pH of the reaction mixture was adjusted to 12-13 at a temperature below 10° C. by adding aqueous NaOH. The phases were separated, giving an organic phase comprising (3E,7E)-homofarnesylic acid isopropyl ester as the main component and an aqueous phase having a composition that comprised 3Z,7E-homofarnesylic acid:3E,7E-homofarnesylic acid:2E,7E-homofarnesylic acid:further compounds in a ratio of 68%:14%:17%:1% (HPLC).

Isomerization:

Palladium(II) acetate (22 mg, 0.098 mmol), triphenylphosphine (58 mg, 0.22 mmol) and DMAP (25 mg, 0.2 mmol) were initially charged under argon in a steel autoclave. The acid mixture of 3Z,7E-homofarnesylic acid:3E,7E-homofarnesylic acid:2E,7E-homofarnesylic acid:further compounds (in a ratio of 68%:14%:17%:1%) (17.5 g, 51 mmol), triethylamine (8.1 g, 80 mmol) and acetic anhydride (1.7 g, 17 mmol) were added in an opposing flow of argon, and CO was injected to 20 bar. Subsequently, the mixture was stirred at internal temperature 140° C. for 14 h (1000 rpm). In the course of this, the pressure was maintained at 20 bar. This was followed by cooling to room temperature and decompression. This gave a composition that comprised 3Z,7E-homofarnesylic acid:3E,7E-homofarnesylic acid:2E, 7E-homofarnesylic acid:further compounds in a ratio of 22%:33%:21%:24% (HPLC).

The invention claimed is:

1. A process for preparing a composition comprising at least one unsaturated carboxylic acid of the general formula (I)

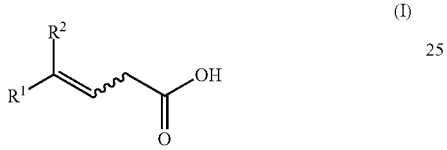

or a salt thereof, in which
R$^1$ is hydrogen, linear or branched C$_1$-C$_{24}$-alkyl, linear or branched C$_2$-C$_{24}$-alkenyl having 1, 2, 3 or more than 3 C—C double bonds, unsubstituted C$_5$-C$_{12}$-cycloalkyl or C$_5$-C$_{12}$-cycloalkyl substituted by 1, 2 or 3 C$_1$-C$_6$-alkyl radicals or unsubstituted aryl or aryl substituted by 1, 2 or 3 C$_1$-C$_6$-alkyl radicals,
R$^2$ is hydrogen, linear or branched C$_1$-C$_{24}$-alkyl or linear or branched C$_2$-C$_{24}$-alkenyl having 1, 2, 3 or more than 3 C—C double bonds, or
R$^1$ and R$^2$ together with the carbon atom to which they are bonded are unsubstituted C$_5$-C$_7$-cycloalkyl or are C$_5$-C$_7$-cycloalkyl bearing 1, 2 or 3 linear or branched C$_1$-C$_6$-alkyl radicals,
in which an allyl alcohol selected from compounds of the general formulae (II.1) and (II.2)

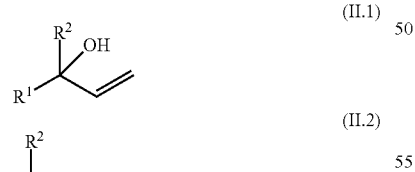

is subjected to a carbonylation by reaction with carbon monoxide in the presence of a transition metal catalyst comprising at least one metal of groups 8, 9 and 10 of the Periodic Table of the Elements, wherein the reaction is additionally effected in the presence of at least one organic phosphorus compound as ligand and in the presence of a substoichiometric amount, based on the allyl alcohol, of a compound A) selected from anhydrides of aliphatic C$_1$-C$_{12}$-monocarboxylic acids, anhydrides of aliphatic C$_4$-C$_{20}$-dicarboxylic acids, anhydrides of cycloaliphatic C$_7$-C$_{20}$-dicarboxylic acids, anhydrides of aromatic C$_8$-C$_{20}$-dicarboxylic acids and acylated allyl alcohols of the formulae (III.1) and (III.2)

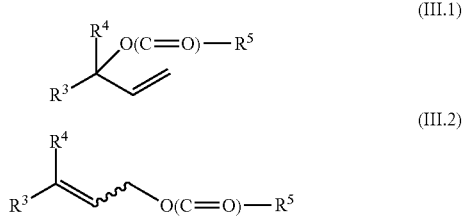

in which
R$^3$ is hydrogen, linear or branched C$_1$-C$_{24}$-alkyl, linear or branched C$_2$-C$_{24}$-alkenyl having 1, 2, 3 or more than 3 C—C double bonds, unsubstituted C$_5$-C$_{12}$-cycloalkyl or C$_5$-C$_{12}$-cycloalkyl substituted by 1, 2 or 3 C$_1$-C$_6$-alkyl radicals or unsubstituted aryl or aryl substituted by 1, 2 or 3 C$_1$-C$_6$-alkyl radicals,
R$^4$ is hydrogen, linear or branched C$_1$-C$_{24}$-alkyl or linear or branched C$_2$-C$_{24}$-alkenyl having 1, 2, 3 or more than 3 C—C double bonds, or
R$^3$ and R$^4$ together with the carbon atom to which they are bonded are unsubstituted C$_5$-C$_7$-cycloalkyl or are C$_5$-C$_7$-cycloalkyl bearing 1, 2 or 3 linear or branched C$_1$-C$_6$-alkyl radicals,
R$^5$ is C$_1$-C$_5$-alkyl,
and wherein the reaction is effected at a temperature of not more than 100° C.

2. A process for preparing a composition comprising at least one unsaturated carboxylic acid of the general formula (I)

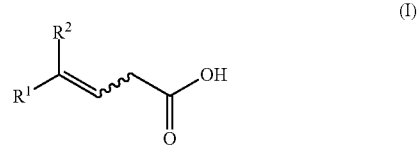

or a salt thereof, in which
R$^1$ is hydrogen, linear or branched C$_1$-C$_{24}$-alkyl, linear or branched C$_2$-C$_{24}$-alkenyl having 1, 2, 3 or more than 3 C—C double bonds, unsubstituted C$_5$-C$_{12}$-cycloalkyl or C$_5$-C$_{12}$-cycloalkyl substituted by 1, 2 or 3 C$_1$-C$_6$- alkyl radicals or unsubstituted aryl or aryl substituted by 1, 2 or 3 $C_1$-$C_6$-alkyl radicals, $R^2$ is hydrogen, linear or branched $C_1$-$C_{24}$-alkyl or linear or branched $C_2$-$C_{24}$-alkenyl having 1, 2, 3 or more than 3 C—C double bonds, or $R^1$ and $R^2$ together with the carbon atom to which they are bonded are unsubstituted $C_5$-$C_7$-cycloalkyl or are $C_5$-$C_7$-cycloalkyl bearing 1, 2 or 3 linear or branched $C_1$-$C_6$-alkyl radicals, in which an acylated allyl alcohol selected from compounds of the general formulae (IV.1) and (IV.2)

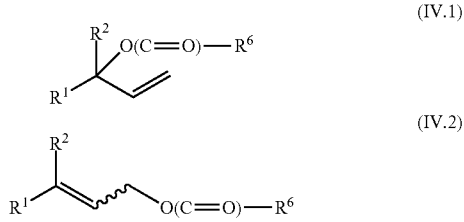

in which $R^6$ is $C_1$-$C_5$-alkyl, is subjected to a carbonylation by reaction with carbon monoxide in the presence of a transition metal catalyst comprising at least one metal of groups 8, 9 and 10 of the Periodic Table of the Elements, wherein the reaction is additionally effected in the presence of at least one organic phosphorus compound as ligand and in the presence of water and wherein the reaction is effected at a temperature of not more than 100° C., wherein the carbonylation is not effected in the presence of an added hydrohalic acid and not in the presence of an added alkali metal halide, alkaline earth metal halide or ammonium halide; and wherein the reaction mixture of the carbonylation has a halide content of not more than 2 mol %, based on the total content of allyl alcohol of the general formulae (IV.1) and (IV.2).

3. The process according to claim 1, wherein the reaction is effected at a pressure of not more than 30 bar.

4. The process according to claim 1, wherein the carbonylation is not effected in the presence of an added hydrohalic acid and not in the presence of an added alkali metal halide, alkaline earth metal halide or ammonium halide.

5. The process according to claim 1, wherein the reaction mixture of the carbonylation has a halide content of not more than 2 mol % based on the total content of allyl alcohol of the general formulae (II.1) and (II.2).

6. The process according to claim 1, wherein the compound A) is selected from acetic anhydride and allyl acetate.

7. The process according to claim 1, wherein the compound A) used is an ester of the formula (III.1) or (III.2) that derives from the alcohol of the formula (II.1) or (II.2) used as the reactant for carbonylation.

8. The process according to claim 1, in which the reaction is additionally effected in the presence of a nucleophilic reagent selected from 4-(di($C_1$-$C_4$-alkyl)amino)pyridine, 4-($C_1$-$C_4$-alkyl)pyridine and 4-(1-pyrrolidinyl)pyridine.

9. The process according to claim 8, in which the nucleophilic reagent selected from 4-(di($C_1$-$C_4$-alkyl)amino)pyridine, 4-($C_1$-$C_4$-alkyl)pyridine and 4-(1-pyrrolidinyl)pyridine, is used in an amount of 0.01 to 5 mol %, based on the total molar amount of the compounds (II.1) and (II.2).

10. The process according to claim 1, in which the transition metal is used for the reaction in an amount of not more than 0.5 mol %, based on the total molar C amount of the compounds (II.1) and (II.2).

11. The process according to claim 1, wherein the transition metal is selected from Pd, Ru, Rh, Ir and Fe.

12. The process according to claim 1, wherein the organic phosphorus compound is selected from trialkylphosphines, triarylphosphines, dialkylarylphosphines, alkyldiarylphosphines, cycloalkyldiarylphosphines, dicycloalkylarylphosphines, tricycloalkyl-phosphines, triheterocyclylphosphines and trihetarylphosphines.

13. The process according to claim 1, in which the total amount of the compound A) is not more than 50 mol %, based on the total molar amount of the compound (II.1) and (II.2).

14. The process according to claim 8, in which the reaction is additionally effected in the presence of a base other than the nucleophilic reagent selected from 4-(dimethylamino)-pyridine, 4-($C_1$-$C_4$-alkyl)pyridine and 4-(1-pyrrolidinyl)pyridine.

15. The process according to claim 1, in which the reaction is effected in the presence of an added aprotic organic solvent.

16. The process according to claim 1, wherein the reaction is effected at a temperature of not more than 80° C.

17. The process according to claim 1, wherein the reaction is effected at a pressure of not more than 25 bar.

18. The process according to claim 1, wherein the compound of the general formula (II.1) which is used for the reaction is selected from nerolidol, linalool, 3-methyl-1-penten-3-ol, 1-hepten-3-ol and 1-vinylcyclohexanol.

19. The process according to claim 1, wherein E-nerolidol is used for the reaction.

20. The process according to claim 1, in which E-nerolidol is subjected to a carbonylation, giving a reaction mixture comprising (3E,7E)-4,8,12-trimethyltrideca-3,7,11-trienoic acid or a salt thereof and (3Z,7E)-4,8,12-trimethyl-trideca-3,7,11-trienoic acid or a salt thereof in a weight ratio of 80:20 to 50:50.

21. The process according to claim 1, wherein the compound of the general formula (II.2) used for the reaction is farnesol.

22. The process according to claim 1, wherein the composition comprising the at least one unsaturated carboxylic acid of the formula (I) is an E/Z isomer mixture of the formula (I) comprising a 3-(E) acid of the formula (I-E) and a 3-(Z) acid of the formula (I-Z)

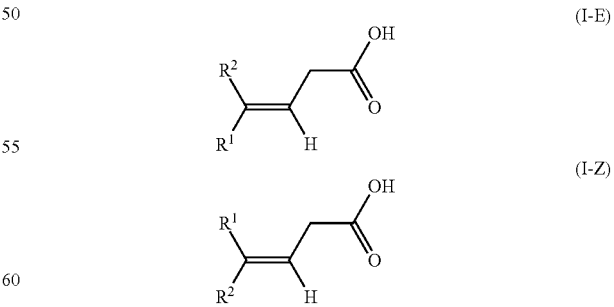

in which $R^1$ and $R^2$ have different definitions and $R^1$ has a higher priority according to IUPAC;

and this E/Z isomer mixture of the formula (I) is subjected to an enrichment of one isomer.

23. The process according to claim 22, wherein the composition comprising the at least one unsaturated carboxylic acid of the formula (I) is an E/Z isomer mixture of the formula (I) comprising a 3-(E) acid of the formula (I-E) and a 3-(Z) acid of the formula (I-Z), in which, in addition, (1) the composition comprising the E/Z isomer mixture of the formula (1), in the presence of an alcohol and of a lipase enzyme, is subjected to an enzyme-catalyzed esterification, wherein the 3-(E) acid of the formula (I-E) is converted at least partly to a 3-(E) ester, so as to obtain a composition comprising the 3-(E) ester, unconverted 3-(E) acid of the formula (I-E) and unconverted 3-(Z) acid of the formula (I-Z);

(2) the composition obtained in (1) is separated to obtain a composition depleted of 3-(E) acid of the formula (I-E) and enriched in 3-(Z) acid of the formula (I-Z), and to obtain a composition comprising the 3-(E) ester;

(3) the composition obtained in (2) which is depleted of 3-(E) acid of the formula (I-E) and enriched in 3-(Z) acid of the formula (I-Z) is subjected to an isomerization to increase the content of 3-(E) acid of the formula (I-E); and (4) optionally, the 3-(E) ester obtained in (2) is cleaved to obtain the 3-(E) acid of the formula (I-E).

24. The process according to claim 22, wherein the composition comprising the at least one unsaturated carboxylic acid of the formula (I) is an E/Z isomer mixture of the formula (I) comprising a 3-(E) acid of the formula (I-E) and a 3-(Z) acid of the formula (I-Z), in which, in addition, (i) the composition comprising the E/Z isomer mixture of the formula (I) is subjected to an esterification in the presence of an alcohol to obtain the 3-(E) ester and the 3-(Z) ester;

(ii) the 3-(E) ester and the 3-(Z) ester obtained in (i) are subjected to a lipase-catalyzed enzymatic hydrolysis, wherein the lipase at least partly cleaves the 3-(E) ester to give the 3-(E) acid of the formula (I-E) to obtain a composition comprising the 3-(E) acid of the compound of the formula (I-E), unconverted 3-(E) ester and unconverted 3-(Z) ester;

(iii) the composition obtained in (ii) is separated to obtain a composition comprising the 3-(E) acid of the compound of the formula (I-E) and to obtain a composition comprising unconverted 3-(E) ester and unconverted 3-(Z) ester;

(iv) the composition which is obtained in (iii) and comprises unconverted 3-(E) ester and unconverted 3-(Z) ester is subjected to an ester cleavage to obtain a composition depleted of 3-(E) acid of the formula (I-E) or salt thereof and enriched in 3-(Z) acid of the formula (I-Z) or salt thereof; and (v) the composition which is obtained in (iv) and is depleted of 3-(E) acid of the formula (I-E) and enriched in 3-(Z) acid of the formula (I-Z) is subjected to an isomerization to increase the content of 3-(E) acid of the formula (I-E).

25. The process according to claim 23, wherein the isomerization to increase the content of 3-(E) acid of the formula (I-E) is effected in the presence of an anhydride of an organic acid and a base.

26. A process for preparing (−)-ambrox (VIII)

in which a1) a mixture of (3E,7E)-4,8,12-trimethyltrideca-3,7,11-trienoic acid and (3Z,7E)-4,8,12-trimethyltrideca-3,7,11-trienoic acid obtainable by the process as defined in claim 1;

b1) the mixture of (3E,7E)-4,8,12-trimethyltrideca-3,7,11-trienoic acid and (3Z,7E)-4,8,12-trimethyltrideca-3,7,11-trienoic acid is subjected to a separation to obtain (3E,7E)-4,8,12-trimethyltrideca-3,7,11-trienoic acid;

c1) the (3E,7E)-4,8,12-trimethyltrideca-3,7,11-trienoic acid is subjected to a reduction to obtain (3E,7E)-homofarnesol (VI);

d1) the (3E,7E)-homofarnesol (VI) is subjected to a cyclization to obtain (−)-ambrox (VIII);

or a2) a mixture of (3E,7E)-4,8,12-trimethyltrideca-3,7,11-trienoic acid and (3Z,7E)-4,8,12-trimethyltrideca-3,7,11-trienoic acid obtainable by the process as defined in claim 1;

b2) the mixture of (3E,7E)-4,8,12-trimethyltrideca-3,7,11-trienoic acid and (3Z,7E)-4,8,12-trimethyltrideca-3,7,11-trienoic acid is subjected to a separation to obtain (3E,7E)-4,8,12-trimethyltrideca-3,7,11-trienoic acid;

c2) the (3E,7E)-4,8,12-trimethyltrideca-3,7,11-trienoic acid is subjected to a cyclization to obtain sclareolide (VII);

d2) the sclareolide (VII) is subjected to a reduction to obtain (−)-ambrox (VIII).

27. The process according to claim 1, wherein the reaction mixture of the carbonylation has a halide content of not more than 1 mol %, based on the total content of allyl alcohol of the general formulae (II.1) and (II.2).

28. The process according to claim 2, wherein the reaction mixture of the carbonylation has a halide content of not more than 1 mol %, based on the total content of esters of the general formulae (IV.1) and (IV.2).

29. The process according to claim 2, wherein the reaction is effected at a pressure of not more than 30 bar.

30. The process according to claim 2, in which the transition metal is used for the reaction in an amount of not more than 0.5 mol %, based on the total molar amount of the compounds (IV.1) and (IV.2).

31. The process according to claim 2, wherein the transition metal is selected from Pd, Ru, Rh, Jr and Fe.

32. The process according to claim 2, wherein the organic phosphorus compound is selected from trialkylphosphines, triarylphosphines, dialkylarylphosphines, alkyldiarylphosphines, cycloalkyldiarylphosphines, dicycloalkylarylphosphines, tricycloalkyl-phosphines, triheterocyclylphosphines and trihetarylphosphines.

33. The process according to claim 2, in which the reaction is effected in the presence of an added aprotic organic solvent.

34. The process according to claim 2, wherein the reaction is effected at a temperature of not more than 80° C.

35. The process according to claim 2, wherein the reaction is effected at a pressure of not more than 25 bar.

36. The process according to claim 2, wherein the composition comprising the at least one unsaturated carboxylic acid of the formula (I) is an E/Z isomer mixture of the formula (I) comprising a 3-(E) acid of the formula (I-E) and a 3-(Z) acid of the formula (I-Z)

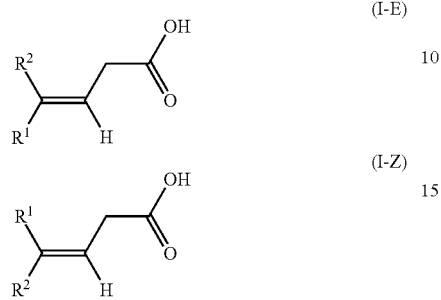

in which
R¹ and R² have different definitions and R¹ has a higher priority according to IUPAC;
and this E/Z isomer mixture of the formula (I), is subjected to an enrichment of one isomer.

37. The processing according to claim 36, wherein the composition comprising the at least one unsaturated carboxylic acid of the formula (I) is an E/Z isomer mixture of the formula (I) comprising a 3-(E) acid of the formula (I-E) and a 3-(Z) acid of the formula (I-Z), in which, in addition,
(1) the composition comprising the E/Z isomer mixture of the formula (1), in the presence of an alcohol and of a lipase enzyme, is subjected to an enzyme-catalyzed esterification, wherein the 3-(E) acid of the formula (I-E) is converted at least partly to a 3-(E) ester, so as to obtain a composition comprising the 3-(E) ester, unconverted 3-(E) acid of the formula (I-E) and unconverted 3-(Z) acid of the formula (I-Z);
(2) the composition obtained in (1) is separated to obtain a composition depleted of 3-(E) acid of the formula (I-E) and enriched in 3-(Z) acid of the formula (I-Z), and to obtain a composition comprising the 3-(E) ester;
(3) the composition obtained in (2) which is depleted of 3-(E) acid of the formula (I-E) and enriched in 3-(Z) acid of the formula (I-Z) is subjected to an isomerization to increase the content of 3-(E) acid of the formula (I-E); and
(4) optionally, the 3-(E) ester obtained in (2) is cleaved to obtain the 3-(E) acid of the formula (I-E).

38. The process according to claim 36, wherein the composition comprising the at least one unsaturated carboxylic acid of the formula (I) is an E/Z isomer mixture of the formula (I) comprising a 3-(E) acid of the formula (I-E) and a 3-(Z) acid of the formula (I-Z), in which, in addition,
(i) the composition comprising the E/Z isomer mixture of the formula (I) is subjected to an esterification in the presence of an alcohol to obtain the 3-(E) ester and the 3-(Z) ester;
(ii) the 3-(E) ester and the 3-(Z) ester obtained in (i) are subjected to a lipase-catalyzed enzymatic hydrolysis, wherein the lipase at least partly cleaves the 3-(E) ester to give the 3-(E) acid of the formula (I-E) to obtain a composition comprising the 3-(E) acid of the compound of the formula (I-E), unconverted 3-(E) ester and unconverted 3-(Z) ester;
(iii) the composition obtained in (ii) is separated to obtain a composition comprising the 3-(E) acid of the compound of the formula (I-E) and to obtain a composition comprising unconverted 3-(E) ester and unconverted 3-(Z) ester;
(iv) the composition which is obtained in (iii) and comprises unconverted 3-(E) ester and unconverted 3-(Z) ester is subjected to an ester cleavage to obtain a composition depleted of 3-(E) acid of the formula (I-E) or salt thereof and enriched in 3-(Z) acid of the formula (I-Z) or salt thereof; and
(v) the composition which is obtained in (iv) and is depleted of 3-(E) acid of the formula (I-E) and enriched in 3-(Z) acid of the formula (I-Z) is subjected to an isomerization to increase the content of 3-(E) acid of the formula (I-E).

39. The process according to claim 37, wherein the isomerization to increase the content of 3-(E) acid of the formula (I-E) is effected in the presence of an anhydride of an organic acid and a base.

40. A process for preparing (−)-ambrox (VIII)

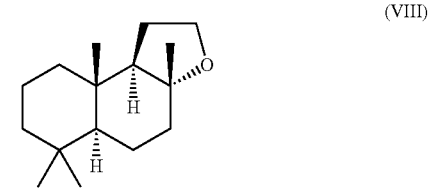

in which
a1) a mixture of (3E,7E)-4,8,12-trimethyltrideca-3,7,11-trienoic acid and (3Z,7E)-4,8,12-trimethyltrideca-3,7,11-trienoic acid obtainable by the process as defined in claim 2;
b1) the mixture of (3E,7E)-4,8,12-trimethyltrideca-3,7,11-trienoic acid and (3Z,7E)-4,8,12-trimethyltrideca-3,7,11-trienoic acid is subjected to a separation to obtain (3E,7E)-4,8,12-trimethyltrideca-3,7,11-trienoic acid;
c1) the (3E,7E)-4,8,12-trimethyltrideca-3,7,11-trienoic acid is subjected to a reduction to obtain (3E,7E)-homofarnesol (VI);
d1) the (3E,7E)-homofarnesol (VI) is subjected to a cyclization to obtain (−)-ambrox (VIII);
or
a2) a mixture of (3E,7E)-4,8,12-trimethyltrideca-3,7,11-trienoic acid and (3Z,7E)-4,8,12-trimethyltrideca-3,7,11-trienoic acid obtainable by the process as defined in claim 2;
b2) the mixture of (3E,7E)-4,8,12-trimethyltrideca-3,7,11-trienoic acid and (3Z,7E)-4,8,12-trimethyltrideca-3,7,11-trienoic acid is subjected to a separation to obtain (3E,7E)-4,8,12-trimethyltrideca-3,7,11-trienoic acid;
c2) the (3E,7E)-4,8,12-trimethyltrideca-3,7,11-trienoic acid is subjected to a cyclization to obtain sclareolide (VII);
d2) the sclareolide (VII) is subjected to a reduction to obtain (−)-ambrox (VIII).

* * * * *

UNITED STATES PATENT AND TRADEMARK OFFICE
CERTIFICATE OF CORRECTION

PATENT NO. : 11,192,873 B2  
APPLICATION NO. : 16/487161  
DATED : December 7, 2021  
INVENTOR(S) : Schelwies et al.

Page 1 of 1

It is certified that error appears in the above-identified patent and that said Letters Patent is hereby corrected as shown below:

In the Specification

At Column 3, Lines 47-52, compound (E,Z)-Nerolidol:

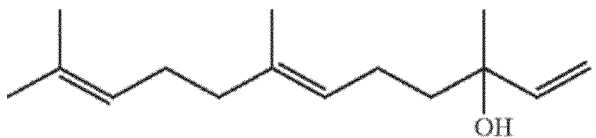

(E/Z)-Nerolidol

Should be shown as:

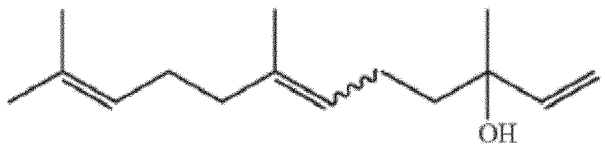

(E/Z)-Nerolidol

At Column 3, Lines 60-65, compound (3E/Z,7E)-Homofarnesylic acid:

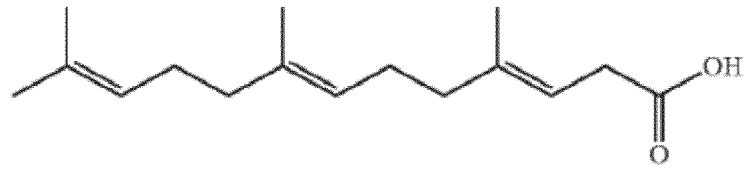

(3E/Z, 7E) - Homofarnesylic acid

Should be shown as:

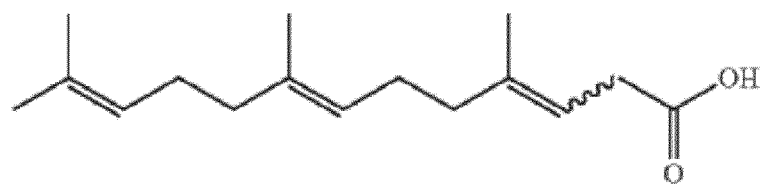

(3E/Z,7E)-Homofarnesylic acid

Signed and Sealed this  
Second Day of August, 2022

*Katherine Kelly Vidal*

Katherine Kelly Vidal  
*Director of the United States Patent and Trademark Office*